(12) United States Patent
Foxwell et al.

(10) Patent No.: US 7,651,857 B2
(45) Date of Patent: *Jan. 26, 2010

(54) METHODS FOR ENHANCING ANTIGEN PRESENTATION

(75) Inventors: Brian Maurice John Foxwell, London (GB); Marc Feldmann, London (GB)

(73) Assignee: The Mathilda and Terence Kennedy Institute of Rheumatology Trust, London (GB)

( * ) Notice: Subject to any disclaimer, the term of this patent is extended or adjusted under 35 U.S.C. 154(b) by 44 days.

This patent is subject to a terminal disclaimer.

(21) Appl. No.: 10/450,786

(22) PCT Filed: Dec. 21, 2001

(86) PCT No.: PCT/GB01/05724

§ 371 (c)(1),
(2), (4) Date: Oct. 10, 2003

(87) PCT Pub. No.: WO02/051430

PCT Pub. Date: Jul. 4, 2002

(65) Prior Publication Data

US 2004/0086516 A1    May 6, 2004

(30) Foreign Application Priority Data

Dec. 22, 2000  (GB) ................. 0031454.2
Nov. 17, 2001  (GB) ................. 0127625.2

(51) Int. Cl.
*C12N 15/86* (2006.01)
*C12P 21/04* (2006.01)
*A61K 39/00* (2006.01)
*A61K 39/235* (2006.01)

(52) U.S. Cl. .................. 435/456; 435/70.3; 424/198.1; 424/233.1

(58) Field of Classification Search .......... None
See application file for complete search history.

(56) References Cited

U.S. PATENT DOCUMENTS

| | | |
|---|---|---|
| 4,987,071 A | 1/1991 | Foxwell et al. |
| 5,093,246 A | 3/1992 | Foxwell et al. |
| 5,116,742 A | 5/1992 | Foxwell et al. |
| 5,149,796 A | 9/1992 | Foxwell et al. |
| 5,168,053 A | 12/1992 | Altman et al. |
| 5,180,818 A | 1/1993 | Cech et al. |
| 6,887,684 B2 * | 5/2005 | Sims et al. ............ 435/69.1 |
| 2003/0023993 A1 * | 1/2003 | Medzhitov et al. ........... 800/8 |
| 2003/0125235 A1 | 7/2003 | Foxwell et al. |
| 2003/0153518 A1 | 8/2003 | Foxwell et al. |
| 2004/0086516 A1 | 5/2004 | Foxwell et al. |
| 2004/0241152 A1 | 12/2004 | Foxwell et al. |

FOREIGN PATENT DOCUMENTS

| | | |
|---|---|---|
| WO | WO 91/06571 | 5/1991 |
| WO | WO 92/07573 | 5/1992 |
| WO | WO 94/10323 | 5/1994 |
| WO | WO 94/24281 | 10/1994 |
| WO | WO 96/03144 | 2/1996 |
| WO | WO 00/26249 | 5/2000 |
| WO | 01/47543 A | 7/2001 |
| WO | 01/88137 A | 11/2001 |

OTHER PUBLICATIONS

Underhill, D.M, et al. Toll-like recpetor-2 mediates myobacteria-induced proinflammatory signaling in macrophages. Proc. Natl. Acad. Sci. USA. 1999. vol. 96, No. 25, p. 14459-14463.*
Bancereau J., et al. Immunobiology of dendritic cells. 2000. Ann. Rev. Immunol. vol. 18, pp. 767-811.*
Underhill, D.M., et al. Toll-like receptor-2 mediates mycobacteria-induced proinflammatory signaling in macrophages. 1999. Proc. Natl. Acad. Sci. USA. vol. 96, No. 26, pp. 14459-14463.*
Rhee S.H. and Hwang, D. Murine Toll-like receptor 4 confers lipopolysaccharide responsiveness as determined by activation of NF-κB and expression of the inducible cyclooxygenase. 2000. J. Biol. Chem. vol. 275, No. 44, pp. 34035-34040.*
Conti, P. et al. Human recombinant IL-1 receptor antagonist (IL-1Ra) inhibits leukotriene B4 generation from human monocyte suspensions stimulated by lipopolysaccharide (LPS). 1993. Clin. Exp. Immunol. vol. 91, pp. 526-531.*

(Continued)

*Primary Examiner*—Robert Landsman
*Assistant Examiner*—Bruce D Hissong
(74) *Attorney, Agent, or Firm*—Nixon & Vanderhye P.C.

(57) ABSTRACT

We describe (1) a method of enhancing antigen presentation, comprising the step of supplying to an antigen presenting cell such as a dendritic cell, or precursor cell, an inhibitor of Toll-related receptor (TRR) signalling and (2) a method of inhibiting antigen presentation, comprising the step of supplying to an antigen presenting cell such as a dendritic cell, or precursor cell, an enhancer of Toll-related receptor (TRR) signalling. The inhibitor of TRR signalling may be a dominant negative mutant of MyD88, for example MyD88lpr.

21 Claims, 21 Drawing Sheets

OTHER PUBLICATIONS

Figure 1:
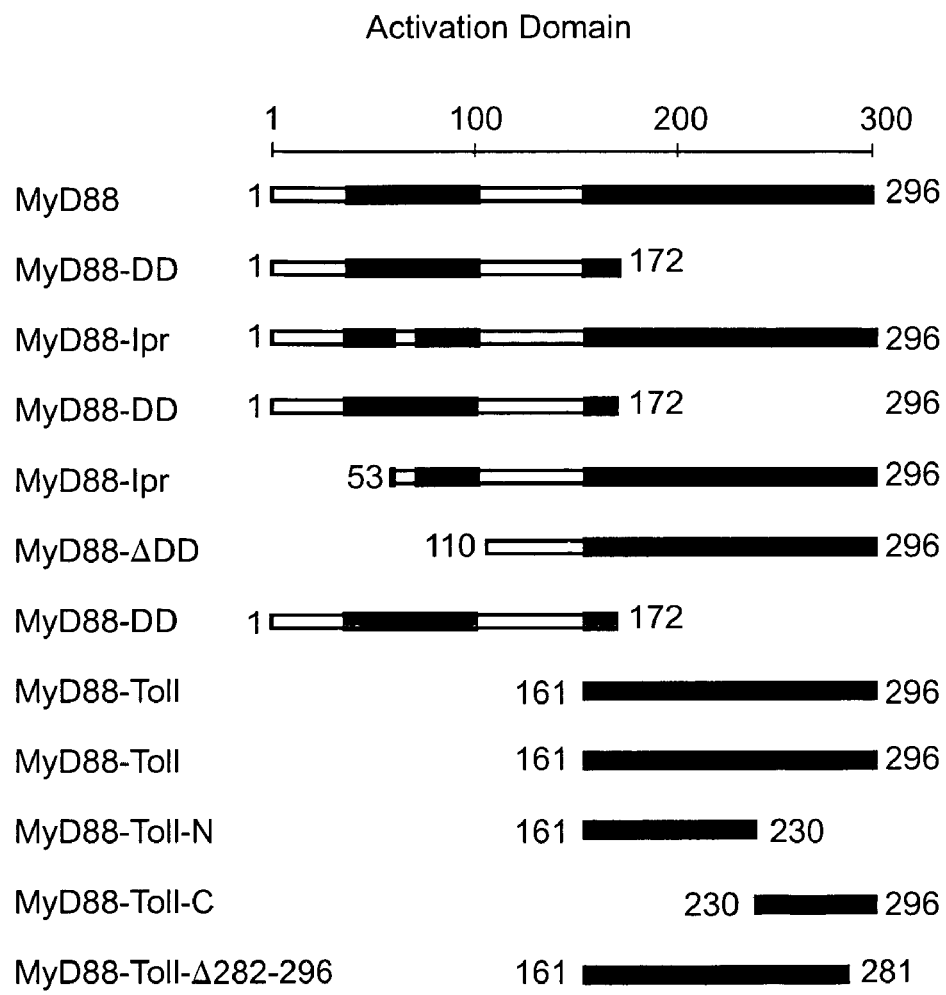

Bondeson J. et al. Selective regulation of cytokine induction by adenoviral gene transfer of IκBa into human macrophages . . . independent. 1999. J. Immunol. vol. 162, pp. 2939-3945.*
Dietz, A.B. and Vuk-Pavlovic, S. High efficiency adenoviral-mediated gene transfer to human dendritic cells. 1998. Blood. vol. 91, No. 2, pp. 392-398.*
Burns, K. et al. MyD88, an adaptor protein involved in interleukin-1 signaling. 1998. J. Biol. Chem. vol. 273, No. 20, pp. 12203-12209.*
Stratagene, 1988 Catalog. p. 39.*
Deeg H.J. and R. Huss. Major histocompatibility complex class II molecules, hemopoiesis and the marrow microenvironment. Bone Marrow Transplantation. 1993. vol. 12, pp. 425-430.*
Mickle JE et al. Genotype-phenotype relationships in cystic fibrosis. Med. Clin. North Am. 2000. vol. 84, No. 3, p. 597-607.*
Kowalczyk D, et al. Modulation of monocyte antigen-presenting capacity by tumour necrosis factor-alpha (TNF): opposing effects of exogenous TNF before and after an antigen pulse and the role of TNF gene activation in monocytes. Immunology Letters. 1995. vol. 44, pp. 51-57.*
Veber et al., Conformationally restricted bicyclic analogs of somatostatin. Proc. Natl. Acad. Sci. USA. 75:2636-2640 (1978).*
Stauss & Dahl. Cellular ongogenes for tumour immunity: Immunotherapy. Tumour Immunology, Dalgleish/Browning, Chapter 7 (1995).*
Janssens et al. "Identification and Characterization of a Splice Variant of MyD88" Scandinavian Journal of Immunology, vol. 51, Supplement 1, Jun. 2000, p. 69, XP001068581.
Dupraz et al. "Dominant Negative MyD88 Proteins Inhibit Interleukin-1β/ Interferon-γ-Mediated Induction of Nuclear Factor κB-Dependent Nitrite Production and Apoptosis In β Cells" Journal of Biological Chemistry, vol. 275, No. 48, Dec. 1, 2000, pp. 37672-37678. XP002235043.
O'Neil et al. "The IL-1 Receptor/Toll-Like Receptor Superfamily: Crucial Receptors for Inflammation and Host Defense" Immunology Today, vol. 21, No. 5, May 2000, pp. 206-209, XP004198146.
Takeuchi et al. "Cellular Responses to Bacterial Cell Wall Components are Mediated Through MyD88-Dependent Signaling Cascades" International Immunology, vol. 12, No. 1, Jan. 2000, pp. 113-117, XP002945405.
Burns et al. "MyD88, An Adapter Protein Involved in Interleukin-1 Signaling" Journal of Biological Chemistry, vol. 273, No. 20, May 15, 1998, pp. 12203-12209, XP000985939.
Hardiman et al. "Genetic Structure and Chromosomal Mapping of MyD88" Genomics, vol. 45, 1997, pp. 332-339, XP002927805.
Ardeshna et al. "The P13 Kinase, P38 SAP Kinase, and NF-κB Signal Transduction Pathways are Involved in the Survival and Maturation of Lippolysaccharide-Stimulated Human Monocyte-Derived Dedritic Cells" Blood; vol. 96, No. 3, Aug. 1, 2000, pp. 1039-1046.
Lee et al. "Cyclosporine A Inhibits the Expression of Costimulatory Molecules on in Vitro-Generated Dendritic Cells" Transplantation, vol. 68, No. 9, Nov. 15, 1999, p. 1255-1263.
Underhill et al. "Toll-Like Receptor-2 Mediates Mycobacteria-Induced Proinflammatory Signaling in Macrophages" PNAS, vol. 96, No. 25, Dec. 7, 1999, pp. 14459-14463.
Burns et al. "Tollip, A New Component of the IL-1RI Pathway, Links IRAK to the IL-1 Receptor" Nature Cell Biology, vol. 2, Jun. 2000, pp. 346-351.
Horng et al. "TIRAP: An Adapter Molecule in the Toll Signaling Pathway" Nature Immunology, vol. 2, No. 9, Sep. 2001, pp. 835-841.
Fitzgerald et al. "MAL (MyD88-Adapter-Like) is Required for Toll-Like Receptor-4 Signal Transduction" Nature, vol. 415, Sep. 6, 2001, pp. 78-83.
GenBank Accession NM_002468 (2003).
GenBank Accession NM_010851 (2003).
GenBank Accession AF378129 (2001).
GenBank Accession AF378130 (2001).
Stauss & Dahl "Cellular oncogenes for tumour immunity: Immunotherapy" in: Dalgleish & Browning (eds.) *Tumour Immunology*, Cambridge Univ. Press, Chapter 7, pp. 153-184 (1996).

Ashley et al. "Bone marrow-generated dendritic cells pulsed with tumor extracts or tumor RNA induce antitumor immunity against central nervous system tumors" J. Exp. Med. 186:1177-1182 (1997).
Banchereau et al. "Immunology of dendritic cells" Ann. Rev. Immunol. 18:767-811 (2000).
Better et al. "*Escherichia coli* secretion of an active chimeric antibody fragment" Science 240:1041-1043 (1988).
Bird et al. "Single-chain antigen-binding proteins" Science 242:423-426 (1998).
Bischoff et al. "An adenovirus mutant that replicates selectively in p53-deficient human tumor cells" Science 274:373-376 (1996).
Bohl et al. "Control of erythropoietin delivery by doxycycline in mice after intramuscular injection of adeno-associated vector" Blood 92:1512-1517 (1998).
Boldin et al. "Self-association of the "Death Domains" of the p55 tumor necrosis factor (TNF) receptor and Fas/APO1 prompts signaling for TNF and Fas/APO1 effects" J. Biol. Chem. 270:387-391 (1995).
Bondeson et al. "Effective adenoviral transfer of IκBα into human fibroblasts and chondrosarcoma cells reveals that the induction of matrix metalloproteinases and proinflammatory cytokines is nuclear factor-κB dependent" J. Rheumatol. 27:2078-2089 (2000).
Bonnert et al. "The cloning and characterization of human MyD88: A member of an IL-1 receptor related family" FEBS Letters 402:81-84 (1997).
Büeler et al. "Adeno-associated viral vectors for gene transfer and gene therapy" Biol. Chem. 380:613-622 (1999).
Burchell et al. "The *MUC1* gene as an immunogen: Use of naked DNA and role of dendritic cells" in *Breast Cancer, Advances in Biology and Therapeutics* (Calvo et al. eds.), John Libbey Eurotext pp. 309-313 (1996).
Burns et al. "Tollip, a new component of the IL-1RI pathway, links IRAK to the IL-1 receptor" Nature Cell Biol. 2:346-351 (2000).
Cao et al. "TRAF6 is a signal transducer for interleukin-1" Nature 383:443-446 (1996).
Conry et al. "Polynucleotide-mediated immunization therapy of cancer" Seminars in Oncology 23:135-147 (1996).
Condon et al. "DNA-based immunization by in vivo transfection of dendritic cells" Nature Medicine 2:1122-1127 (1996).
Cotten et al. "High-efficiency receptor-mediated delivery of small and large (48 kilobase gene constructs using the endosome-disruption activity of defective or chemically inactivated adenovirus particles" Proc. Natl. Acad. Sci. USA 89:6094-6098 (1992).
Curiel et al. "Adenovirus facilitation of molecular conjugate-mediated gene transfer" Prog. Med. Virol. 40:1-18 (1993).
De Brujin et al. "Immunization with human papilomavirus type 16 (HPV16) oncoprotein-loaded dendritic cells as well as protein in adjuvant induces MHC class I-restricted protection to HPV16-induced tumor cells" Cancer Res. 58:724-730 (1998).
Derossi et al. "Trojan peptides: The penetratin system for intracellular delivery" Trends Cell Biol. 8:84-87 (1998).
Dietrich et al. "Bacterial systems for the delivery of eukaryotic antigen expression vectors" Antisense Nucleic Acid Drug Development 10:391-399 (2000).
Du et al. "Three novel mammalian toll-like receptors: gene structure, expression, and evolution" Eur. Cytokine Netw. 11:362-371 (2000).
Duncan et al. "A new reagent which may be used to introduce sulfhydryl groups into proteins, and its use in the preparation of conjugates for immunoassay" Anal. Biochem. 132:68-73 (1983).
Dushay & Eldon "*Drosophila* immune responses as models for human immunity" Am. J. Hum. Genet. 62:10-14 (1998).
Foxwell et al. "Adenoviral transgene delivery provides an approach to identifying important molecular processes in inflammation: Evidence for heterogenecity in the requirement for NFκB in tumour necrosis factor production" Ann. Rheum. Dis. 59 (Suppl. 1):54-59 (2000).
Frankel et al. "Antisense oligonucleotide-induced inhibition of adrenocorticotropic hormone release from cultured human corticotrophs" J. Neurosurg. 91:261-267 (1999).
Girolomoni & Ricciardi-Castagnoli "Dendritic cells hold promise for immunotherapy" Immunology Today 18:102-104 (1997).

Gong et al. "Induction of antigen-specific antitumor immunity with adenovirus-transduced dendritic cells" Gene Therapy 4:1023-1028 (1997).

Gong et al. "Induction of antitumor activity by immunization with fusions of dendritic and carcinoma cells" Nature Medicine 3:558-561 (1997).

Goodchild et al. "Inhibition of human immunodeficiency virus replication by antisense oligodeoxynucleotides" Proc. Natl. Acad. Sci. USA 85:5507-5511 (1988).

Grabbe et al. "Dendritic cells as initiators of tumor immune responses: A possible strategy for tumor immunotherapy?" Immunology Today 16:117-121 (1995).

Graham et al. "Intramuscular immunisation with *MUC1* cDNA can protect C57 mice challenged with MUC1-expressing syngeneic mouse tumour cells" Int. J. Cancer 65:664-670 (1996).

Kwak et al. "Transfer of myeloma idiotype-specific immunity from an actively immunised marrow donor" Lancet 345:1016-1020 (1995).

Hardiman et al. "Molecular characterization and modular analysis of human *MyD88*" Oncogene 13:2467-2475 (1996).

Harroch et al. "5' upstream sequences of MyD88, an IL-6 primary response gene in M1 cells: Detection of functional IRF-1 and stat factors binding sites" Nucleic Acids Research 23:3539-3546 (1995).

He et al. "Identification of c-*MYC* as a target of the APC pathway" Science 281:1509-1512 (1998).

Hsu et al. "Vaccination of patients with B-cell lymphoma using autologous antigen-pulsed dendritic cells" Nature Medicine 2:52-58 (1996).

Huang et al. "NMR structure and mutagenesis of the Fas (APO-1/CD95) death domain" Nature 384:638-641 (1996).

Huston et al. "Protein engineering of antibody binding sites: Recovery of specific activity in an anti-digoxin single-chain Fv analogue produced in *Escherichia coli*" Proc. Natl. Acad. Sci. USA 85:5879-5883 (1988).

Jaffe et al. "Culture of human endothelial cells derived from umbilical veins" J. Clin. Invest. 52:2745-2756 (1973).

Jiang et al. "Prevention of constitutive TNF receptor 1 signaling by silencer of death domains" Science 283:543-546 (1999).

Kawai et al. "Unresponsiveness of MyD88-deficient mice to endotoxin" Immunity 11:115-122 (1999).

Kim et al. "Introduction of soluble proteins into the MHC class I pathway by conjugation to an HIV *tat* peptide" J. Immunol. 159:1666-1668 (1997).

Kuriyama et al. "A potential approach for gene therapy targeting hepatoma using a liver-specific promoter on a retroviral vector" Cell Structure and Function 16:503-510 (1991).

Ledley "Nonviral gene therapy: The promise of genes as pharmaceutical products" Human Gene Therapy 6:1129-1144 (1995).

Magari et al. "Pharmacologic control of a humanized gene therapy system implanted into nude mice" J. Clin. Invest. 100:2865-2872 (1997).

Martin & Paphadjopoulos "Irreversible coupling of immunoglobulin fragments to preformed vesicles" J. Biol. Chem. 257:286-288 (1982).

Medzhitov et al. "MyD88 is an adaptor protein in the hToll/IL-1 receptor family signaling pathways" Mol. Cell 2:253-258 (1998).

Mellman et al. "Antigen processing for amateurs and professionals" Trends in Cell Biology 8:231-237 (1998).

Mézière et al. "In vivo T helper cell response to retro-inverso peptidomimetics" J. lmmunol. 159:3230-3237 (1997).

Michael et al. "Addition of a short peptide ligand to the adenovirus fiber protein" Gene Therapy 2:660-668 (1995).

Miller & Vile "Targeted vectors for gene therapy" FASEB J. 9:190-199 (1995).

Mitcham et al. "T1/ST2 signaling establishes it as a member of an expanding interleukin-1 receptor family" J. Biol. Chem. 271:5777-5783 (1996).

Morrison et al. "Chimeric human antibody molecules: Mouse antigen-binding domains with human constant region domains" Proc. Natl. Acad. Sci. USA 81:6851-6855 (1984).

Murphy et al. "Phase I clinical trial: T-cell therapy for prostate cancer using autologous dendritic cells pulsed with HLA-A0201-specific peptides from prostate-specific membrane antigen" The Prostate 29:371-380 (1996).

Muzio et al. "IRAK (Pelle) family member IRAK-2 and MyD88 as proximal mediators of IL-1 signaling" Science 278:1612-1615 (1997).

Muzio et al. "Differential expression and regulation of toll-like receptors (TLR) in human leukocytes: Selective expression of TLR3 in dendritic cells" J. Immunol. 164:5998-6004 (2000).

Nagata "Apoptosis by death factor" Cell 88:355-365 (1997).

Nagata "Mutations in the Fas antigen gene in *Ipr* mice" Seminars in Immunology 6:3-8 (1994).

Nässander et al. "In vivo targeting of OV-TL3 Immunoliposomes to ascitic ovarian carcinoma cells (OVCAR-3) in athymic nude mice" Cancer Research 52:646-653 (1992).

Nestle et al. "Vaccination of melanoma patients with peptide- or tumor lysate-pulsed dendritic cells" Nature Medicine 4:328-332 (1998).

Neuberger et al. "Antibody Engineering" 8th International Biotechnology Symposium (Part 2) pp. 792-799 (1988).

O'Neil & Dinarello "The IL-I receptor/toll-like receptor superfamily: Crucial receptors for inflammation and host defense" Immunology Today 21:206-209 (2000).

O'Sullivan et al. "Comparison of two methods of preparing enzyme-antibody conjugates: Application of these conjugates for enzyme immunoassay" Anal. Biochem. 100:100-108 (1979).

Poltorak et al. "Defective LPS signaling in C3H/HeJ and C57BL/10ScCr mice: Mutations in *Tlr4* gene" Science 282:2085-2088 (1998).

Rivera et al. "Long-term regulated expression of growth hormone in mice after intramuscular gene transfer" Proc. Natl. Acad. Sci. USA 96:8657-8662 (1999).

Rosenfeld et al. "Adenovirus-mediated transfer of a recombinant α1-antitrypsin gene to the lung epithelium in vivo" Science 252:431-434 (1991).

Rock et al. "A family of human receptors structurally related to *Drosophila* Toll" Proc. Natl. Acad. Sci. USA 95:588-593 (1998).

Roth et al. "Activation of cloned human CD4$^+$ TH$_1$ and TH$_2$ cells by blood dendritic cells" Scand. J. Immunol. 43:646-651 (1996).

Sherman & Spatola "Compatibility of thioamides with reverse turn features: Synthesis and conformational analysis of two model cyclic pseudopeptides containing thioamides as backbone modifications" J. Am. Chem. Soc. 112:433-441 (1990).

Skerra & Plückthun "Assembly of a functional immunoglobulin Fv fragment in *Escherichia coli*" Science 240:1038-1041 (1988).

Specht et al. "Dendritic cells retrovirally transduced with a model antigen gene are therapeutically effective against established pulmonary metastases" J. Exp. Med. 186: 1213-1221 1997.

Szabolcs et al. "Retrovirally transduced human dendritic cells express a normal phenotype and potent T-cell stimulatory capacity" Blood 90:2160-2167 (1997).

Thomson et al. "Recombinant polyepitope vaccines for the delivery of multiple CD8 cytotoxic T cell epitopes" J. Immunol. 157:822-826 (1996).

Thorsett et al. "Dipeptide mimics conformationally restricted inhibitors of angiotensin-converting enzyme" 111:166-170 (1983).

Tjoa et al. "Follow-up evaluation of prostate cancer patients infused with autologous dendritic cells pulsed with PSMA peptides" The Prostate 32:272-278 (1997).

Tüting et al. "Genetically modified bone marrow-derived dendritic cells expressing tumor-associated viral or "self" antigens induce antitumor immunity in vivo" Eur. J. Immunol. 27:2702-2707 (1997).

Underhill et al. "The Toll-like receptor 2 is recruited to macrophage phagosomes and discriminates between pathogens" Nature 401:811-815 (1999).

van der Bruggen et al. "A gene encoding an antigen recognized by cytolytic T lymphocytes on a human melanoma" Science 254-1643-1647 1991.

Verma & Somia "Gene therapy-promises, problems and prospects" Nature 389:239-242 (1997).

Wagner et al. "Transferinn-polycation conjugates as carriers for DNA uptake into cells" Proc. Natl. Acad. Sci. USA 87:3410-3414 (1990).

Walther & Stein "Cell type specific and inducible promoters for vectors in gene therapy as an approach for cell targeting" J. Mol. Med. 74:379-392 (1996).

Wan et al. "Dendritic cells transduced with an adenoviral vector encoding a model tumor-associated antigen for tumor vaccination" Human Gene Therapy 8:1355-1363 (1997).

Ward et al. "Binding activities of a repertoire of single immunoglobulin variable domains secreted from *Escherichia coli*" Nature 341-544-546 (1989).

Whiteside et al. "Identification of novel factors that bind to the PRD I region of the human β-interferon promoter" Nucleic Acids Research 20:1531-1538 (1992).

Winter & Milstein "Man-made antibodies" Nature 349:293-299 (1991).

Witters et al. "Antisense oligonucleotides to the epidermal growth factor receptor" Breast Cancer Research and Treatment 53:41-50 (1999).

Zhai et al. "Antigen-specific tumor vaccines. Development and characterization of recombinant adenoviruses encoding MART1 or gp100 for cancer therapy" J. Immunol. 156:700-710 (1996).

Zhang et al. "Bacterial lipopolysaccharide activates nuclear factor-κB through interleukin-1 signaling mediators in cultured human dermal endothelial cells and mononuclear phagocytes" J. Biol. Chem. 274:7611-7614 (1999).

Zhou & Tedder "A distinct pattern of cytokine gene expression by human CD83[+] blood dendritic cells" Blood 86:3295-3301 (1995).

* cited by examiner

Human Skin Fibroblasts

Anti-flag MyD88

NF-κB

Phospho-p38 MAPK

Phospho-p42/44 MAPK

Phospho-p42/44 MAPK / IκBα

Human Umbilical Vein Endothelical Cells

|  | No stimulus | +IL-1 | +LPS |
|---|---|---|---|
|  | Adβ-gal  ADMyD88-lpr | Adβ-gal  ADMyD88-lpr | Adβ-gal  ADMyD88-lpr |

← Flag-MyD88-lpr

← IκBα

← Phospho-p42/44 MAPK

← NF-κB

FIG. 19A
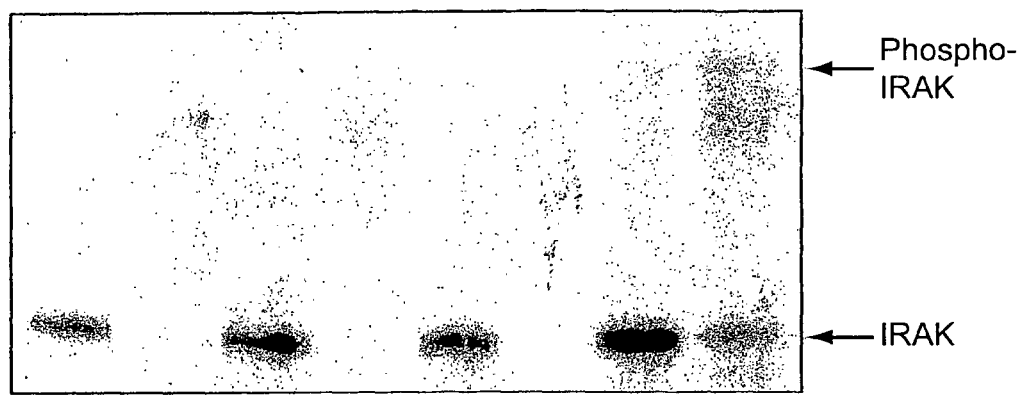
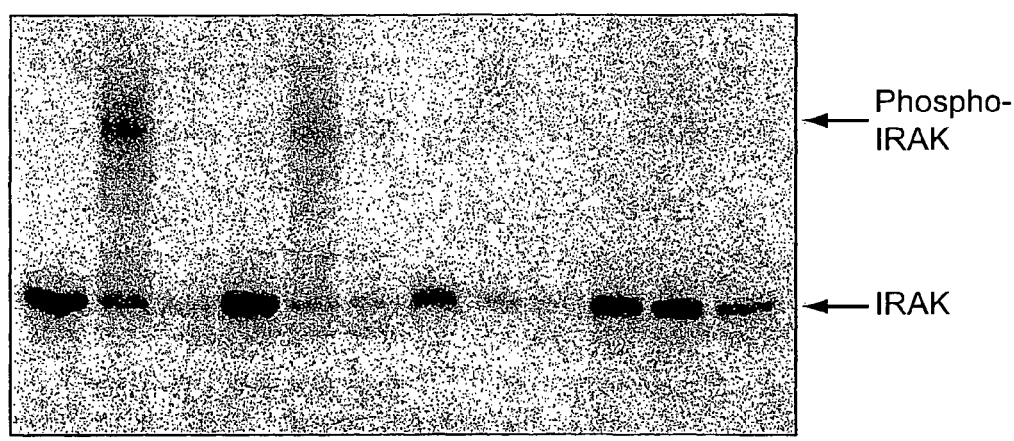
FIG. 19B

Macrophage cytokine production after 2 days overexpression

| | TNFα (pg/ml) | IL-6 (pg/ml) | IL-8 (pg/ml) |
|---|---|---|---|
| Uninfected | <20 | <50 | 1000-3000 |
| Ad0 | <20 | <50 | 1000-3000 |
| AdMyD88wt | <20 | <50 | 1000-3000 |
| AdMyD88-lpr | 40-500(max1000) | 500-1500 | 10000-15000 |

FIG. 21A

Time-course of macrophage cytokine production after infection with AdMyD88-lpr

| | TNFα (pg/ml) | IL-6 (pg/ml) | IL-8 (pg/ml) |
|---|---|---|---|
| 0h | <20 | <70 | 1700 |
| 4h | <20 | <70 | 2200 |
| 24h | 170 | 490 | 14200 |
| 48h | 70 | 750 | 13500 |

FIG. 21B

METHODS FOR ENHANCING ANTIGEN PRESENTATION

This application is the US national phase of international application PCT/GB01/05724 filed 21 Dec. 2001, which designated the US.

The present invention relates to modulation of the immune system, particularly modulation of antigen presentation by dendritic cells.

Central to the recognition mechanisms of the immune system are a number of germline-encoded receptors known as toll-like receptors (TLRs) (1). Individual TLRs activate specialised anti-fungal or anti-bacterial genes through the activation of the NF-κB transcription factors (2). Thus, TLR4 has been shown to confer responsiveness to bacterial lipopolysaccharide (3) whereas TLR2 confers responsiveness to bacterial peptidoglycan and lipoteichoic acid as well as yeast carbohydrates (4). 9 TLRs are currently known (8) and many more expected to exist.

Although the extracellular portions of Toll-related receptors (TRRs), including TLRs, are relatively divergent, the cytoplasmic portions are more conserved. They contain a well-defined region known as the toll domain, which is also found in the cytoplasmic portion of proteins comprising the IL-1 receptor, the IL-18 receptor and other receptors broadly termed the IL-1 receptor family. In addition, soluble cytoplasmic proteins such as MyD88, TollIP, Mal and TIRAP can have Toll domains. TLRs and IL-1 receptor use an analogous framework of signalling; upon ligand binding, they recruit the adaptor molecule MyD88 through homotypic interactions with a toll domain that MyD88 contains in its C-terminus. MyD88, in turn, recruits IRAK and TRAF-6 to activate NF-κB and mitogen-activated,protein kinases. TollIP may also be involved (2. Burns et al (2000) *Nature cell Biol.* 2, 346-351).

The MyD88 (myeloid differentiation protein) is considered to have a modular organisation consisting of an N-terminal death domain (DD) separated by a short linker from a C-terminal Toll domain (reviewed in (5)). The N-terminal DD is related to a motif of approximately 90 amino acids that is considered to mediate protein-protein interactions with other DD sequences forming either homo- or heterodimers (Boldin et al (1995) *J Biol Chem* 270, 387-391).

The MyD88 Toll domain has about 130 amino acids (Mitcham et al (1996) *J Biol Chem* 199, 144-146). Toll domains are also considered to mediate protein-protein interactions with other Toll domains forming either homo- or heterodimers (see (5)).

DD and Toll-Toll interactions are considered to be involved in directing signalling pathways. MyD88 is considered to bind via its Toll domain to TLRs and the IL-1 receptor (when bound to ligand). In turn, MyD88 is considered to bind via its DD to other DD-containing proteins; in particular it is considered to bind to IRAK and TRAF-6, thereby activating NF-κB and mitogen-activated protein kinases (2).

Antigen presenting cells are well known in the art and include dendritic cells (see Janeway, C A Jr & Tavers, P, Immunobiology (3rd Edition), Editions Current Biology/Churchill Livingstone and Garland Publishing). They are highly specialised cells that can process antigens and display their peptide fragments on the cell surface, together with molecules required for lymphocyte activation. The most potent antigen—presenting cells are dendritic cells, macrophages and B cells.

Dendritic cells (DC) are professional antigen-processing and -presenting cells which are critical to the development of primary MHC-restricted T-cell immunity. They originate from a $CD34^+$ precursor in bone marrow, but can also be derived from a post colony-forming unit $CD14^+$ intermediate in the peripheral blood. DC migrate to peripheral sites in skin, mucosa, spleen and thymus. They have been implicated in a variety of clinically important processes, including allograft rejection, atopic disorders, autoimmunity and anti-tumour immunity.

DC are cultured ex vivo from $CD34^+$ stem cells or $CD14^+$ peripheral blood monocytes using cytokines, principally GM-CSF, IL-4 and TNFα. DC from both these sources are immunocompetent and can take up exogenously presented antigen, process it and then present it to cytotoxic T-cells (Grabbe et al (1995) *Immunology Today* 16, 117-121; Girolomoni & Ricciardi-Castagnoli (1997) *Immunology Today* 18, 102-104). DC can transfer antigen-specific tumour immunity generated in vivo (Kwak et al (1995) *Lancet* 345, 1016-1020) and autologous DC pulsed with tumour antigen ex vivo can induce a measurable anti-tumour effect (Hsu et al (1996) *Nature Medicine* 2, 52-58). DC can be effectively pulsed using a crude tumour membrane lysate, purified peptides or peptide fragments. The ex vivo expansion of autologous dendritic cells from patients, loading with a peptide antigen and reinfusion as adoptive immunotherapy, is described in, for example, WO/00/26249.

We surprisingly show that there is an inhibitory signal, specific for antigen presenting cells (APCs) such as dendritic cells and macrophages, that acts through MyD88. The inhibitory signal may involve one or more TRRs.

TRRs include molecules such as TLRs, IL-1 receptor family members including IL-1 receptor and IL-18 receptor and cytoplasmic proteins such as MyD88, TollIP, Mal and TIRAP.

Molecules that modulate, preferably block TRR signalling in APCs, such as dendritic cells, for example loss-of-function (inhibitory eg dominant negative) forms of MyD88, may be used as immunostimulatory agents, for example with DNA vaccines and cancer immunotherapy. For example, incorporation of inhibitory MyD88 into DNA vectors stimulates T cell and antibody responses more efficiently than if the vectors are used alone.

A first aspect of the invention provides a method of enhancing antigen presentation, comprising the step of supplying to an antigen-presenting cell (APC), such as a dendritic cell, or precursor cell, a modulator, preferably an inhibitor, of a Toll-related receptor (TRR) signalling. The modulator activates APCs. for example DCs, for example enhances antigen presentation by APCs, for example DCs.

A second aspect of the invention provides a method of inhibiting antigen presentation, comprising the step of supplying to an antigen-presenting cell (APC), such as a dendritic cell, or precursor cell, a modulator, preferably an enhancer, of Toll-related receptor (TLR) signalling.

The inhibitor of Toll-related receptor (TRR) signalling preferably inhibits a TRR signalling pathway found in APCs, such as dendritic cells, or a precursor thereof. In further preference, the inhibitor inhibits a TRR signalling pathway, the inhibition of which induces activation of immature dendritic cells and/or enhancement of antigen-presenting function and may induce NF-κB nuclear translocation or the activation of MAP kinases. Thus, the TRR signalling pathway is considered to contribute to maintenance of immature APCs, such as dendritic cells, in the immature form, and to maintenance of NF-κB in an inactive form. Activation of the TRR signalling pathway may reduce the response of immature APCs, such as dendritic cells, to maturing factors, for example GM-CSF and IL4. ie may reduce the number of mature APCs, such as dendritic cells, formed, or may increase the time or dose of maturing factors needed for a given number of mature APCs, such as dendritic cells, to form. Activation of the TRR signalling pathway may reduce the ability of mature APCs, such as dendritic cells, to induce a MLR (mixed lymphocyte reaction), a test of APC, such as dendritic cell, function well known to those skilled in the art. The APCs, such as dendritic cells, are incubated with allogeneic T cells and proliferation of the cells is measured, for example by measuring tritiated thymidine uptake after 6 days. For example, $10^5$ T cell may be plated with graded doses (for example from 50 to 10000 per well) of dendritic cells in a 96-well round-bottom microtiter plate.

Typically, the APC is a professional antigen-presenting cell such as a mucosal cell, macrophage or B cell. MHC Class II molecules are found in professional APCs. Professional APCs are characterised by the presence of costimulatory molecules such as CD80 and CD86 as defined by Mellman et al (1998) *Trends Cell Biol.* 8, 231-237.

Typically, isolated precursor or dendritic cells in which the pathway is stimulated express higher levels of HLA-DR, MHC Class I and CD80/86 compared to unstimulated cells.

A list of DC surface markers regulated upon enhancement of antigen-presenting function is given in Banchereau et al (2000) *Ann. Rev. Immunol.* Dendritic cell surface markers include high CCR1, CCR5. CCR6 but low CCR7 chemokine receptors; high CD68; low levels of MHC Class I (HLA-A, B, C) and MHC Class II (HLA-DR, HLA-DQ and HLA-DP); low co-stimulatory molecules such as CD40, CD54, CD80. CD83 and CD86 and no DC-LAMP. Activated DC with increased antigen presentation have low CCR1, CCR5, CCR6; high CCR7; low CD68; high surface MHC Class I and II; high co-stimulatory molecules such as CD40, CD54, CD58, CD80, CD83, CD86; high DC-LAMP and high p55 fascin.

The term "inhibitor of Toll-related receptor (TRR) signalling" may include a modulator of any one of the following steps in an APC (such as DC) TRR signalling pathway:

i) binding of an agonist or antagonist to a TRR, ie binding of a TRR to an extracellular molecule, ii) binding of the TRR to an intracellular molecule (TRR interacting molecule), for example a polypeptide, for example an adaptor molecule, for example a molecule comprising a Toll domain, for example MyD88, Mal (Fitzgerald et al (2001) *Nature* 415, 78-83), TIRAP Horng et al (2001) *Nature Immunol* 7, 835-841) or TollIP (Burns et al (2000) *Nature Cell Biol* 2, 346-351);

iii) binding of a TRR interacting molecule to a second intracellular molecule, for example a polypeptide. For example MyD88 may bind to a polypeptide comprising a death domain (DD), as discussed above. A molecule that binds to MyD88 in an APC such as a DC may be IRAK or TRAF-6 or possibly TollIP. IRAK is described in Medzhitov et al (1998) *Mol. Cell* 2, 253-258; IRAK2 is described in Muzio et al (1997) *Science* 278, 1612-1615; TollIP is describe in Burns et al (2000) *Nature Cell Biol.* 2, 346-351; and TRAF6 is described in Dushay & Eldon (1998) *Am J Hum. Genet.* 62, 10-14 and Cao et al (1996) *Nature* 383, 443-446;

iv) further signalling steps (for example involving polypeptide: polypeptide binding, or changes in phosphorylation state of a polypeptide, or changes in particular phosphoinositide levels; possibilities will be well known to those skilled in the art) leading to inhibition of maturation of immature DC. The further signalling steps may promote maintenance of NF-κB in an inactive form. As an example of a further signalling step, the second intracellular molecule may interact with a third or further intracellular molecule, for example a polypeptide such as IκB kinases or MAPkinases. The interaction may involve a change in covalent modification of a polypeptide, for example phosphorylation or dephosphorylation of the third intracellular polypeptide by the second intracellular molecule or proteolytic cleavage or ubiquitination.

As noted above, APCs such as dendritic cells are considered to have a TRR signalling pathway that inhibits NF-κB nuclear translocation (activation). Thus, it will be appreciated that a compound that increases NF-κB activation/nuclear translocation is not considered to be an activator of TRR signalling in an APC such as DC.

Similarly, a compound that inhibits NF-κB activation/nuclear translocation is not considered to be an inhibitor of TRR signalling in an APC such as a DC.

It is preferred that the inhibitor or enhancer of TRR signalling in an APC such as a DC does not act on a signalling pathway component or step that is shared by the APC inhibitory TRR signalling pathway and any signalling pathway in an APC that leads to activation of NF-κB.

It is preferred that the inhibitor or enhancer of TRR signalling in an APC acts at one of steps (i), (ii) or (iii) above, preferably step (ii) or (iii). Thus, it is preferred that the inhibitor or enhancer of TRR signalling in an APC acts to modulate binding of an extracellular molecule to a TRR (ie binding to an extracellular portion of the TRR); or to modulate binding of an intracellular molecule to a TRR (ie binding to an intracellular portion of the TRR); or to modulate binding of such an intracellular molecule to a further intracellular molecule. It is particularly preferred that the inhibitor or enhancer of TRR signalling modulates the binding of (functional) MyD88 to a TRR or the binding of (functional) MyD88 to a further intracellular molecule, for example a polypeptide comprising a DD. Thus, it is preferred that the inhibitor or enhancer of TRR signalling in an APC such as DC acts to modulate signalling steps directly involving MyD88.

Alternatively, it is preferred that the modulator, for example inhibitor or enhancer, of TRR signalling in an APC such as DC acts to modulate signalling steps directly involving another TRR interacting molecule or adapter, for example Mal (Fitzgerald et al (2001)) or TIRAP (Horng et al (2001)) or TollIP (Burns et al (2000)). TIRAP and Mal, for example, both contain TIR domains, but do not contain a Death Domain (DD). It is considered that wild-type TIRAP or wild-type Mal may have a similar effect in APC such as DC to a mutant of MyD88 which lacks a functional DD, for example a similar effect to MyD88lpr. TollIP may contain a DD. It is considered that a mutant of TollIP which lacks a functional DD may have a similar effect in APC such as DC to a mutant of MyD88 which lacks a functional DD, for example a similar effect to MyD88lpr.

The modulator of TRR signalling in an APC such as DC may be TIRAP or Mal or a fragment, fusion or variant thereof. Alternatively, it may be TollIP (Burns et al (2000)) or a fragment, fusion or variant thereof.

The inhibitor may also be a ribozyme which selectively destroy mRNA encoding a TRR, or an antisense molecule which prevents transcription of a TRR.

Ribozymes which may be encoded in the genomes of the viruses or virus-like particles herein disclosed are described in Cech and Herschlag, "Site-specific cleavage of single stranded DNA" U.S. Pat. No. 5,180,818; Altman et al "Cleavage of targeted RNA by RNAse P" U.S. Pat. No. 5,168,053, Cantin et al "Ribozyme cleavage of HIV-1 RNA" U.S. Pat. No. 5,149,796; Cech et al "RNA ribozyme restriction endoribonucleases and methods", U.S. Pat. No. 5,116,742; Been et al "RNA ribozyme polymerases, dephosphorylases, restriction endonucleases and methods", U.S. Pat. No. 5,093,246;

and Been et al "RNA ribozyme polymerases, dephosphorylases, restriction endoribonucleases and methods; cleaves single-stranded RNA at specific site by transesterification", U.S. Pat. No. 4,987,071, all incorporated herein by reference.

Antisense oligonucleotides are single-stranded nucleic acids, which can specifically bind to a complementary nucleic acid sequence. By binding to the appropriate target sequence, an RNA-RNA, a DNA-DNA, or RNA-DNA duplex is formed. These nucleic acids are often termed "antisense" because they are complementary to the sense or coding strand of the gene. Recently, formation of a triple helix has proven possible where the oligonucleotide is bound to a DNA duplex. It was found that oligonucleotides could recognise sequences in the major groove of the DNA double helix. A triple helix was formed thereby. This suggests that it is possible to synthesise a sequence-specific molecules which specifically bind double-stranded DNA via recognition of major groove hydrogen binding sites.

By binding to the target nucleic acid, the above oligonucleotides can inhibit the function of the target nucleic acid. This could, for example, be a result of blocking the transcription, processing, poly(A)addition, replication, translation, or promoting inhibitory mechanisms of the cells, such as promoting RNA degradations.

Antisense oligonucleotides are prepared in the laboratory and then introduced into cells, for example by microinjection or uptake from the cell culture medium into the cells, or they are expressed in cells after transfection with plasmids or retroviruses or other vectors carrying an antisense gene. Antisense oligonucleotides were first discovered to inhibit viral replication or expression in cell culture for *Rous sarcoma* virus, *vesicular stomatitis* virus, *herpes simplex* virus type 1, simian virus and influenza virus. Since then, inhibition of mRNA translation by antisense oligonucleotides has been studied extensively in cell-free systems including rabbit reticulocyte lysates and wheat germ extracts. Inhibition of viral function by antisense oligonucleotides has been demonstrated in vitro using oligonucleotides which were complementary to the AIDS HIV retrovirus RNA (Goodchild, J. 1988 "Inhibition of Human Immunodeficiency Virus Replication by Antisense Oligodeoxynucleotides", *Proc. Natl. Acad. Sci. (USA)* 85(15), 5507-11). The Goodchild study showed that oligonucleotides that were most effective were complementary to the poly(A) signal; also effective were those targeted at the 5' end of the RNA, particularly the cap and 5' untranslated region, next to the primer binding site and at the primer binding site. The cap, 5' untranslated region, and poly(A) signal lie within the sequence repeated at the ends of retrovirus RNA (R region) and the oligonucleotides complementary to these may bind twice to the RNA.

Typically, antisense oligonucleotides are 15 to 35 bases in length. For example, 20-mer oligonucleotides have been shown to inhibit the expression of the epidermal growth factor receptor mRNA (Witters et al, *Breast Cancer Res Treat* 53:41-50 (1999)) and 25-mer oligonucleotides have been shown to decrease the expression of adrenocorticotropic hormone by greater than 90% (Frankel et al, *J Neurosurg* 91:261-7 (1999)). However, it is appreciated that it may be desirable to use oligonucleotides with lengths outside this range, for example 10, 11, 12, 13, or 14 bases, or 36, 37, 38, 39 or 40 bases.

The anti-sense nucleic acid may be encoded by a suitable vector.

A further aspect of the invention provides a method of treating a patient in need of enhancement of antigen presentation comprising the step of supplying a modulator, preferably an inhibitor, of Toll-related receptor (TRR) signalling to the patient or to an antigen presenting cell such as a dendritic cell, or a precursor cell, of the patient. The modulator activates APCs, such as DCs. The modulator may activate certain signalling pathways, such as kinase pathways, for example MAP kinases p42 or p44/erk1/erk2, p54/Jnk, p38 MAP kinases or NFκB. The modulator or inhibitor may be MyD88, Mal, TIRAP or TollIP or a fragment, fusion or variant any thereof, preferably a fragment, fusion or variant that retains a functional TIR but may not have a functional DD (for example may not have a DD, or may have a mutated DD which does not function as a DD, for example does not interact with another (functional) DD).

Thus, a further aspect of the invention provides a method of treating a patient in need of enhancement of antigen presentation comprising the step of supplying MyD88, Mal, TIRAP or TollIP to the patient or to an antigen presenting cell such as a dendritic cell, or a precursor cell, of the patient. By MyD88, Mal, TIRAP or TollIP is included a fragment, fusion or variant thereof, preferably a fragment, fusion or variant that retains a functional TIR but may not have a functional DD.

A further aspect of the invention provides a method of treating a patient in need of inhibition of antigen presentation comprising the step of supplying a modulator, preferably an enhancer, of Toll-related receptor (TRR) signalling to the patient or to an antigen-presenting dendritic cell, or precursor cell, of the patient. The modulator or enhancer may be a fragment, fusion or variant of MyD88, Mal or TIRAP or TollIP (or may be MyD88, Mal or TIRAP or TollIP), preferably a fragment, fusion or variant that retains some, but not all, of the binding or catalytic properties of MyD88, Mal or TIRAP or TollIP, respectively. The modulator or enhancer inhibits APCs, for example DCs, for example inhibits presentation of antigen by APCs, for example DCs. The modulator may inhibit certain signalling pathways, such as kinase pathways, for example MAP kinases p42 or p44/erk1/erk2, p54/Jnk, p38 MAP kinases or NFκB.

A further aspect of the invention provides a method of treating a patient in need of inhibition of antigen presentation comprising the step of supplying a fragment, fusion or variant of MyD88, Mal, TIRAP or TollIP to the patient or to an antigen-presenting dendritic cell, or precursor cell, of the patient. The fragment, fusion or variant inhibits APCs, for example DCs, for example inhibits antigen presentation by APCs, preferably DCs. The fragment, fusion or variant preferably retains some, but not all, of the binding or catalytic properties of MyD88, Mal, TIRAP or TollIP, respectively.

A further aspect of the invention provides a method of treating a patient in need of enhancement of antigen presentation comprising the step of supplying to the patient, or to an antigen-presenting cell (APC) such as a dendritic cell, or dendritic precursor cell of the patient, an inhibitor of a signalling step (occuring in the APC such as a DC) directly involving MyD88. The inhibitor may be a dominant negative mutant of MyD88.

A further aspect of the invention provides a method of treating a patient in need of enhancement of antigen presentation comprising the step of supplying to the patient, or to an antigen presenting cell such as a dendritic cell, or precursor cell, of the patient, a dominant negative mutant of MyD88.

Dominant negative mutants include portions of MyD88 that may include fragments of the molecule which include the death domain (DD) or Toll domain, or portions thereof. Some examples are described in Reference (5). Preferably, the dominant negative mutants are ones which inhibit IL-1 or TRR signalling such as by the activation of IRAK or production of cytokines in fibroblasts or HUVECs.

A further aspect of the invention provides a method of treating a patient in need of inhibition of antigen presentation comprising the step of supplying to the patient, or to an antigen-presenting cell (APC) such as a dendritic cell, or precursor cell, of the patient, an enhancer of a signalling step (occuring in the APC such as DC) directly involving MyD88. The enhancer may be functional MyD88, for example wild-type MyD88.

The signalling inhibitor or enhancer (for example TRR signalling inhibitor or enhancer, or inhibitor or enhancer of a signalling step directly involving MyD88) is preferably specifically targeted to the APCs, such as dendritic cells, or precursor cells, but this may not be essential.

The signalling inhibitor or enhancer may be supplied to the patient or patient's cells by administration of the inhibitor or enhancer to the patient or patient's cells, or by being expressed in cells of the patient. Thus, supply may be achieved by administering to the patient (or to an APC or precursor cell of the patient; for example such a cell removed from the patient for manipulation and subsequent return to the patient) a recombinant polynucleotide encoding (and capable of expressing) a signalling inhibitor or enhancer.

The enhancer may increase MyD88 signalling activity. For example, the enhancer may be a MyD88 molecule with wild-type activity, or a constitutively active MyD88 molecule. For example the enhancer may be a MyD88 molecule lacking a functional Toll domain (ie lacking a domain that is capable of binding to a Toll domain); it may be a MyD88 mutant in which the Toll domain is deleted and/or non-functional, for example a MyD88-DD polypeptide as described in (5). Alternatively, the MyD88 mutant may be one in which the death domain is deleted and/or is non-functional, for example Myd88lpr. Thus, as an example, a recombinant polynucleotide capable of expressing a wild-type MyD88 may be administered to the patient.

The MyD88 molecule with wild-type activity may be wild-type MyD88. preferably a mouse human wild-type MyD88, still more preferably a MyD88 that is expressed in mouse or human DC, or a mutated MyD88 which retains the activity of wild type MyD88 ie has a functional Toll domain and a functional death domain (DD; ie has a domain that is capable of binding to a death domain). It is preferred that the MyD88 Toll domain and/or DD are unmutated, ie that any mutation lies outside these domains.

It is preferred that the MyD88 has the sequence indicated in Hardiman et al (1996) *Oncogene* 13, 2467-2475; or Bonnert et al (1997) *FEBS Lett.* 402, 81-84; or Hardiman et al (1997) *Genomics* 45, 332-339, all of which are human. The human sequence is also given in Gen Bank Accession No. NM-002468.

The mouse MyD88 sequence is given in Harroch et al (1995) *Nucl. Acids Res.* 23, 3539-3546 and Hardiman et al (1997) *Genomics* 45, 332-339 and Gen Bank Accession No. NM-010851.

Human MyD88 is 82% identical in amino acid sequence to the mouse MyD88.

The human and mouse sequences for TIRAP are shown in Horng et al (2001) *Nature Immunol* 7, 835-841 and in Genbank Accession Nos AF378129 and AF378131, respectively.

The human and mouse sequences for Mal are shown in Fitzgerald et al (2001) *Nature* 413, 78-83.

The human, mouse and *C. elegans* sequences for TollIP are given in Burns et al (2000) *Nature cell Biol* 2, 346-351.

It is preferred that any mutation is a conservative substitution, as well known to those skilled in the art. By "conservative substitutions" is intended combinations such as Gly, Ala; Val, Ile, Leu; Asp, Glu; Asn, Gln; Ser, Thr; Lys, Arg; and Phe, Tyr. Mutations may be made using the methods of protein engineering and site-directed mutagenesis as well known to those skilled in the art.

The three-letter and one-letter amino acid code of the IUPAC-IUB Biochemical Nomenclature Commission is used herein. The sequence of polypeptides are given N-terminal to C-terminal as is conventional. It is preferred that the amino acids are L-amino acids, but they may be D-amino acid residues.

An enhancer of MyD88 signalling may act by binding to MyD88 or a binding partner of MyD88, for example by binding to a binding partner that inhibits the signalling activity of MyD88. For example MyD88lpr may act by displacing a natural inhibitor of TRR signalling. The natural inhibitor may be related to the SODD polypeptide that inhibits TNFα signalling. SODD is described in Jiang et al (1999) *Science* 283, 1852-1855.

The inhibitor may be an inhibitor of MyD88 signalling activity. It may bind to MyD88 or a binding partner of MyD88 and inhibit binding of MyD88 to a binding partner. This may disrupt signalling via MyD88. For example, the inhibitor may inhibit binding of MyD88 to the Toll domain of a TRR, and/or may inhibit binding of MyD88 to a polypeptide comprising a DD, for example IRAK or TRAF-6 or TollIP.

The inhibitor or enhancer may be a drug-like compound. The term "drug-like compound" is well known to those skilled in the art, and may include the meaning of a compound that has characteristics that may make it suitable for use in medicine, for example as the active ingredient in a medicament. Thus, for example, a drug-like compound may be a molecule that may be synthesised by the techniques of organic chemistry, less preferably by techniques of molecular biology or biochemistry, and is preferably a small molecule, which may be of less than 5000 daltons. A drug-like compound may additionally exhibit features of selective interaction with a particular protein or proteins and be bioavailable and/or able to penetrate cellular membranes, but it will be appreciated that these features are not essential.

The inhibitor or enhancer may be an antibody, by which term is included antibody fragments or antibody-like molecules, as well known to those skilled in the art. Preferably, the antibody binds to MyD88 (or other adapter molecule, for example Mal, TIRAP or TollIP) or to a binding partner of MyD88 (or other adapter molecule). For example, the antibody may bind to the DD of MyD88 (and/or to the DD of a binding partner of MyD88), and may disrupt binding of MyD88 to a DD of a binding partner of MyD88. Alternatively, the antibody may bind to the Toll domain of MyD88 (and/or to the Toll domain of a binding partner of MyD88), and may disrupt binding of MyD88 to a Toll domain of a binding partner of MyD88. The antibody may preferably bind to an epitope of MyD88 that comprises the residue equivalent to Phe56 of wild-type mouse MyD88.

By an antibody is included an antibody or other immunoglobulin, or a fragment or derivative thereof, as discussed further below.

The variable heavy ($V_H$) and variable light ($V_L$) domains of the antibody are involved in antigen recognition, a fact first recognised by early protease digestion experiments. Further confirmation was found by "humanisation" of rodent antibodies. Variable domains of rodent origin may be fused to constant domains of human origin such that the resultant antibody retains the antigenic specificity of the rodent parented antibody (Morrison et al (1984) *Proc. Natl. Acad. Sci. USA* 81, 6851-6855).

That antigenic specificity is conferred by variable domains and is independent of the constant domains is known from experiments involving the bacterial expression of antibody fragments, all containing one or more variable domains. These molecules include Fab-like molecules (Better et al (1988) *Science* 240, 1041); Fv molecules (Skerra et al (1988) *Science* 240, 1038); single-chain Fv (ScFv) molecules where the $V_H$ and $V_L$ partner domains are linked via a flexible oligopeptide (Bird et al (1988) *Science* 242, 493; Huston et al (1988) *Proc. Natl. Acad. Sci. USA* 85, 5879) and single domain antibodies (dAbs) comprising isolated V domains (Ward et al (1989) *Nature* 341, 544). A gene: review of the techniques involved in the synthesis of antibody fragments which retain their specific binding sites is to be found in Winter & Milstein (1991) *Nature* 349, 293-299.

By "ScFv molecules" we mean molecules wherein the $V_H$ and $V_L$ partner domains are linked via a flexible oligopeptide.

The advantages of using antibody fragments, rather than whole antibodies, are several-fold. The smaller size of the fragments may lead to improved pharmacological properties. Effector functions of whole antibodies, such as complement binding, are removed. Fab, Fv, ScFv and dAb antibody fragments can all be expressed in and secreted from *E. coli*, thus allowing the facile production of large amounts of the said fragments. Fragments may also be expressed in cells of the patient.

Whole antibodies, and F(ab')$_2$ fragments are "bivalent". By "bivalent" we mean that the said antibodies and F(ab')$_2$ fragments have two antigen combining sites. In contrast, Fab, Fv. ScFv and dAb fragments are monovalent, having only one antigen combining sites.

Preferably, the antibody has an affinity for the epitope of between about $10^5.M^{-1}$ to about $10^{12}.M^{-1}$, more preferably at least $10^8.M^{-1}$.

Antibodies reactive towards a chosen polypeptide may be made by methods well known in the art. In particular, the antibodies may be polyclonal or monoclonal.

Suitable monoclonal antibodies to selected antigens may be prepared by known techniques, for example those disclosed in "*Monoclonal Antibodies: A manual of techniques*", H Zola (CRC Press, 1988) and in "*Monoclonal Hybridoma Antibodies: Techniques and Applications*", J G R Hurrell (CRC Press, 1982). Chimaeric antibodies are discussed by Neuberger et al (1988, 8*th International Biotechnology Symposium* Part 2, 792-799). Suitably prepared non-human antibodies can be "humanized" in known ways, for example by inserting the CDR regions of mouse antibodies into the framework of human antibodies.

Techniques for preparing antibodies are well known to those skilled in the art, for example as described in Harlow, E D & Lane, D. "Antibodies: a laboratory manual" (1988) New York Cold Spring Harbor Laboratory. Suitable antibodies and techniques for preparing suitable antibodies may be described in (5).

The antibody (particularly antibody fragment) may be joined to a moiety that facilitates uptake of the antibody by a cell, for example a DC. For example, the antibody may be linked to a lipophilic molecule or polypeptide domain that is capable of promoting cellular uptake of the molecule or the interacting polypeptide, as known to those skilled in the art. Thus, the moiety may derivable from the Antennapedia helix 3 (Derossi et al (1998) *Trends Cell Biol* 8, 84-87), or from sequences of HIV, generally tat, that permit entry into cells. Alternatively, a polynucleotide, for example cDNA, encoding the antibody may be delivered in a vector, permitting expression of the antibody in the cell, as indicated above.

The inhibitor may be an inhibitory MyD88 molecule, preferably a dominant inhibitory MyD88 molecule (ie capable of inhibiting signalling by wild-type MyD88 molecules, for example in a cell in which wild-type and inhibitory MyD88 molecules are present). The inhibition may arise from blocking interaction of endogenous wild-type MyD88 with a binding partner of the endogenous MyD88, for example a TRR.

The inhibitory MyD88 molecule may be a MyD88 molecule that is less able than MyD88, preferably substantially unable, to bind to a DD, for example the DD of MyD88 or of IRK or TRAF-6. For example, the inhibitory MyD88 may be less able than MyD88, preferably substantially unable, to dimerise via the DD. The inhibitory MyD88 molecule may be a mutated MyD88 molecule, for example a MyD88 molecule that is mutated in the DD, for example with a non-conservative mutation. For example, it may be mutated at the position equivalent to Phe56 of full length mouse MyD88, for example to Asn. It may be the mutated MyD88 molecule termed MyD88lpr (5) in which the N-terminal 53 amino acids of MyD88 are also absent. MyD88lpr has a point mutation (F56N; mouse sequence numbering) when compared with wild-type MyD88, for example mouse wild-type MyD88. This point mutation is in the DD and prevents dimerisation of the DD (5). The mutation corresponds to the lpr$^{cp}$ mutation known to abolish cytotoxic signalling of Fas, probably by disrupting the conformation of the DD domain (Nagata (1994) *Semin Immunol* 6, 3-8; Huang, et al (1996) *Nature* 384, 638-641).

The constructs for the wild-type MyD88 and dominant negative MyD88 (MyD88-lpr) has been published (Burns K. et al. *J Biol Chem* 1998) but MyD88-lpr is wrongly described as a single amino acid mutation in its death domain, where Phe$^{56}$ is mutated to Asn. This mutation corresponds to the lpr$^{cp}$ mutation present in the death domain of Fas ligand which abolishes its downstream signalling by disrupting the conformation of the death domain. Actually, in addition to the point mutation there is a deletion in its N-terminal domain of 53 amino acids (1-159 base pairs of the genebank sequence are missing). This deletion results in part of the death domain missing.

The inhibitory MyD88 may be a truncated version of MyD88, for example a MyD88 molecule in which all or part of the domain termed the Death Domain is deleted. An inhibitory MyD88 molecule may be incapable or less capable of binding to a Death Domain than a wild-type MyD88 molecule.

It is preferred that the inhibitory MyD88 comprises a functional Toll domain, ie a Toll domain that is capable of interacting with a Toll domain, for example the Toll domain of a wild-type MyD88, for example wild-type human or mouse MyD88 or a TRR. It is preferred that the inhibitory MyD88 comprises the full-length MyD88 Toll domain. A full-length Toll domain may be necessary for Toll-Toll domain interaction. Whilst not intending to be bound by theory, the inhibitory MyD88 may then bind to the Toll domain of a Toll receptor molecule and thereby inhibit binding of a wild-type MyD88 to the Toll receptor, thereby inhibiting signalling from that receptor molecule.

Methods of measuring protein-protein interactions (and their enhancement or disruption) will be well known to those skilled in the art. Suitable methods of measuring DD and Toll-Toll interactions are also described in (5). Suitable methods may include, for example, yeast two-hybrid interactions, co-purification, ELISA, co-immunoprecipitation, fluorescence resonance energy transfer (FRET) techniques and surface plasmon resonance methods. Thus, a MyD88 molecule may be considered capable of binding to or interacting with a DD or Toll domain if an interaction may be detected between the said MyD88 polypeptide and a polypeptide comprising a DD or Toll domain by ELISA, co-immunoprecipitation or surface plasmon resonance methods or by a yeast two-hybrid interaction or copurification method. The preferred method is surface plasmon resonance.

The inhibitor or enhancer may be a peptidomimetic compound, for example a peptidomimetic compound corresponding to a polypeptide inhibitor or enhancer discussed above.

The term "peptidomimetic" refers to a compound that mimics the conformation and desirable features of a particular peptide as a therapeutic agent, but that avoids potentially undesirable features. For example, morphine is a compound which can be orally administered, and which is a peptidomimetic of the peptide endorphin.

Therapeutic applications involving peptides may be limited, due to lack of oral bioavailability and to proteolytic degradation. Typically, for example, peptides are rapidly degraded in vivo by exo- and endopeptidases, resulting in generally very short biological half-lives. Another deficiency of peptides as potential therapeutic agents is their lack of bioavailability via oral administration. Degradation of the peptides by proteolytic enzymes in the gastrointestinal tract is likely to be an important contributing factor. The problem is, however, more complicated because it has been recognised that even small, cyclic peptides which are not subject to rapid metabolite inactivation nevertheless exhibit poor oral bioavailability. This is likely to be due to poor transport across the intestinal membrane and rapid clearance from the blood by hepatic extraction and subsequent excretion into the intestine. These observations suggest that multiple amide bonds may interfere with oral bioavailability. It is thought that the peptide bonds linking the amino acid residues in the peptide chain may break apart when the peptide drug is orally administered.

There are a number of different approaches to the design and synthesis of peptidomimetics. In one approach, such as disclosed by Sherman and Spatola, *J. Am. Chem. Soc.*, 112: 433 (1990), one or more amide bonds have been replaced in an essentially isoteric manner by a variety of chemical functional groups. This stepwise approach has met with some success in that active analogues have been obtained. In some instances, these analogues have been shown to possess longer biological half-lives than their naturally-occurring counterparts. Nevertheless, this approach has limitations. Successful replacement of more than one amide bond has been rare. Consequently, the resulting analogues have remained susceptible to enzymatic inactivation elsewhere in the molecule. When replacing the peptide bond it is preferred that the new linker moiety has substantially the same charge distribution and substantially the same planarity as a peptide bond.

Retro-inverso peptidomimetics, in which the peptide bonds are reversed, can be synthesised by methods known in the art, for example such as those described in Mézière et al (1997) *J Immunol*. 159 3230-3237. This approach involves making pseudopeptides containing changes involving the backbone, and not the orientation of side chains. Retro-inverse peptides, which contain NH—CO bonds instead of CO—NH peptide bonds, are much more resistant to proteolysis.

In another approach, a variety of uncoded or modified amino acids such as D-amino acids and N-methyl amino acids have been used to modify mammalian peptides. Alternatively, a presumed bioactive conformation has been stabilised by a covalent modification, such as cyclisation or by incorporation of γ-lactam or other types of bridges. See, eg. Veber et al, *Proc. Natl. Acad. Sci. USA*, 75:2636 (1978) and Thursell et al, *Biochem. Biophys. Res. Comm.*, 111:166 (1983).

A common theme among many of the synthetic strategies has been the introduction of some cyclic moiety into a peptide-based framework. The cyclic moiety restricts the conformational space of the peptide structure and this frequently results in an increased affinity of the peptide for a particular biological receptor. An added advantage of this strategy is that the introduction of a cyclic moiety into a peptide may also result in the peptide having a diminished sensitivity to cellular peptidases.

One approach to the synthesis of cyclic stabilised peptidomimetics is ring closing metathesis (RCM). This method involves steps of synthesising a peptide precursor and contacting it with a RCM catalyst to yield a conformationally restricted peptide. Suitable peptide precursors may contain two or more unsaturated C—C bonds. The method may be carried out using solid-phase-peptide-synthesis techniques. In this embodiment, the precursor, which is anchored to a solid support, is contacted with a RCM catalyst and the product is then cleaved from the solid support to yield a conformationally restricted peptide.

The methods of the invention may be used to treat any mammal such as human, dog, cat, horse, cow and the like. Preferably, the methods are used to treat a human patient.

A further aspect of the invention provides a method of identifying a compound which is an inhibitor of antigen presentation comprising the step of identifying a compound that is capable of modulating, preferably activating TRR signalling, for example MyD88 signalling, in an antigen-presenting cell such as a dendritic cell, or precursor of an APC. Preferably, modulation, for example activation, of TRR signalling may be detected by observing a change in the interaction of MyD88 with an interacting molecule, for example polypeptide, for example an increase of MyD88 binding to a TRR.

A further aspect of the invention provides a method of identifying a compound which is an enhancer of antigen presentation comprising the step of identifying a compound that is capable of modulating, preferably inhibiting TRR signalling, for example MyD88 signalling, (or enhancing Mal, TIRAP or TollIP signalling) in an antigen-presenting cell, such as a dendritic cell, or precursor of an APC. The TRR signalling to be inhibited is signalling which inhibits DC maturation or function, as indicated above. Preferably, inhibition of TRR signalling may be detected by observing a change in the interaction of MyD88 with an interacting molecule, for example polypeptide, for example a decrease of MyD88 binding to a TLR.

A change in IRAK or MAP kinase activity may be observed. IRAK activity may be increased by MyD88lpr.

A further aspect of the invention provides a method of identifying a compound which is an inhibitor or enhancer of antigen presentation, for example by an APC such as a DC, comprising the step of exposing a test compound to MyD88 or to an APC binding partner of MyD88 (ie binding partner of MyD88 found in an APC such as a DC, or precursor thereof) and determining whether the compound is capable of binding to MyD88 or an APC binding partner of MyD88. A compound capable of so binding is selected. Preferably the method further comprises the step of determining whether the compound inhibits or promotes binding of MyD88 to an APC binding partner of MyD88 and selecting a compound that is capable of inhibiting or promoting such binding. The compound may be further tested, for example by observing its effect on DC maturation or antigen presentation. The method may also comprise the step of determining whether the compound binds to a mutant of MyD88, for example MyD88 lacking a functional Toll domain, or lacking a functional DD.

The binding partner may be a TRR or a polypeptide comprising a DD, as discussed above. Methods of identifying a MyD88 binding partner in an APC such as a DC will be well known to those skilled in the art, and include co-precipitation and yeast two-hybrid methods and surface plasmon resonance and FRET.

A further aspect of the invention provides a method of identifying a compound which is an inhibitor or enhancer of antigen presentation, for example by an APC such as a DC, comprising the step of exposing a test compound to a TRR interacting molecule (adaptor molecule), for example Mal or TIRAP or TollIP, or to an APC binding partner of such an adaptor molecule (ie binding partner of the adaptor molecule found in an APC such as a DC, or precursor thereof) and determining whether the compound is capable of binding to the adaptor molecule (for example Mal or TIRAP or TollIP) or an APC binding partner of the adaptor molecule. A compound capable of so binding is selected. Preferably the method further comprises the step of determining whether the compound inhibits or promotes binding of the adaptor molecule to an APC binding partner of the adaptor molecule and selecting a compound that is capable of inhibiting or promoting such binding. The compound may be further tested, for example by observing its effect on DC maturation or antigen presentation. The method may also comprise the step of determining whether the compound binds to a mutant of the adaptor molecule, for example a mutant of, for example, TIRAP or Mal or TollIP, lacking a functional Toll domain, or lacking a functional DD.

A further aspect of the invention provides the use of MyD88 (or another adaptor molecule, for example TIRAP or Mal or TollIP) or an APC binding partner of MyD88 or other adaptor molecule in a method of identifying an inhibitor or enhancer of antigen presentation, for example by DC.

The compound may be a drug-like compound or lead compound for the development of a drug-like compound for each of the above methods of identifying a compound. It will be appreciated that the said methods may be useful as screening assays in the development of pharmaceutical compounds or drugs, as well known to those skilled in the art.

The term "lead compound" is similarly well known to those skilled in the art, and may include the meaning that the compound, whilst not itself suitable for use as a drug (for example because it is only weakly potent against its intended target, non-selective in its action, unstable, difficult to synthesise or has poor bioavailability) may provide a starting-point for the design of other compounds that may have more desirable characteristics.

A further aspect of the invention provides a compound identified or identifiable by a screening method of the invention, ie as provided by the preceding three aspects of the invention. A still further aspect of the invention provides a compound identified or identifiable by a screening method of the invention for use in medicine. A further aspect of the invention provides an APC binding partner of MyD88 (or Mal or TIRAP or TollIP) or mutant thereof for use in medicine. A further aspect of the invention provides the use of a compound identified or identifiable by a screening method of the invention, or an APC binding partner of MyD88 (or Mal or TIRAP or TollIP) or mutant thereof for treating a patient in need of inhibition or enhancement of antigen presentation, or in the manufacture of a medicament for treating a patient in need of inhibition or enhancement of antigen presentation.

Preferably the APC-binding partners of MyD88 (or Mal or TIRAP or TollIP) are DC-binding partners of MyD88.

A further aspect of the invention provides an inhibitor of Toll-related receptor (TRR) signalling for use in medicine. A further aspect of the invention provides an enhancer of Toll-related receptor (TRR) signalling for use in medicine, for example for treating a patient in need of inhibition or enhancement of antigen presentation.

A further aspect of the invention provides an enhancer or inhibitor of a signalling step (occuring in an APC such as a DC) directly involving MyD88 for use in medicine, for example for treating a patient in need of inhibition or enhancement of antigen presentation.

Preferences for the said signalling inhibitors and enhancers are as indicated above. Preferably the signalling inhibitor is a dominant negative mutant of MyD88, for example MyD88lpr or MyD88 lacking a death domain, or a compound that is capable of binding to MyD88, preferably a small molecule or drug-like molecule, as discussed above. The signalling inhibitor or enhancer may also be TIRAP or Mal or TollIP or a fragment, fusion or variant thereof, as discussed above.

As indicated above, it will be appreciated that the signalling (for example TRR or MyD88 signalling) inhibitor or enhancer (or compound identified or identifiable by a screening method of the invention) may be supplied to the cell by means of expression (ie synthesis) of the signalling inhibitor or enhancer (or compound) in the cell, for example expression of the TRR signalling inhibitor or enhancer from a recombinant polynucleotide (ie a recombinant polynucleotide capable of expressing the TRR signalling inhibitor or enhancer) present in the cell. It will be appreciated that such supply by means of expression of the signalling inhibitor or enhancer or compound in the target cell may be beneficial; for example, such supply may facilitate targeting of the signalling inhibitor or enhancer to the desired cell. It may also facilitate temporally-extended presence of the signalling inhibitor or enhancer or the ability to supply the signalling inhibitor or enhancer to the cell.

It will be appreciated that it may be desirable to supply both a modulator, for example signalling inhibitor as defined above, (or compound identified or identifiable by a screening method of the invention which is an enhancer of antigen presentation) and an antigen to the desired cell. It is preferred that either the signalling inhibitor/compound or antigen, preferably both, are supplied to the desired cell by means of expression in the desired cell.

Similarly, it may be desirable to supply both a signalling enhancer (or compound identified or identifiable by a screening method of the invention which is an inhibitor of antigen presentation) and an antigen to the desired cell. It is preferred that either the signalling enhancer/compound or antigen, preferably both, are supplied to the desired cell by means of expression in the desired cell.

A further aspect of the invention provides a recombinant polynucleotide encoding a signalling inhibitor or enhancer (or an APC binding partner of MyD88 or compound identified or identifiably by a screening method of the invention), for example a MyD88 polypeptide (for example a constitutively active MyD88 polypeptide or dominant negative mutant MyD88 polypeptide) or Mal or TIRAP or TollIP polypeptide for use in medicine. The signalling inhibitor or enhancer is preferably a dominant negative MyD88 polypeptide as defined above. The recombinant polynucleotide is preferably capable of expressing the signalling inhibitor or enhancer in an APC such as a dendritic cell, or an APC precursor.

It is preferred that the recombinant polynucleotide encodes a modulator of signalling pathways such as an inhibitor and an antigen that it is desired to have presented by an APC. Thus, the recombinant polynucleotide may comprise a portion encoding a signalling modulator, such as an inhibitor, and a portion encoding an antigenic molecule. Alternatively, the antigenic molecule may be encoded on a separate polynucleotide molecule; this is less preferred. The signalling molecule and antigen may be transcribed from a single promoter with an internal ribosome entry site (IRES) for the second coding sequence. Alternatively, the signalling molecule and antigen may be transcribed from separate promoters.

The antigenic molecule may comprise more than one copy of one or more epitopes. For example, it may comprise a single copy of a single epitope-forming amino acid sequence, for example a sequence of between about 8 and 30 amino acids, preferably about 10 to 18 amino acids, still more preferably about 15 amino acids in length. It may comprise multiple copies of such an epitope-forming sequence, or single or multiple copies of at least two different epitope-forming sequences. The antigenic sequences may be concatenated to form a domain-like structure, or may be disposed at different points in a carrier polypeptide. The polynucleotide may encode one or several different antigenic molecules or many, each of which may have one or more antigenic portions or epitopes.

The use of recombinant polyepitope vaccines for the delivery of multiple CD8 CTL epitopes is described in Thomson et al (1996) *J. Immunol.* 157, 822-826 and WO 96/03144, both of which are incorporated herein by reference. In relation to the present invention, it may be desirable to include in a single vaccine, a peptide (or a nucleic acid encoding a peptide) wherein the peptide includes, in any order, one or more antigenic amino acid sequences (for example each of between about 8 and 18 amino acids in length), for example derived from a tumour-associated antigen, and a CD4 T cell-stimulating epitope (such as from tetanus toxoid). Such "bead-on-a-string" vaccines are typically DNA vaccines.

For example, the antigenic molecule may comprise an epitope present on transformed or cancerous cells (ie a tumour-associated antigen or epitope, for example the MAGE-1 antigen produced by a high proportion of human melanoma tymours (van der Bruggen et al (1991) *Science* 254, 1643)). Alternatively, it may comprise an epitope present on a pathogenic organism, for example a virus, or on a cell (preferably a human cell) infected by a pathogenic organism, for example a virally-infected cell.

The epitope may be a T-cell epitope ie an epitope that is capable of inducing a T-cell response (TH-1 response), eg. a T-helper cell response preferably a CD8+ cytotoxic T-cell response, but alternatively a CD4+ helper T-cell response (TH-2 response) as well known to those skilled in the art. A cytotoxic T-cell response may be undesirable in certain cases, for example when the antigen is a mycobacterial antigen (for example *Mycobacterium tuberculosis* or *M. leprae* antigen).

A signalling enhancer as herein described may be capable of modulating the immune response to an antigen such that the TH1/TH2 balance of the immune response is altered, preferably becoming more TH1 and less TH2. A TH2 response may be associated with allergy.

It is preferred if the cancer antigen is, or has at least one epitope present in, any of the following:
i) normal cellular proteins that are expressed at abnormally high levels in tumours; eg cyclin D1 in a variety of tumours; cyclin E in breast cancer; mdm 2 in a variety of tumours; EGF-R, erb-B2, erb-B3, FGF-R, insulin-like growth factor receptor, Met, myc, p53 and BCL-2 are all expressed in various tumours.
ii) normal cellular proteins that are mutated in tumours; eg Ras mutations in a variety of tumours; p53 mutations in a variety of tumours; BCR/ABL translocation in CML and ALL; CSF-1 receptor mutations in AML and MDS; APC mutations in colon cancer; RET mutations in MEN2A, 2B and FMTC; EGFR mutations in gliomas; PML/RARA translocation in PML; E2A-PBX1 translocation in pre B leukaemias and in childhood acute leukaemias.
iii) virally encoded proteins in tumours associated with viral infection; eg human papilloma virus proteins in cervical cancer; Epstein-Barr virus proteins in B cell lymphomas and Hodgkin's lymphoma; HTLV-1 proteins in adult T cell leukaemia; hepatitis B and C virus proteins in hepatocellular carcinoma; herpes-like virus proteins in Kaposi's sarcoma.
iv) HIV encoded proteins in HIV infected patients.

Thus, the above cancer-associated antigens can be divided into three main categories: (i) normal self antigens expressed at high levels in tumour cells; (ii) mutated self antigens expressed in tumour cells; (iii) viral antigens expressed in tumours associated with viral infection. Category (i) is preferred.

Three subtypes are included in category (i):
a) normal cellular proteins that are overexpressed;
b) proteins that are expressed in a tissue-specific fashion in normal cells but also in tumours; and
c) proteins that are embryonic antigens, silent in most adult tissues but aberrantly expressed in tumours.

Examples of b) and c) are:
b) tissue-specific differentiation antigens as targets for tumour-reactive CTL such as GATA-1, IKAROS, SCL (expressed in the haematopoietic lineage and in leukaemias); and immunoglobulin constant regions (for treatment of multiple myeloma); and
c) Wilms-tumour antigen 1 (WT1) for treatment of leukaemias and Wilms tumour and carcinoembryonic antigens (CEA a foetal protein) for liver and intestinal tumours.

In one embodiment, the cancer-associated antigen may be provided by a crude extract of a tumour sample.

Overexpression of oncogene-encoded proteins in human tumours and mutated oncogenes expressed in human tumours are described in Stauss & Dahl (1995) *Tumour Immunology*, Dalgleish/Browning, Chapter 7. incorporated herein by reference.

Thus, it is preferred if the patient to be treated has cancer; more preferably any one of breast cancer; bladder cancer; lung cancer; prostate cancer; thyroid cancer; leukaemias and lymphomas such as CML, ALL, AML PML; colon cancer; glioma; seminoma; liver cancer; pancreatic cancer; bladder cancer; renal cancer; cervical cancer; testicular cancer; head and neck cancer; ovarian cancer; neuroblastoma and melanoma.

CML is chronic myelocytic leukaemia; ALL is acute lymphoblastic leukaemia; AML is acute myelocytic leukaemia; and PML is pro-myelocytic leukaemia.

Alternatively, the patient may have or be at risk of any disease caused by a pathogen, particularly a bacterium, yeast, virus, trypanosome and the like. It is preferred if the disease is caused by a chronic infection with a pathogen. It is also preferred if the pathogen is one which is not readily cleared by the host immune system.

It is preferred if the disease is a viral infection; more preferably a disease caused by any one of HIV, papilloma virus, Epstein-Barr virus, HTLV-1, hepatitis B virus, hepatitis C virus, herpes virus or any virus that causes chronic infection. It is particularly preferred if the virus is HIV.

Abnormally elevated amounts of a hormone produced by cells occur in some diseases such as certain types of thyroid disease. Thus, the method of the invention may be used to promote ablation of cells producing the elevated amounts of the hormone. The antigen may be the hormone the biosynthetic enzymes involved in synthesis of the hormone, which may be overproduced by the cell.

Patients with a bacterial infection, particularly an infection that causes chronic infection may also be usefully treated. The bacterial infection may be an intracellular infection. Thus, the method may be useful in treating tuberculosis.

The method may also be used to treat malaria.

Other patients who may benefit from enhancement or stimulation of antigens presentation include those with prion-related diseases such as spongiform encephalopathies. The method of enhancing or stimulating antigen presentation may be used to treat (including prophylactically) diseases or conditions characterised by aberrant types and/or abberantly high levels of (harmful) molecules, for example polypeptides, in the body, for example, levels of inflammatory mediators (for example, cytokines) associated with chronic inflammation; breakdown products of cells or connective tissue matrix, for example fibronectrin fragments; β-amyloid polypeptide (associated with Alzheimer's disease). Stimulating an immune response against such molecules may aid removal of the molecules from the body, thereby helping in resolution or prevention of the condition.

A patient in need of inhibition of antigen presentation may be a patient with or at risk of an autoimmune disease or allergy, or a patient in receipt of, or intended to be in receipt of, transplanted tissue, ie a patient in which inhibition of rejection of the transplanted tissue is required. Appropriate antigens will be known to those skilled in the art.

Autoimmune diseases that may be treated by this method of the invention include rheumatoid arthritis, type I diabetes, multiple sclerosis, Crohn's disease, Hashimoto's thyroiditis, coeliac disease, myasthenia gravis, pemphigus vulgaris, systemic lupus erythromatosus, and Graves disease. Allergies which may be treatable by the method described herein include allergies to the following allergens: Fel d 1 (the feline skin and salivary gland allergen of the domestic cat *Felis domesticus*—the amino acid sequence of which is disclosed in WO 91/06571), Der p I, Der p II, Der FI or Der fII (the major protein allergens from the house dust mite dermatophagoides—amino acid sequences disclosed in WO 94/24281).

The invention is applicable substantially to any allergy, including those caused by allergens present in any of the following: grass, tree and weed (including ragweed) pollens; fungi and moulds; foods eg fish, shellfish, crab lobster, peanuts, nuts, wheat gluten, eggs and milk; stinging insects eg bee, wasp and hornet and the chironomidae (non-biting midges); spiders and mites, including the house dust mite; allergens found in the dander, urine, saliva, blood or other bodily fluid of mammals such as cat, dog, cows, pigs, sheep, horse, rabbit, rat, guinea pig, mouse and gerbil; airbourne particulates in general; latex; and protein detergent additives.

Allergies to proteins from the following insects may also be treated: housefly, fruit fly, sheep blow fly, screw worm fly, grain weevil, silkworm, honeybee, non-biting midge larvae, bee moth larvae mealworm, cockroach and larvae of *Tenibrio molitor* beetle.

A further aspect of the invention comprises a kit of parts, composition or a chimaeric molecule, for example chimaeric polypeptide, comprising a signalling inhibiting or enhancing portion (which may be a polynucleotide encoding an antigenic molecule) and an antigenic portion (which may be a polynucleotide encoding an antigenic molecule), as defined above. Either or both portions may further comprise a translocating portion and/or a cell binding portion. The cell binding portion is preferably capable of binding to a dendritic cell or precursor thereof. The translocating portion may aid in internalisation of the molecule or at least the antigenic portion and preferably the signalling inhibiting or enhancing portion. Thus, exogenously applied peptides may be linked to a HIV tat peptide. This may direct them into the MHC Class I pathway for presentation by CTL (see, for example, Kim et al (1997) *J. Immunol.* 159, 1666-1668. Chimaeric molecules which may be adapted in accordance with the present invention are described in WO95/31483.

Dendritic cells may be characterised by expression of the. CD80, CD86. CD40, CD1a, HLA-DR and/or CD83 cell surface molecules. Immature dendritic cells may be $CD34^+$ or $CD14^+$. Thus, the cell binding portion may be capable of binding to one or more of these cell surface molecules (for example, an antibody capable of binding to such a molecule). CD1a and CD83 are preferred for targeting DCs.

Polypeptides in which one or more of the amino acid residues are chemically modified, before or after the polypeptide is synthesised, may be used as antigen providing that the function of the polypeptide, namely the production of a specific immune response in vivo, remains substantially unchanged. Such modifications include forming salts with acids or bases, especially physiologically acceptable organic or inorganic acids and bases, forming an ester or amide of a terminal carboxyl group, and attaching amino acid protecting groups such as N-t-butoxycarbonyl. Such modifications may protect the polypeptide from in vivo metabolism.

The epitope(s) (for example epitope-forming amino acid sequences) may be present as single copies or as multiples, for example tandem repeats. Such tandem or multiple repeats may be sufficiently antigenic themselves to obviate the use of a carrier. It may be advantageous for the polypeptide to be formed as a loop, with the N-terminal and C-terminal ends joined together, or to add one or more Cys residues to an end to increase antigenicity and/or to allow disulphide bonds to be formed. If the epitope, for example epitope-forming amino acid sequence, is covalently linked to a carrier, preferably a polypeptide, then the arrangement is preferably such that the epitope-forming amino acid sequence forms a loop.

According to current immunological theories, a carrier function should be present in any immunogenic formulation in order to stimulate, or enhance stimulation of, the immune system. The epitope(s) as defined above in relation to the preceding aspects of the invention may be associated, for example by cross-linking, with a separate carrier, such as serum albumins, myoglobins, bacterial toxoids and keyhole limpet haemocyanin. More recently developed carriers which induce T-cell help in the immune response include the hepatitis-B core antigen (also called the nucleocapsid protein), presumed T-cell epitopes such as Thr-Ala-Ser-Gly-Val-Ala-Glu-Thr-Thr-Asn-Cys, beta-galactosidase and the 163-171 peptide of interleukin-1. The latter compound may variously be regarded as,a carrier or as an adjuvant or as both.

Alternatively, several copies of the same or different epitope may be cross-linked to one another; in this situation there is no separate carrier as such, but a carrier function may be provided by such cross-linking. Suitable cross-linking agents include those listed as such in the Sigra and Pierce catalogues, for example glutaraldehyde, carbodiimide and succinimidyl 4-(N-maleimidomethyl)cyclohexane-1-carboxylate, the latter agent exploiting the —SH group on the C-terminal cysteine residue (if present). Any of the conventional ways of cross-linking polypeptides may be used, such as those generally described in O'Sullivan et al *Anal. Biochem.* (1979) 100, 100-108. For example, the first portion may be enriched with thiol groups and the second portion reacted with a bifunctional agent capable of reacting with those thiol groups, for example the N-hydroxysuccinimide ester of iodoacetic acid (NHIA) or N-succinimidyl-3-(2-pyridyldithio)propionate (SPDP), a heterobifunctional cross-linking agent which incorporates a disulphide bridge between the conjugated species. Amide and thioether bonds, for example achieved with m-maleimidobenzoyl-N-hydroxysuccinimide ester, are generally more stable in vivo than disulphide bonds.

Further useful cross-linking agents include S-acetylthioglycolic acid N-hydroxysuccininide ester (SATA) which is a thiolating reagent for primary amines which allows deprotection of the sulphydryl group under mild conditions (Julian et al (1983) *Anal. Biochem.* 132, 68), dimethylsuberimidate dihydrochloride and N,N'-o-phenylenedimaleimide.

If the polypeptide is prepared by expression of a suitable nucleotide sequence in a suitable host, then it may be advantageous to express the polypeptide as a fusion product with a peptide sequence which acts as a carrier. Kabigen's "Ecosec" system is an example of such an arrangement.

Epitopes from different biological sources (for example different pathogenic organisms) may be linked to other antigens to provide a dual effect.

By epitopes is included mimotopes, as well known to those skilled in the art.

Suitable vectors or constructs which may be used to prepare a suitable recombinant polypeptide or polynucleotide will be known to those skilled in the art.

A polynucleotide capable of expressing the required polypeptide or polypeptides may be prepared using techniques well known to those skilled in the art.

Preferably, the polynucleotide is capable of expressing the polypeptide(s) in the patient. The polypeptide(s), for example TRR signalling inhibitor or enhancer, or antigen, as appropriate, may be expressed from any suitable polynucleotide (genetic construct) as is described below and delivered to the patient. Typically, the genetic construct which expresses the polypeptide comprises the said polypeptide coding sequence operatively linked to a promoter which can express the transcribed polynucleotide (eg mRNA) molecule in a cell of the patient, which may be translated to synthesise the said polypeptide. Suitable promoters will be known to those skilled in the art, and may include promoters for ubiquitously expressed, for example housekeeping genes or for tissue-selective genes, depending upon where it is desired to express the said polypeptide (for example, in dendritic cells or precursors thereof). Preferably, a dendritic cell or dendritic precursor cell-selective promoter is used, but this is not essential, particularly if delivery or uptake of the polynucleotide is targeted to the selected cells, eg dendritic cells or precursors. Dendritic cell-selective promoters may include the CD83 or CD36 promoters.

The nucleic acid sequence capable of expressing the polypeptide(s) is preferably operatively linked to regulatory elements necessary for expression of said sequence.

"Operatively linked" refers to juxtaposition such that the normal function of the components can be performed. Thus, a coding sequence "operatively linked" to regulatory elements refers to a configuration wherein the nucleic acid sequence encoding the inhibitor (or inducer, which is useful as described in more detail below), of NF-κB can be expressed under the control of the regulatory sequences.

"Regulatory sequences" refers to nucleic acid sequences necessary for the expression of an operatively linked coding sequence in a particular host organism. For example, the regulatory sequences which are suitable for eukaryotic cells are promoters, polyadenylation signals, and enhancers.

"Vectors" means a DNA molecule comprising a single strand, double strand, circular or supercoiled DNA. Suitable vectors include retrovinises, adenoviruses, adeno-associated viruses, pox viruses and bacterial plasmids. Retroviral vectors are retroviruses that replicate by randomly integrating their genome into that of the host. Suitable retroviral vectors are described in WO 92/07573.

Adenovirus is a linear double-standard DNA Virus. Suitable adenoviral vectors are described in Rosenfeld et al, Science, 1991, Vol. 252, page 432.

Adeno-associated viruses (AAV) belong to the parvo virus family and consist of a single strand DNA or about 4-6 KB.

Pox viral vectors are large viruses and have several sites in which genes can be inserted. They are thermostable and can be stored at room temperature. Safety studies indicate that pox viral vectors are replication-defective and cannot be transmitted from host to host or to the environment.

Targeting the vaccine to specific cell populations, for example antigen presenting cells, may be achieved, for example, either by the site of injection, use of targeting vectors and delivery systems, or selective purification of such a cell population from the patient and ex vivo administration of the peptide or nucleic acid (for example dendritic cells may be sorted as described in Zhou et al (1995) *Blood* 86, 3295-3301; Roth et al (1996) *Scand. J. Immunology* 43, 646-651). In addition, targeting vectors may comprise a tissue- or tumour-selective promoter which directs expression of the antigen at a suitable place.

Although the genetic construct can be DNA or RNA it is preferred if it is DNA.

Preferably, the genetic construct is adapted for delivery to a human cell.

Means and methods of introducing a genetic construct into a cell in or removed from an animal body are known in the art. For example, the constructs of the invention may be introduced into the cells by any convenient method, for example methods involving retroviruses, so that the construct is inserted into the genome of the (dividing) cell. Targeted retroviruses are available for use in the invention; for example, sequences conferring specific binding affinities may be engineered into pre-existing viral env genes (see Miller & Vile (1995) *Faseb J.* 9, 190-199 for a review of this and other targeted vectors for gene therapy).

Preferred retroviral vectors are lentiviral vectors such as those described in Verma & Somia (1997) *Nature* 389, 239-242.

It will be appreciated that retroviral methods, such as those described below, may only be suitable when the cell is a dividing cell. For example, in Kuriyama et al (1991) *Cell Struc. and Func.* 16, 503-510 purified retroviruses are administered. Retroviral DNA constructs which encode the desired polypeptide(s) may be made using methods well known in the art. To produce active retrovirus from such a construct it is usual to use an ecotropic psi2 packaging cell line grown in Dulbecco's modified Eagle's medium (DMEM) containing 10% foetal calf serum (FCS). Transfection of the cell line is conveniently by calcium phosphate co-precipitation, and stable transformants are selected by addition of G418 to a final concentration of 1 mg/ml (assuming the retroviral construct contains a neo® gene). Independent colonies are isolated and expanded and the culture supernatant removed, filtered through a 0.45 μm pore-size filter and stored at −70° C. For the introduction of the retrovirus into the target cells, it is convenient to inject directly retroviral supernatant to which 10 μg/ml Polybrene has been added. The injection may be made into the area in which the target cells are present, for example subcutaneously.

Other methods involve simple delivery of the construct into the cell for expression therein either for a limited time or, following integration into the genome, for a longer time. An example of the latter approach includes liposomes (Näs- sander et al (1992) *Cancer Res.* 52, 646-653). Other methods of delivery include adenoviruses carrying external DNA via an antibody-polylysine bridge (see Curiel *Prog. Med. Virol.* 40, 1-18) and transferrin-polycation conjugates as carriers (Wagner et al (1990) *Proc. Natl. Acad. Sci. USA* 87, 3410- 3414). In the first of these methods a polycation-antibody complex is formed with the DNA construct or other genetic construct of the invention, wherein the antibody is specific for either wild-type adenovirus or a variant adenovirus in which a new epitope has been introduced which binds the antibody. The polycation moiety binds the DNA via electrostatic inter- actions with the phosphate backbone. The adenovirus, because it contains unaltered fibre and penton proteins, is internalised into the cell and carries into the cell with it the DNA construct of the invention. It is preferred if the polyca- tion is polylysine.

Bacterial delivery is described in Dietrich (2000) *Antisense Nucleic Acid Drug Delivery* 10, 391-399.

The DNA may also be delivered by adenovirus wherein it is present within the adenovirus particle, for example, as described below.

In the second of these methods, a high-efficiency nucleic acid delivery system that uses receptor-mediated endocytosis to carry DNA macromolecules into cells is employed. This is accomplished by conjugating the iron-transport protein trans- ferrin to polycations that bind nucleic acids. Human transfer- rin, or the chicken homologue conalbumin, or combinations thereof is covalently linked to the small DNA-binding protein protamine or to polylysines of various sizes through a disul- fide linkage. These modified transferrin molecules maintain their ability to bind their cognate receptor and to mediate efficient iron transport into the cell. The transferrin-polyca- tion molecules form electrophoretically stable complexes with DNA constructs or other genetic constructs of the inven- tion independent of nucleic acid size (from short oligonucle- otides to DNA of 21 kilobase pairs). When complexes of transferrin-polycation and the DNA constructs or other genetic constructs of the invention are supplied to the target cells, a high level of expression from the construct in the cells is expected.

High-efficiency receptor-mediated delivery of the DNA constructs or other genetic constructs of the invention using the endosome-disruption activity of defective or chemically inactivated adenovirus particles produced by the methods of Cotten et al (1992) *Proc. Natl. Acad. Sci. USA* 89, 6094-6098 may also be used. This approach appears to rely on the fact that adenoviruses are adapted to allow release of their DNA from an endosome without passage through the lysosome, and in the presence of, for example transferrin linked to the DNA construct or other genetic construct of the invention, the construct is taken up by the cell by the same route as the adenovirus particle.

This approach has the advantages that there is no need to use complex retroviral constructs; there is no permanent modification of the genome as occurs with retroviral infec- tion; and the targeted expression system is coupled with a targeted delivery system, thus reducing toxicity to other cell types.

"Naked DNA" and DNA complexed with cationic and neutral lipids may also be useful in introducing the DNA of the invention into cells of the patient to be treated. Non-viral approaches to gene therapy are described in Ledley (1995) *Human Gene Therapy* 6, 1129-1144. Alternative targeted delivery systems are also known such as the modified aden- ovirus system described in WO 94/10323 wherein, typically, the DNA is carried within the adenovirus, or adenovirus-like, particle. Michael et al (1995) *Gene Therapy* 2, 660-668 describes modification of adenovirus to add a cell-selective moiety into a fibre protein. Mutant adenoviruses which rep- licate selectively in p53-deficient human tumour cells, such as those described in Bischoff et al (1996) *Science* 274, 373- 376 are also useful for delivering the genetic construct of the invention to a cell. Thus, it will be appreciated that a further aspect of the invention provides a virus or virus-like particle comprising a genetic construct of the invention. Other suit- able viruses or virus-like particles include HSV, AAV, vac- cinia, lentivirus and parvovirus.

Immunoliposomes (antibody-directed liposomes) are especially useful in targeting to cell types which over-express a cell surface protein for which antibodies are available, as is possible with dendritic cells or precursors, for example using antibodies to CD1, CD14 or CD83 (or other dendritic cell or precursor cell surface molecule, as indicated above). For the preparation of immuno-liposomes MPB-PE (N-[4-(p-male- imidophenyl)butyryl]-phosphatidylethanolamine) is synthe- sised according to the method of Martin & Papahadjopoulos (1982) *J. Biol. Chem.* 257, 286-288. MPB-PE is incorporated into the liposomal bilayers to allow a covalent coupling of the antibody, or fragment thereof, to the liposomal surface. The liposome is conveniently loaded with the DNA or other genetic construct of the invention for delivery to the target cells, for example, by forming the said liposomes in a solution of the DNA or other genetic construct, followed by sequential extrusion through polycarbonate membrane filters with 0.6 µm and 0.2 µm pore size under nitrogen pressures up to 0.8 MPa. After extrusion, entrapped DNA construct is separated from free DNA construct by ultracentrifugation at 80 000×g for 45 min. Freshly prepared MPB-PE-liposomes in deoxy- genated buffer are mixed with freshly prepared antibody (or fragment thereof) and the coupling reactions are carried out in a nitrogen atmosphere at 4° C. under constant end over end rotation overnight. The immunoliposomes are separated from unconjugated antibodies by ultracentrifugation at 80 000×g for 45 min. Immunoliposomes may be injected, for example intraperitoneally or directly into a site where the target cells are present, for example subcutaneously.

Preferred vectors include lentivirus vectors and adenoviral vectors, for example vectors similar to those described in Foxwell et al (2000) *Ann Rheum Dis* 59 Suppl 1, 154-59 or Bondeson et al (2000) *J Rheumatol* 27(9), 2078-2089.

It will be appreciated that it may be desirable to be able to regulate temporally expression of the polypeptide(s) (for example TRR signalling inhibitor, for example MyD88lpr) in the cell. Thus, it may be desirable that expression of the polypeptide(s) is directly or indirectly (see below) under the control of a promoter that may be regulated, for example by the concentration of a small molecule that may be adminis- tered to the patient when it is desired to activate or repress (depending upon whether the small molecule effects activa- tion or repression of the said promoter) expression of the polypeptide. It will be appreciated that this may be of particu- lar benefit if the expression construct is stable ie capable of expressing the polypeptide (in the presence of any necessary regulatory molecules) in the said cell for a period of at least one week, one, two, three, four, five, six, eight months or one or more years. A preferred construct of the invention may comprise a regulatable promoter. Examples of regulatable promoters include those referred to in the following papers: Rivera et al (1999) *Proc Natl Acad Sci USA* 96(15), 8657-62 (control by rapamycin, an orally bioavailable drug, using two separate adenovirus or adeno-associated virus (AAV) vectors, one encoding an inducible human growth hormone (hGH) target gene, and the other a bipartite rapamycin-regulated transcription factor); Magari et al (1997) *J Clin Invest* 100(11), 2865-72 (control by rapamycin); Bueler (1999) *Biol Chem* 380(6), 613-22 (review of adeno-associated viral vectors); Bohl et al (1998) *Blood* 92(5), 1512-7 (control by doxycycline in adeno-associated vector); Abruzzese et al (1996) *J Mol Med* 74(7), 379-92 (reviews induction factors e.g., hormones, growth factors, cytokines, cytostatics, irradiation, heat shock and associated responsive elements). Tetracycline—inducible vectors may also be used. These are activated by a relatively—non toxic antibiotic that has been shown to be useful for regulating expression in mammalian cell cultures. Also, steroid-based inducers may be useful especially since the steroid receptor complex enters the nucleus where the DNA vector must be segregated prior to transcription.

This system may be further improved by regulating the expression at two levels, for example by using a tissue-selective promoter and a promoter controlled by an exogenous inducer/repressor, for example a small molecule inducer, as discussed above and known to those skilled in the art. Thus, one level of regulation may involve linking the appropriate polypeptide-encoding gene to an inducible promoter whilst a further level of regulation entails using a tissue-selective promoter to drive the gene encoding the requisite inducible transcription factor (which controls expression of the polypeptide (for example MyD88 polypeptide)-encoding gene from the inducible promoters. Control may further be improved by cell-type-specific targeting of the genetic construct.

It will be appreciated that the expressed protein is preferably produced at an appropriate level relative to other proteins involved in MyD88 or TRR signalling for optimal functioning.

The methods or constructs of the invention may be evaluated in, for example, dendritic cells generated in vitro, as known to those skilled in the art, before evaluation in whole animals. The methods described in GB9930616.9, filed on 24 Dec. 1999, may also be used in the evaluation of the methods or constructs of the invention.

The genetic constructs of the invention can be prepared using methods well known in the art.

The aforementioned therapeutic molecules, for example signalling inhibitor or enhancer, (for example a MyD88 polypeptide, including a dominant negative MyD88 mutant polypeptide such as MyD88lpr) or compound, chimaeric molecule or construct of the invention or a formulation thereof, may be administered by any conventional method including oral and parenteral (eg subcutaneous or intramuscular) injection. The treatment may consist of a single dose or a plurality of doses over a period of time. It is preferred that the therapeutic molecule (for example polypeptide, chimaeric molecule, construct or formulation) is administered by injection, preferably subcutaneous injection. It will be appreciated that an inducer, for example small molecule inducer as discussed above may preferably be administered orally.

It may be desirable to locally perfuse an area comprising target cells with the suitable delivery vehicle comprising the genetic construct for a period of time. For example an organ intended for grafting may be perfused ex vivo. Additionally or alternatively, the delivery vehicle or genetic construct can be injected directly into accessible areas comprising target cells, for example subcutaneously. Methods of delivering genetic constructs, for example adenoviral vector constructs to cells of a patient will be well known to those skilled in the art.

In particular, an adoptive therapy protocol may be used or a gene gun may be used to deliver the construct to dendritic cells, for example in the skin.

Adoptive therapy protocols are described in Nestle et al (1998) *Nature Med.* 4, 328-332 and De Bruijn et al (1998) *Cancer Res.* 58, 724-731.

An adoptive therapy approach may include the steps of (1) obtaining antigen presenting cells or precursors thereof, preferably dendritic cells or precursors thereof, from the patient; (2) contacting said antigen presenting cells with a signalling inhibitor or enhancer (or compound identifiable or identified by a screening method of the invention), and optionally antigen to which an immune response is required, or chimaeric molecule or polynucleotide as discussed above, ex vivo; and (3) reintroducing the so treated antigen presenting cells into the patient.

Suitably, the dendritic cells are autologous dendritic cells which are pulsed with polypeptide(s), for example a signalling inhibitor and an antigen. T-cell therapy using autologous dendritic cells pulsed with peptides from a tumour associated antigen is disclosed in Murphy et al (1996) *The Prostate* 29, 371-380 and Tjua et al (1997) *The Prostate* 32, 272-278.

In a further embodiment the antigen presenting cells, such as dendritic cells, are contacted with a polynucleotide which encodes the signalling inhibitor or enhancer. The polynucleotide may be any suitable polynucleotide and it is preferred that it is capable of transducing the dendritic cell thus resulting in respectively activation or inhibition of antigen presentation by the antigen presenting cell.

Conveniently, the polynucleotide may be comprised in a viral polynucleotide or virus, as noted above. For example, adenovirus-transduced dendritic cells have been shown to induce antigen-specific antitumour immunity in relation to MUC1 (see Gong et al (1997) *Gene Ther.* 4, 1023-1028). Similarly, adenovirus-based systems may be used (see, for example, Wan et al (1997) *Hum. Gene Ther.* 8, 1355-1363); retroviral systems may be used (Specht et al (1997) *J. Exp. Med.* 186, 1213-1221 and Szabolcs et al (1997) *Blood* 90, 2160-2167); particle-mediated transfer to dendritic cells may also be used (Tuting et al (1997) *Eur. J. Immunol.* 27, 2702-2707); and RNA may also be used (Ashley et al (1997) *J. Exp. Med.* 186, 1177-1182).

The dendritic cells may be derived from the patient (ie autologous dendritic cells) or from a healthy individual or individuals (MHC matched or mismatched), treated in vitro as indicated above, followed by adoptive therapy, ie introduction of the so-manipulated dendritic cells in vivo, which may then activate CTL responses. By "healthy individual" we mean that the individual is generally in good health, preferably has a competent immune system and, more preferably, is not suffering from any disease which can be readily tested for, and detected.

Thus, the methods of the invention include methods of adoptive immunotherapy.

It is preferred if between about $10^3$ and $10^{11}$ APCs are administered to the patient; more preferably between $10^6$ and $10^7$ APCs. It is preferred that the APCs are DCs.

The APCs may be administered by any convenient route. It is preferred if the APCs are administered intravenously. It is also preferred if the APCs are administered locally to the site of the disease (such as a tumour or local viral or bacterial infection). Conveniently, the APCs are administered into an artery that supplies the site of the disease or the tissue where the disease is located.

The APCs may be administered subcutaneously so that they mitgrate to lymph nodes.

Preferably, the APCs are DCs.

The cells (or vaccine) may be given to a patient who is being treated for the disease by some other method. Thus, although the method of treatment may be used alone it is desirable to use it as an adjuvant therapy.

The APCs, such as DCs, or vaccine may be administered before, during or after the other therapy.

When the disease to be treated is a cancer it is preferable if the cancer has been, is being or will be treated with a conventional therapy or surgery as well as with the method of the invention. Conveniently, depending on the therapy, the cancer is treated by radiotherapy or by chemotherapy.

Cancer antigens to which an immune response may be required are disclosed in detail above.

When the disease to be treated is an infection by a pathogen it is preferable if the infection has been, is being or will be treated with a conventional therapy or surgery.

If the patient to be treated has HIV infection it is preferable if the method of the invention is used as an adjuvant to other treatment, for example treatment with a reverse transcriptase inhibitor such as AZT or 3TC or combination therapy, for example HART (highly active retroviral therapy).

When the method of the invention is used to treat a solid tumour it is preferred if the DCs or vaccine are administered as the first post-surgery treatment.

When the method of the invention is used to treat leukaemia it is preferred if the DCs or vaccine are administered after radiotherapy or chemotherapy. It is also preferred if leukaemia patients are also treated with the DCs in combination with bone marrow transplantation.

Cancer therapy, for example adoptive immunotherapy may be most effective in the control or elimination of minimal residual disease rather than in the reduction of bulk disease. It is conceivable that immunotherapy may temporarily increase the dimensions of bulk disease due to influx of cytotoxic T lymphocytes and consequences of tissue drainage. Extent and bulk of disease may be monitored following therapy but not used as a formal endpoint. Patients are followed up in the routine manner in the long term to ensure that no long term adverse events are manifest.

Further delivery or targeting strategies may include the following. Ballistic compressed air driven DNA/protein coated nanoparticle penetration (for example using a BioRad device) of cells in culture or in vivo may be used. Constructs for delivery may preferably have cell-type selective promoters.

Whilst it is possible for a therapeutic molecule as described herein, for example a signalling, enhancer or inhibitor or construct or molecule, to be administered alone, it is preferable to present it as a pharmaceutical formulation, together with one or more acceptable carriers. The carrier(s) must be "acceptable" in the sense of being compatible with the therapeutic molecule (which may be a nucleic acid or polypeptide) and not deleterious to the recipients thereof. Typically, the carriers will be water or saline which will be sterile and pyrogen free.

Nasal sprays may be useful formulations.

The formulations may conveniently be presented in unit dosage form and may be prepared by any of the methods well known in the art of pharmacy. Such methods include the step of bringing into association the active ingredient (for example, a signalling enhancer or inhibitor, construct or molecule of the invention) with the carrier which constitutes one or more accessory ingredients. In general the formulations are prepared by uniformly and intimately bringing into association the active ingredient with liquid carriers or finely divided solid carriers or both, and then, if necessary, shaping the product.

Formulations in accordance with the present invention suitable for oral administration may be presented as discrete units such as capsules, cachets or tablets, each containing a predetermined amount of the active ingredient; as a powder or granules; as a solution or a suspension in an aqueous liquid or a non-aqueous liquid; or as an oil-in-water liquid emulsion or a water-in-oil liquid emulsion. The active ingredient may also be presented as a bolus, electuary or paste.

A tablet may be made by compression or moulding, optionally with one or more accessory ingredients. Compressed tablets may be prepared by compressing in a suitable machine the active ingredient in a free-flowing form such as a powder or granules, optionally mixed with a binder (eg povidone, gelatin, hydroxypropylmethyl cellulose), lubricant, inert diluent, preservative, disintegrant (eg sodium starch glycolate, cross-linked povidone, cross-linked sodium carboxymethyl cellulose), surface-active or dispersing agent. Moulded tablets may be made by moulding in a suitable machine a mixture of the powdered compound moistened with an inert liquid diluent. The tablets may optionally be coated or scored and may be formulated so as to provide slow or controlled release of the active ingredient therein using, for example, hydroxypropylmethylcellulose in varying proportions to provide desired release profile.

Formulations suitable for topical administration in the mouth include lozenges comprising the active ingredient in a flavoured basis, usually sucrose and acacia or tragacanth; pastilles comprising the active ingredient in an inert basis such as gelatin and glycerin, or sucrose and acacia; and mouth-washes comprising the active ingredient in a suitable liquid carrier.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilised) condition requiring only the addition of the sterile liquid carrier, for example water for injections, immediately prior to use. Extemporaneous injection solutions and suspensions may be prepared from sterile powders, granules and tablets of the kind previously described.

Preferred unit dosage formulations are those containing a daily dose or unit, daily sub-dose or an appropriate fraction thereof, of an active ingredient.

It should be understood that in addition to the ingredients particularly mentioned above the formulations of this invention may include other agents conventional in the art having regard to the type of formulation in question, for example those suitable for oral administration may include flavouring agents.

It will be appreciated that the therapeutic molecule, for example inhibitor or enhancer or molecule or construct of the invention, can be delivered to the locus by any means appropriate for localised administration of a drug. For example, a solution of the said construct can be injected directly to the site or can be delivered by infusion using an infusion pump. The construct, for example, also can be incorporated into an implantable device which when placed at the desired site, permits the construct to be released into the surrounding locus.

The construct, for example, may be administered via a hydrogel material. The hydrogel is non-inflammatory and biodegradable. Many such materials now are known, including those made from natural and synthetic polymers. In a preferred embodiment, the method exploits a hydrogel which is liquid below body temperature but gels to form a shape-retaining semisolid hydrogel at or near body temperature. Preferred hydrogel are polymers of ethylene oxide-propylene oxide repeating units. The properties of the polymer are dependent on the molecular weight of the polymer and the relative percentage of polyethylene oxide and polypropylene oxide in the polymer. Preferred hydrogels contain from about 10% to about 80% by weight ethylene oxide and fiom about 20% to about 90% by weight propylene oxide. A particularly preferred hydrogel contains about 70% polyethylene oxide and 30% polypropylene oxide. Hydrogels which can be used are available, for example, from BASF Corp., Parsippany, N.J., under the tradename Pluronic®.

In this embodiment, the hydrogel is cooled to a liquid state and the construct, for example, is admixed into the liquid to a concentration of about 1 mg nucleic acid per gram of hydrogel. The resulting mixture then is applied onto the surface to be treated, for example by spraying or painting during surgery or using a catheter or endoscopic procedures. As the polymer warms, it solidifies to form a gel, and the construct diffuses out of the gel into the surrounding cells over a period of time defined by the exact composition of the gel.

The construct, for example, can be administered by means of other implants that are commercially available or described in the scientific literature, including liposomes, microcapsules and implantable devices. For example, implants made of biodegradable materials such as polyanhydrides, polyorthoesters, polylactic acid and polyglycolic acid and copolymers thereof, collagen, and protein polymers, or non-biodegradable materials such as ethylenevinyl acetate (EVAc), polyvinyl acetate, ethylene vinyl alcohol, and derivatives thereof can be used to locally deliver the construct. The construct can be incorporated into the material as it is polymerised or solidified, using melt or solvent evaporation techniques, or mechanically mixed with the material. In one embodiment, the construct (including, for example, an antisense oligonucleotide) are mixed into or applied onto coatings for implantable devices such as dextran coated silica beads, stents, or catheters.

The dose of the construct, for example, is dependent on the size of the construct and the purpose for which is it administered. In general, the range is calculated based on the surface area of tissue to be treated. The effective dose of construct may be dependent on the size of the construct and the delivery vehicle/targeting method used and chemical composition of the oligonucleotide but a suitable dose may be determined by the skilled person, for example making use of data from the animal and in vitro test systems indicated above.

The construct, for example, may be administered to the patient systemically for both therapeutic and prophylactic purposes. The construct, for example may be administered by any effective method, as described above, for example, parenterally (eg intravenously, subcutaneously, intramuscularly) or by oral, nasal or other means which permit the construct, for example, to access and circulate in the patient's bloodstream. Construct administered systemically preferably are given in addition to locally administered constrict, but also have utility in the absence of local administration.

It is believed that uptake of the nucleic acid and expression of the encoded polypeptide by dendritic cells may be the mechanism of priming of the immune response; however, dendritic cells may not be transfected but are still important since they may pick up expressed peptide from transfected cells in the tissue.

It is preferred if the vaccine, such as DNA vaccine, is administered into the muscle. It is also preferred if the vaccine is administered onto or into the skin.

A further aspect of the invention provides a vaccine effective against cancer, or cancer or tumour cells, or against a pathogenic organism or cell infected with a pathogenic organism, comprising an effective amount of a signalling enhancer or activator of antigen presentation as defined above, or a nucleic acid encoding such a signalling enhancer or activator of antigen presentation. The vaccine preferably further comprises an antigen (or polynucleotide encoding an antigen) having an epitope present on the cancer or tumour cells, or the pathogenic organism or cell infected with a pathogenic organism.

For example, the invention provides a vaccine effective against cancer, or cancer or tumour cells, or against a pathogenic organism or cell infected with a pathogenic organism, comprising an effective amount of Mal or TIRAP or TollIP or a fragment, variant or fusion thereof, or polynucleotide encoding same. The vaccine preferably further comprising an antigen (or polynucleotide encoding an antigen) having an epitope present on the cancer or tumour cells, or the pathogenic organism or cell infected with a pathogenic organism.

It is particularly preferred if the vaccine is a nucleic acid vaccine. Polynucleotide-mediated immunization therapy of cancer is described in Conry et al (1996) *Seminars in Oncology* 23, 135-147; Condon et al (1996) *Nature Medicine* 2, 1122-1127; Gong et al (1997) *Nature Medicine* 3, 558-561; Zhai et al (1996) *J. Immunol.* 156, 700-710; Graham et al (1996) *Int. J. Cancer* 65, 664-670; and Burchell et al (1996) pp 309-313 In: Breast Cancer, Advances in biology and therapeutics, Calvo et al (eds), John Libbey Eurotext, all of which are incorporated herein by reference.

Conveniently, the nucleic acid vaccine may comprise any suitable nucleic acid delivery means, as noted above. The nucleic acid, preferably DNA, may be naked (ie with substantially no other components to be administered) or it may be delivered in a liposome or as part of a viral vector delivery system.

The nucleic acid vaccine may be administered without adjuvant. The nucleic acid vaccine may also be administered with an adjuvant such as BCG or alum. Other suitable adjuvants include Aquila's QS21 STIMULON (Aquila Biotech, Worcester, Mass., USA) which is derived from saponin, mycobacterial extracts and synthetic bacterial cell wall mimics, and proprietory adjuvants such as Ribi's DETOX. Quil A, another saponin-derived adjuvant, may also be used (Superfos, Denmark). Other adjuvants such as Freund's may also be useful. It is preferred if the nucleic acid vaccine is administered without adjuvant.

A further aspect of the invention provides a pharmaceutical composition comprising a signalling inhibitor or enhancer or binding partner of MyD88 or MyD88 polypeptide or Mal, TIRAP or TollIP or compound identified or identifiable by a screening method of the invention, or polynucleotide encoding same, or composition or chimaeric molecule, vaccine or polynucleotide of the invention, and a pharmaceutically acceptable carrier.

A further aspect of the invention provides a method of killing target cells in a patient which target cells aberrantly express a first epitope, the method comprising the steps of (1) obtaining antigen presenting cells (APCs) from said patient; (2) contacting said APCs with a modulator, preferably an inhibitor, of TRR signalling in dendritic cells or with a polynucleotide or expression vector encoding an inhibitor of TRR signalling in APCs ex vivo; (3) optionally contacting said cells with the said epitope or with a polynucleotide or expression vector encoding the said epitope and (4) reintroducing the so treated APCs into the patient.

Upon reintroduction into the patient, the APCs stimulate a cytotoxic T cell response to the target cells.

Typically the APCs are dendritic cells.

The target cells may be cancer cells.

A further aspect of the invention provides a method of treating a patient with or at risk of cancer or infection with a pathogenic organism, comprising the step of supplying (1) an modulator, preferably inhibitor of TRR signalling (which may be Mal or TIRAP or TollIP (or a fragment, variant or fusion any thereof), as discussed above; and which activates APCs, for example DCs, for example enhances antigen presentation by APCs, for example DCs) or (2) an inhibitor of a signalling step directly involving MyD88, or (3) a dominant negative mutant of MyD88, to the patient or to an antigen presenting cell, or precursor cell, of the patient.

A further aspect of the invention provides a method of treating a patient with or at risk of an autoimmune disease or transplant rejection, comprising the step of supplying (1) a modulator, preferably activator of TRR signalling (which may be Mal or TIRAP or TollIP or a fragment, fusion or variant thereof, as discussed above; and which inhibits APCs, for example DCs, for example inhibits antigen presentation by APCs, for example DCs) or (2) an activator of a signalling step directly involving MyD88, or (3) MyD88, to the patient or to a an antigen presenting cell, or precursor cell, of the patient.

A further aspect of the invention provides the use of (1) a modulator, preferably inhibitor of TRR signalling (which may be Mal or TIRAP or TollIP or a fragment, variant or fusion thereof, as discussed above) or (2) an inhibitor of a signalling step directly involving MyD88, or (3) a dominant negative mutant of MyD88 (or polynucleotide encoding same) in the manufacture of a medicament for treating a patient in need of enhancement of antigen presentation and/or with or at risk of cancer or infection with a pathogenic organism.

Preferably the medicament further comprises an antigen or polynucleotide encoding an antigen. Still more preferably, the medicament comprises a polynucleotide encoding an antigen and the inhibitor molecule, or a chimaeric molecule of the invention.

The medicament may alternatively comprise an appropriate compound identifiable or identified by a screening method of the invention.

A further aspect of the invention provides the use of (1) a modulator, preferably activator of TRR signalling (which may Mal or TIRAP or TollIP or a fragment, fusion or variant thereof, as discussed above) or (2) an activator of a signalling step directly involving MyD88, or (3) MyD88 (or polynucleotide encoding same) in the manufacture of a medicament for treatment of a patient with or at risk of an autoimmune disease or transplant rejection.

Preferably the medicament further comprises an antigen or polynucleotide encoding an antigen. Still more preferably, the medicament comprises a polynucleotide encoding an antigen and the inhibitor molecule, or a chimaeric molecule of the invention.

The medicament may alternatively comprise an appropriate compound identifiable or identified by a screening method of the invention.

A further aspect of the invention provides a kit of parts or composition or chimaeric molecule, comprising (1) Mal or TollIP or TRAP or a fragment, derivative or fusion thereof (for which preferences are as indicated above) (or a polynucleotide encoding such a portion) and (2) an antigenic portion comprising or encoding an antigenic molecule. A further aspect of the invention provides the said kit of parts or composition or chimaeric molecule for use in medicine. A still further aspect of the invention provides the use of the said kit of parts or or chimaeric molecule in the manufacture of a medicament for treating a patient in need of modulation of antigen presentation.

Either or both portions in these aspects of the invention may further comprise a translocating portion and/or a cell binding portion, as discussed above.

The invention is now described by reference to the following, non-limiting, figures and examples.

FIG. 1: Structure of MyD88 comprising a toll and a death domain

MyD88 has a modular organization comprising an N-terminal death domain (DD) separated by a short linker from a C-terminal toll domain. The N-terminal DD is related to a motif of approximately 90 amino acids shared between the cytoplasmic tails of the FAS/APO1/CD95 and TNF receptors and known to mediate protein interactions with other DD sequences forming either homo- or heterodimers (Boldin M. P. et al. J Biol Chem 1995). These interactions form the foundation for building signalling complexes that can activate MAP kinases and the transcription factor NF-κB (Nagata S. Cell 1997). The MyD88 C-terminal toll domain comprises approximately 130 amino acids that is found in the expanding family of Toll-related receptors that comprise the toll-like, IL-1 and IL-18 receptors. Toll domains are also involved in protein-protein interactions. MyD88 self-associates in yeast. Full-length MyD88 and MyD88 mutants are schematically represented. The black and gray rectangles represent the death and Toll domains, respectively. MyD88 containing a point mutation, F56N, in the death domain (represented by a white circle) is referred to as MyD88-lpr. (Adapted from Burns et al 1998 JBC 273 12203).

Figures 2A, 2B:
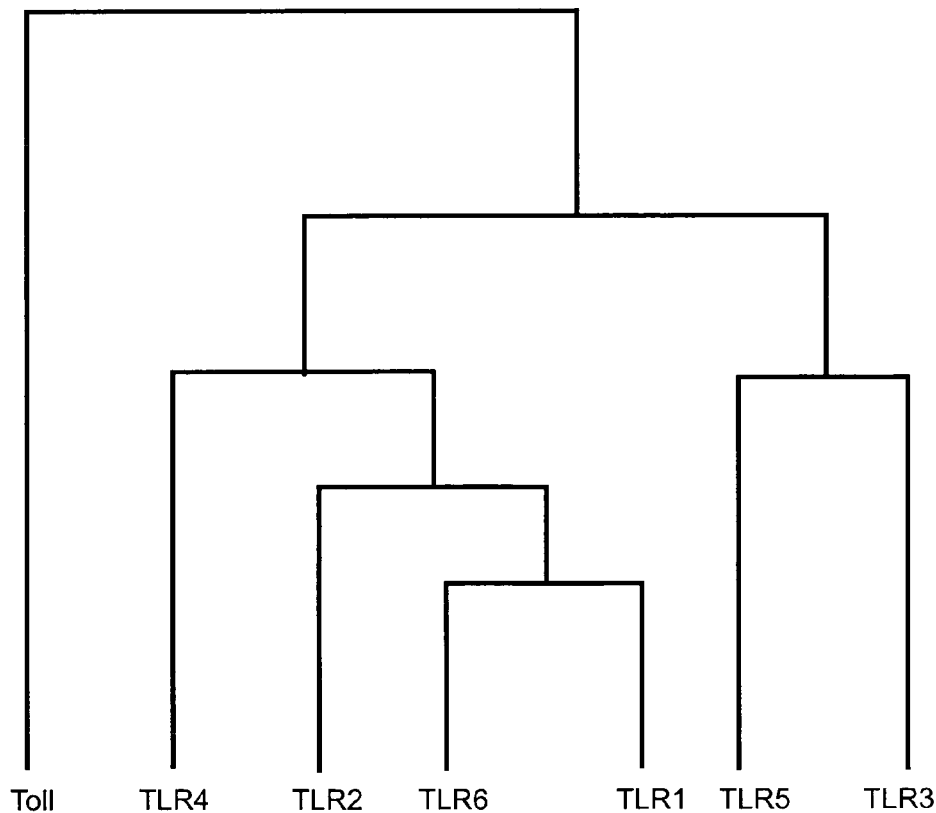

FIG. 2: Expression pattern of toll-like receptors 1-5 in cells of the immune system Recently, Muzio et al. (J Immunol 2000) have examined the expression pattern (FIG. 2A) of TLR1-5 (FIG. 2B) and found that TLR1 is ubiquitously expressed in cells of the immune system, whereas TLR2, 4 and 5 are restricted to polymorphonuclear cells, monocytes and dendritic cells. TLR3 seems to be restricted to dendritic cells.

Figure 3:
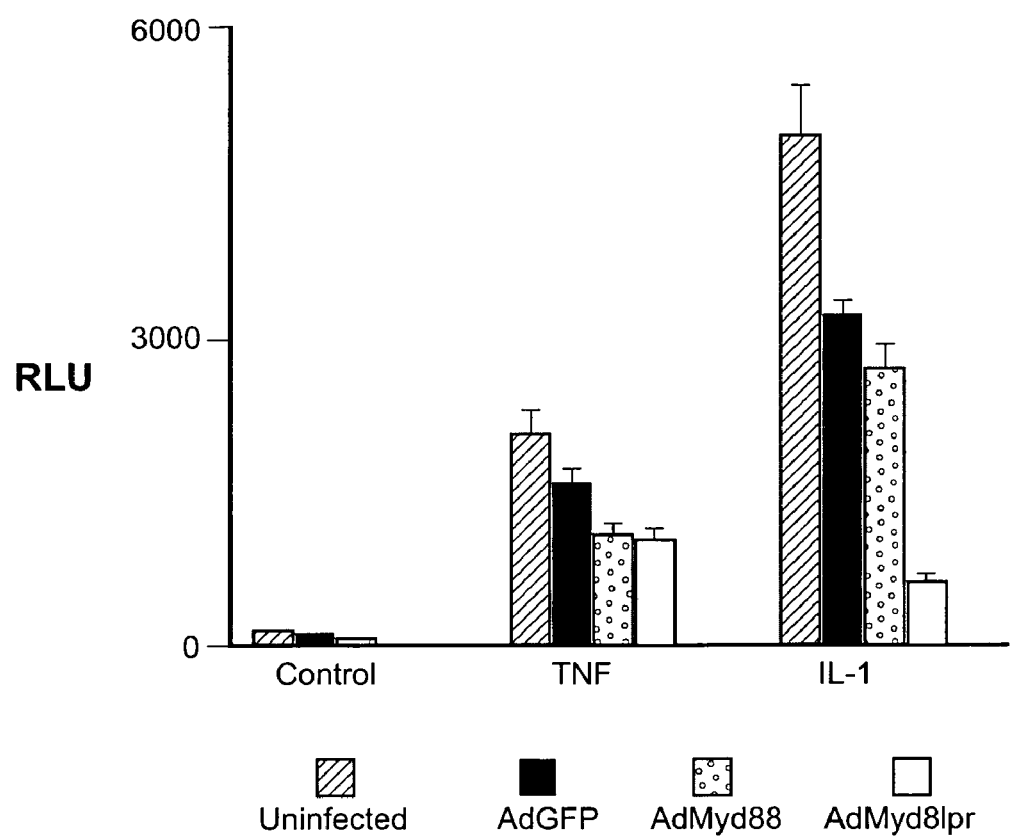

FIG. 3: Dominant negative (inhibitory) MyD88 blocks activation of an NF-κB reporter in 57A HELA cells in response to IL-1

57A HELA cells stably transfected with an NF-κB reporter gene were left uninfected or infected with a control adenovirus encoding GFP, an irrelevant protein (AdGFP), IκBα (Ad IκBα), wild-type MyD88, the MyD88 mutant known as MyD88-lpr or a MyD88-toll mutant only. After one day, cells were stimulated with 20 ng/ml TNF or IL-1 and luciferase activity from the NF-κB reporter gene measured. Expression of the dominant negative (inhibitory) MyD88-lpr protein could specifically inhibit the IL-1 but not TNF-induced NF-κB activation, whereas wild-type MyD88 had no effect as expected.

FIG. 4: Expression of dominant negative (inhibitor) but not wild-type MyD88 blocks p38 MAPK, p42/44 MAPK and NF-κB activation as well as IκBα degradation in human skin fibroblasts (HSF) in response to IL-1

Figure 4A:
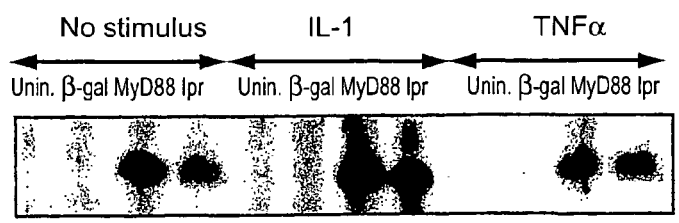
Figure 4B:
Figure 4C:
Figure 4D:
Figure 4E:
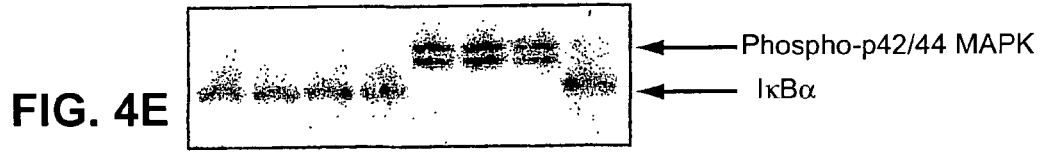

Primary human skin fibroblasts (HSF) were infected in serum-free RPMI with an adenovirus encoding a control protein β-gal, wild-type MyD88 or the dominant negative form MyD88-lpr. After 2 h the virus was removed and the cells were cultured in 5% FCS RPMI for 1 day to allow expression to take place. Then, they were stimulated with 20 ng/ml IL-1 or TNFα for 30 mm and cells were lysed for cytosolic and nuclear extracts. Western blotting was used to analyse cytosolic extracts for MyD88 (FIG. 4A), phosphorylated p38 MAPK (FIG. 4C) and p42/44 MAPK (FIG. 4D), and IκBα (FIG. 4E). Electrophoretic mobility shift assay (EMSA) was used to analyse nuclear NE-κB-DNA binding activity (FIG. 4B).

Figure 5:
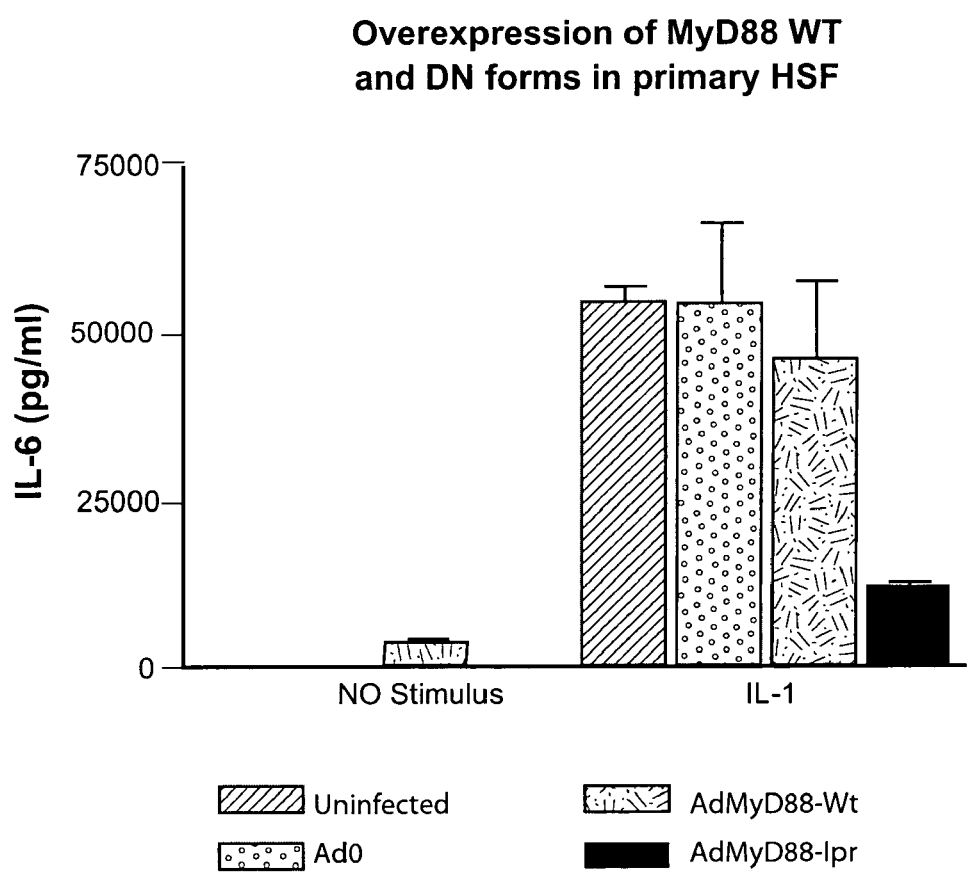

FIG. 5: Expression of dominant negative (inhibitor) but not wild-type MyD88 blocks IL-1 induced IL-6 production in HSF Primary human skin fibroblasts (HSF) were infected in serum-free RPMI with an adenovirus encoding a control protein β-gal, wild-type MyD88 or the dominant negative form MyD88-lpr. After 2 h the virus was removed and the cells were cultured in 5% FCS RPMI for 1 day to allow expression to take place. Then, they were stimulated with 20 ng/ml IL-1 for 24 h, supernatants collected and analyzed by ELISA for IL-6 production. Expression of the dominant negative MyD88-lpr could inhibit IL-1-induced IL-6 production in human skin fibroblasts.

Figure 6:
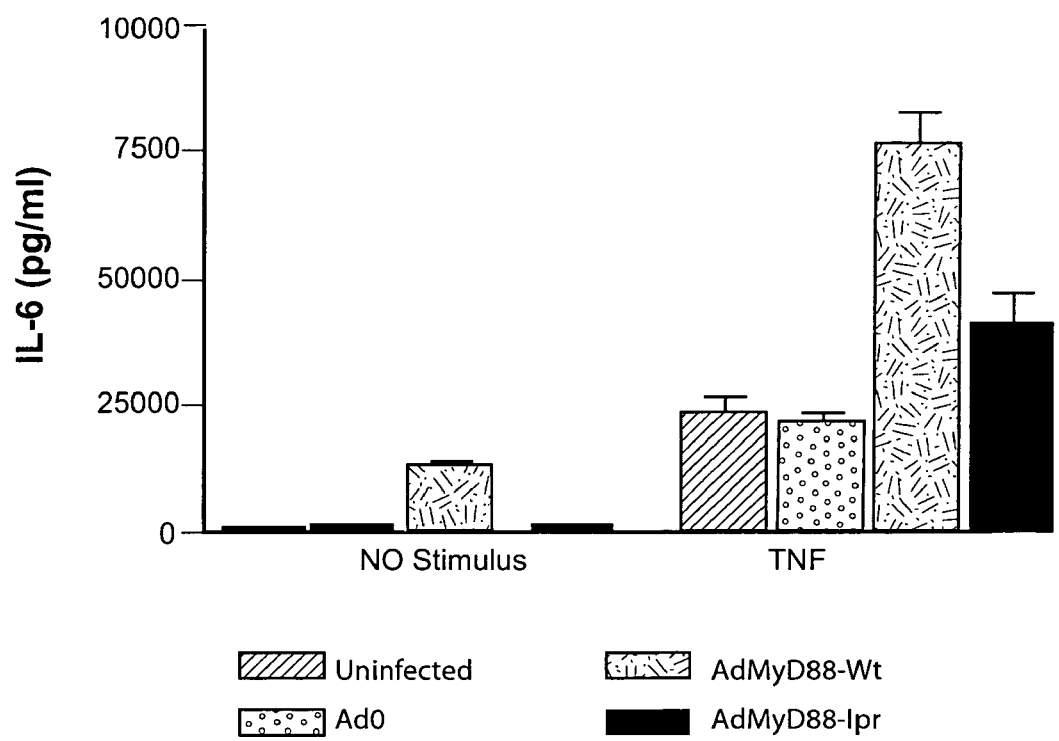

FIG. 6: Expression of dominant negative (inhibitor) or wild-type MyD88 does not block TNFα-induced IL-6 production in HSF Primary human skin fibroblasts were infected in serum-free RPMI with an adenovirus encoding a control protein β-gal, wild-type MyD88 or the dominant negative from MyD88-lpr. After 2 h the virus was removed and the cells were cultured in 5% FCS RPMI for 1 day to allow expression to take place. Then, they were stimulated with 20 ng/ml IL-1 for 24 h, supernatants collected and analyzed by ELISA for IL-8 production. Expression of the dominant negative MyD88-lpr could inhibit IL-1-induced IL-8 production in human skin fibroblasts.

Figure 7:
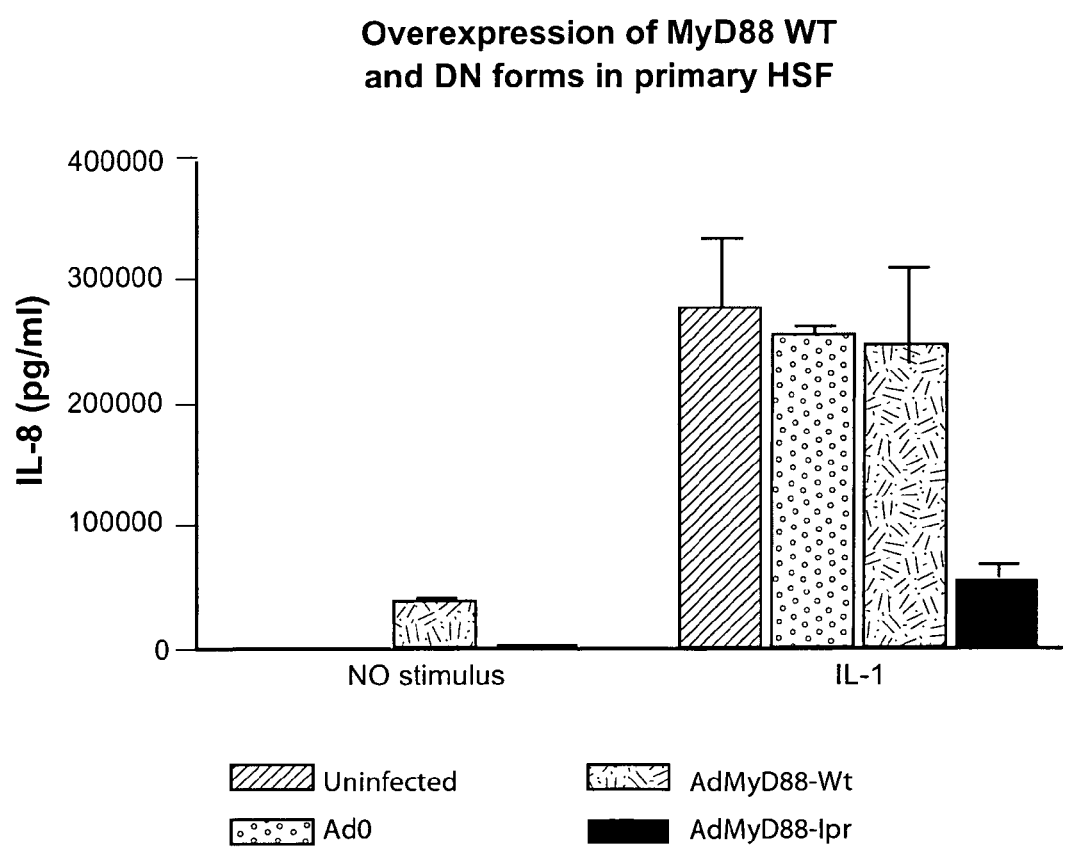

FIG. 7: Expression of dominant negative (inhibitor) but not wild-type MyD88 blocks IL-1 induced IL-8 production in HSF Primary human skin fibroblasts were infected in serum-free RPMI with an adenovirus encoding a control protein β-gal, wild-type MyD88 or the dominant negative form MyD88-lpr. After 2 h the virus was removed and the cells were cultured in 5% FCS RPMI for 1 day to allow expression to take place. Then, they were stimulated with 20 ng/ml TNFα for 24 h, supernatants collected and analyzed by ELISA for IL-6 production. Expression of the dominant negative MyD88-lpr could not inhibit TNFα-induced IL-6 production in human skin fibroblasts showing that MyD88 is required specifically for the IL-1 but not the TNF signalling pathway.

Figure 8:
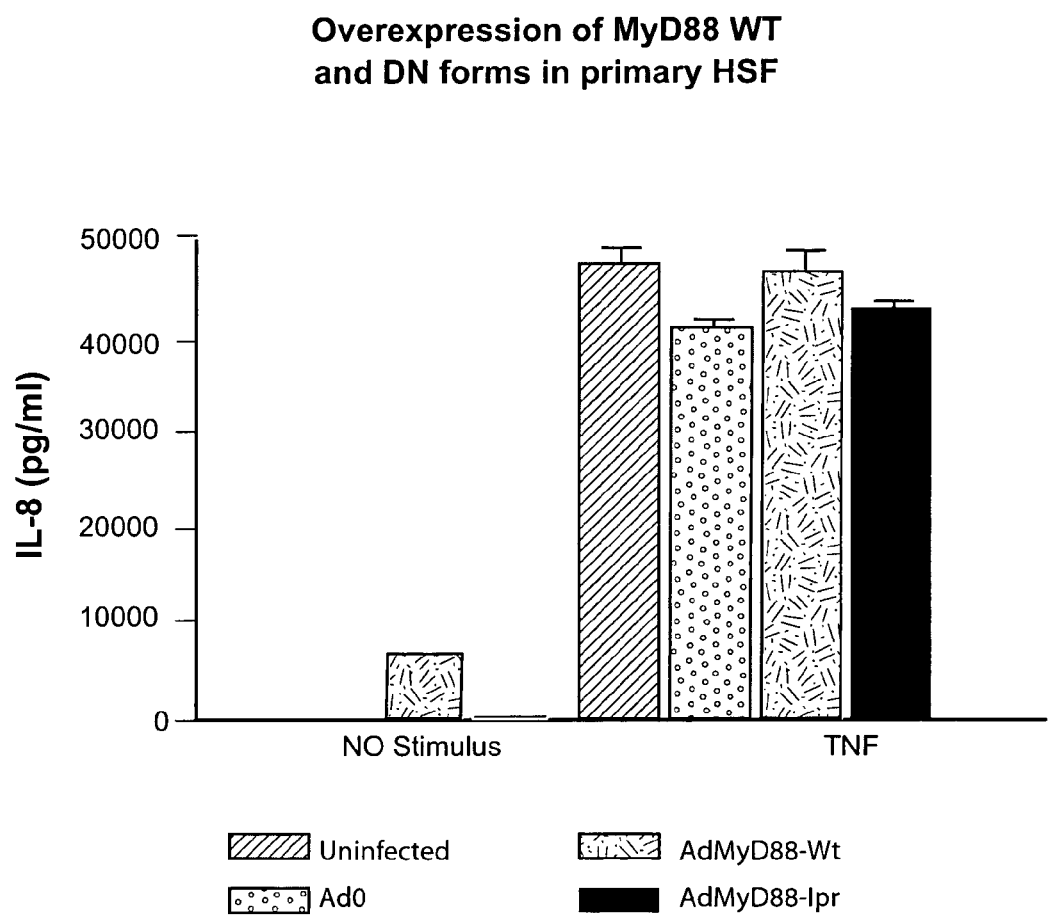
Figure 9A:
Figure 9B:
Figure 9C:
Figure 9D:
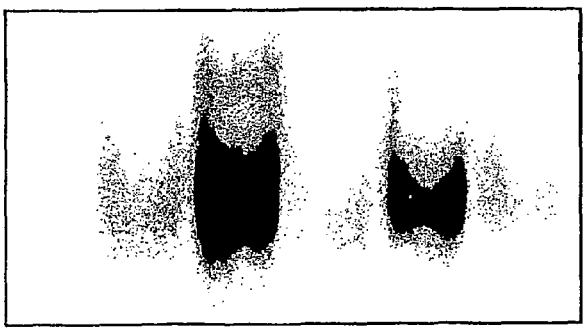

FIG. 8: Expression of dominant negative (inhibitor) or wild-type MyD88 does not block TNFα-induced IL-8 production in HSF Primary human skin fibroblasts were infected in serum-free RPMI with an adenovirus encoding a control protein β-gal, wild-type MyD88 or the dominant negative form MyD88-lpr. After 2 h the virus was removed and the cells were cultured in 5% FCS RPMI for 1 day to allow expression to take place. Then, they were stimulated with 20 ng/ml TNFα for 24 h, supernatants collected and analyzed by ELISA for IL-8 production. Expression of the dominant negative MyD88-lpr did not inhibit TNFα-induced IL-8 production in human skin fibroblasts showing that MyD88 is required specifically for the IL-1 but not the TNF signalling pathway.

FIG. 9: Expression of dominant negative (inhibitor) but not wild-type MyD88 blocks p42/44 MAPK and NF-κB activation as well as IκBα degradation in human umbilical vein endothelial cells (HUVEC) in response to IL-1 and LPS Primary umbilical vein endothelial cells (HUVEC) were infected in serum-free RPMI with an adenovirus encoding a control protein β-gal or the dominant negative form MyD88-lpr. After 2 h the virus was removed and the cells were cultured in 5% FCS RPMI for 1 day to allow expression to take place. Then, they were stimulated with 20 ng/ml IL-1 or 1 μg/ml LPS for 30 mm and cells were lysed for cytosolic and nuclear extracts. Western blotting was used to analyse cytosolic extracts for MyD88 expression (FIG. 9A), phosphorylation of p42/44 MAPK (FIG. 9C), and IκBα (FIG. 9B), expression. Electrophoretic mobility shift assay (EMSA) was used to analyse nuclear NF-κB-DNA binding activity (FIG. 9D).

Figure 10:
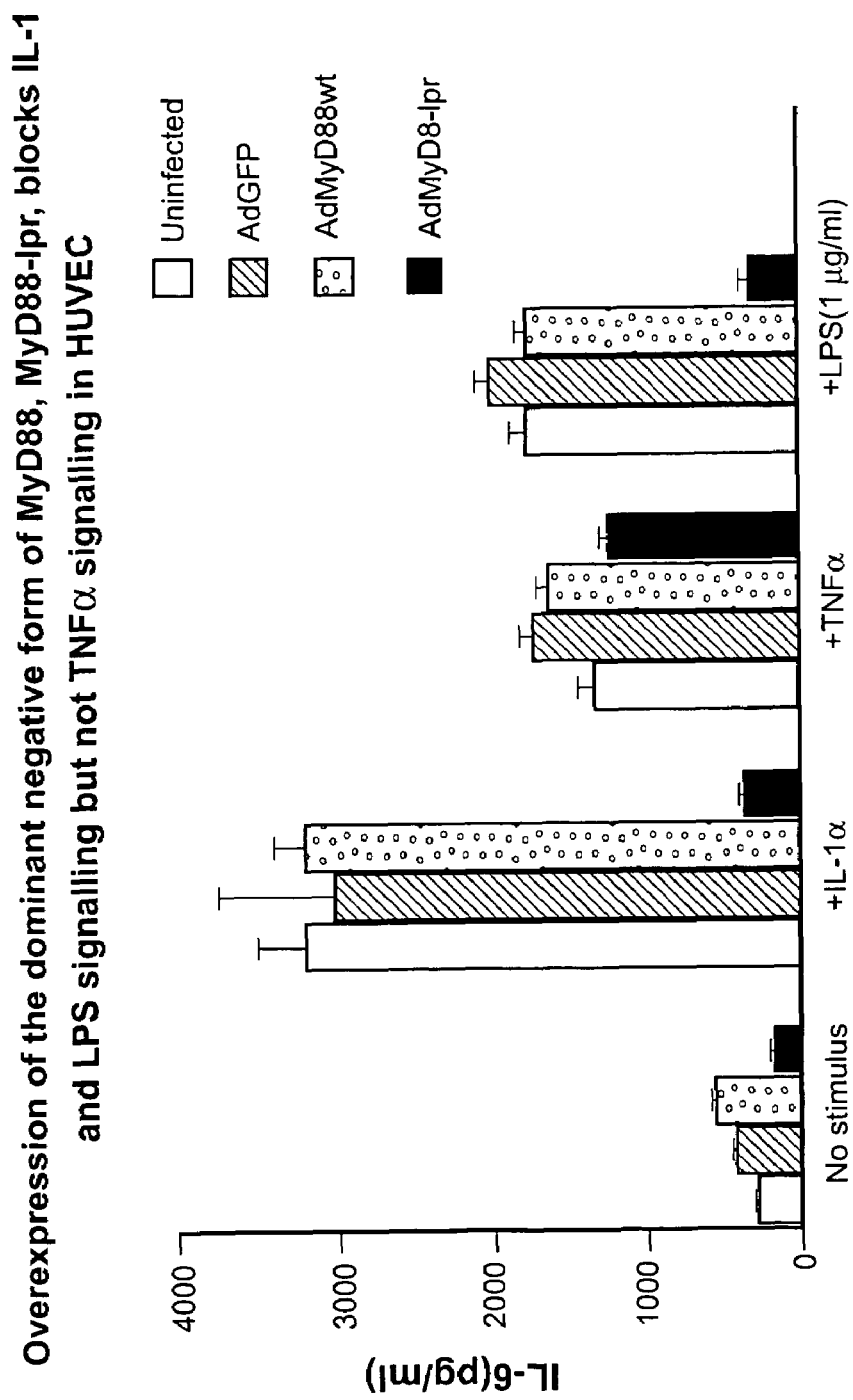

FIG. 10: Expression of dominant negative (inhibitor) but not wild-type MyD88 blocks IL-1- and LPS-induced but not TNF-induced IL-6 production in HUVEC Primary HUVEC were infected in serum-free RPMI with an adenovirus encoding a control protein β-gal, wild-type MyD88, the dominant negative form MyD88-lpr, IκBα or a dominant-negative form of IKK-2. After 2 h the virus was removed and the cells were cultured in 5% FCS RPMI for 1 day to allow expression to take place. Then, they were stimulated with 20 ng/ml IL-1, 20 ng/ml TNFα or 1 μg/ml LPS for 24 h, supernatants collected and analyzed by ELISA for IL-6 production. Expression of the dominant negative MyD88-lpr could inhibit IL-1- and LPS-induced IL-6 production suggesting that it is a specific inhibitor of toll-related receptors. IκBα and dominant-negative IKK-2 also blocked IL-6-production as they act downstream of MyD88 in the toll-related receptor signal transduction pathway. The TNF-induced IL-6 production was not blocked as MyD88 is not involved. However, IKK-2 and IκBα are also utilised by the TNF-R signal transduction pathway.

Figure 11:
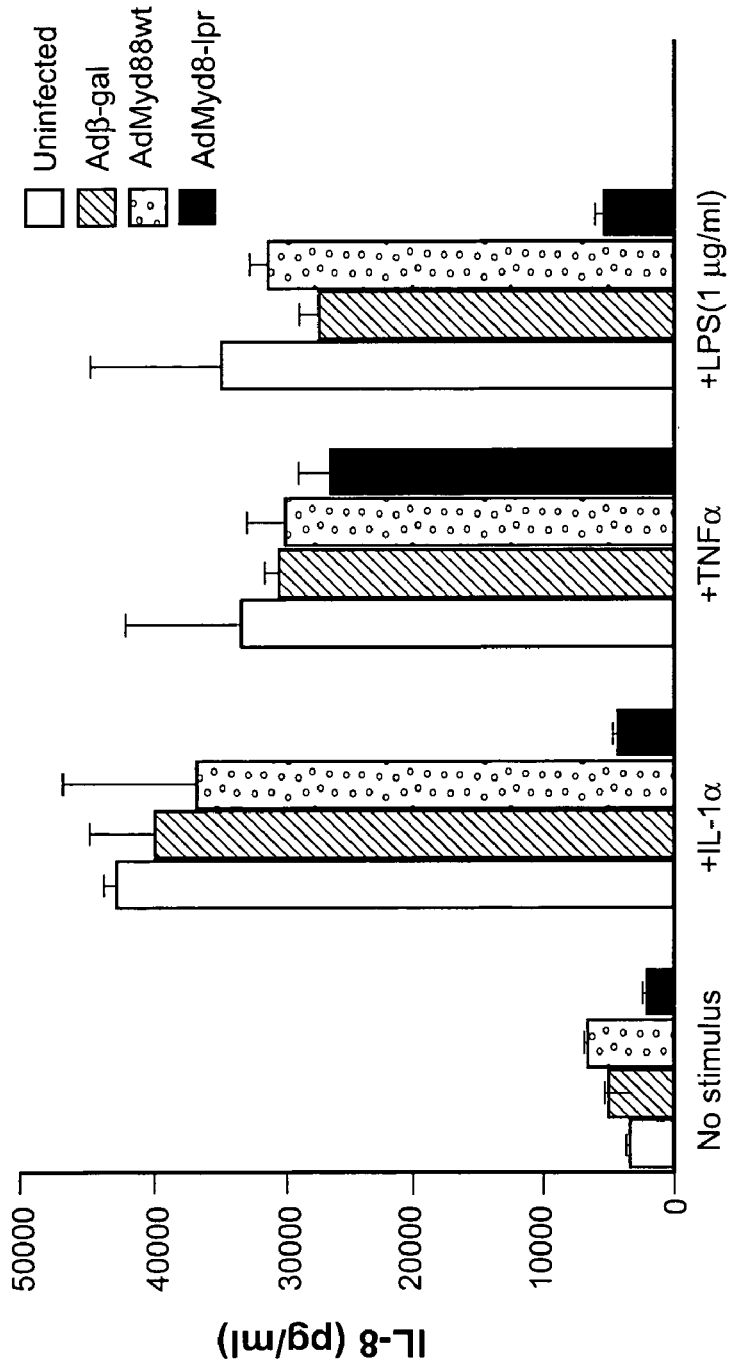

FIG. 11: Expression of dominant negative (inhibitor) but not wild-type MyD88 blocks IL-1- and LPS-induced but not TNF-induced IL-8 production in HUVEC Primary HUVEC were infected in serum-free RPMI with an adenovirus encoding a control protein β-gal, wild-type MyD88, the dominant negative form MyD88-lpr, IκBα or a dominant-negative form of IKK-2. After 2 h the virus was removed and the cells were cultured in 5% FCS RPMI for 1 day to allow expression to take place. Then, they were stimulated with 20 ng/ml IL-1, 20 ng/ml TNFα or 1 μg/ml LPS for 24 h, supernatants collected and analyzed by ELISA for IL-8 production. Expression of the dominant negative MyD88-lpr could inhibit IL-1- and LPS-induced IL-8 production suggesting that it is a specific inhibitor of toll-related receptors. IκBα and dominant-negative IKK-2 also blocked IL-8-production as they act downstream of MyD88 in the toll-related receptor signal transduction pathway. The TNF-induced IL-8 production was not blocked as MyD88 is not involved. However, IKK-2 and IκBα are also utilised by the TNF-R signal transduction pathway.

Figure 12:
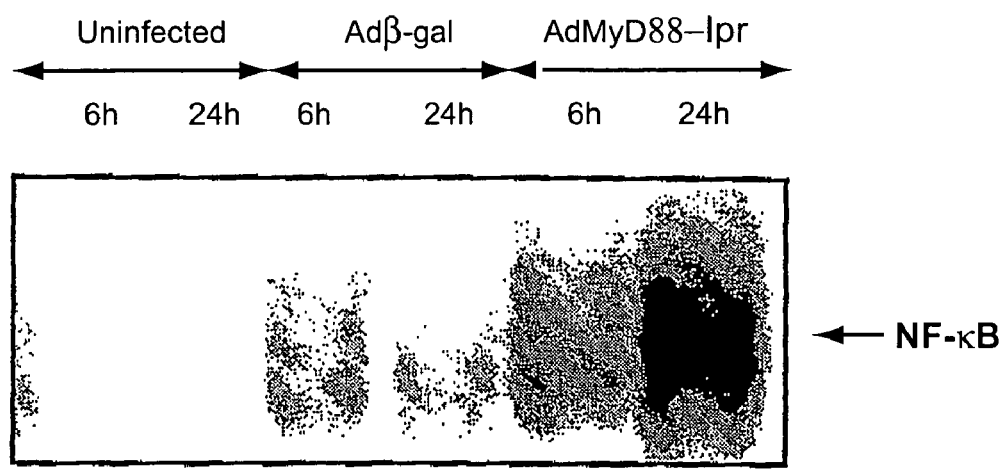

FIG. 12: Expression of dominant negative (inhibitor) MyD88 in dendritic cells has the opposite effect: it induces NF-κB activation Immature DC were generated from peripheral blood monocytes after 5 days of culture with 50 ng/ml GM-CSF and 10 ng/ml IL-4. Then, they were left uninfected, or infected in serum-free medium with a control adenovirus without insert (Ad0) and an Adenovirus encoding dominant-negative MyD88 (AdMyD88-lpr). A multiplicity of infection of 100 was used. After 6 h and 24 h expression, cells were lysed and their nuclear extracts examined for NF-κB DNA-binding activity by EMSA. Surprisingly, expression of dominant negative MyD88 could induce on its own NF-κB activation which is totally in constrast with what has been previously found.

Figure 13:
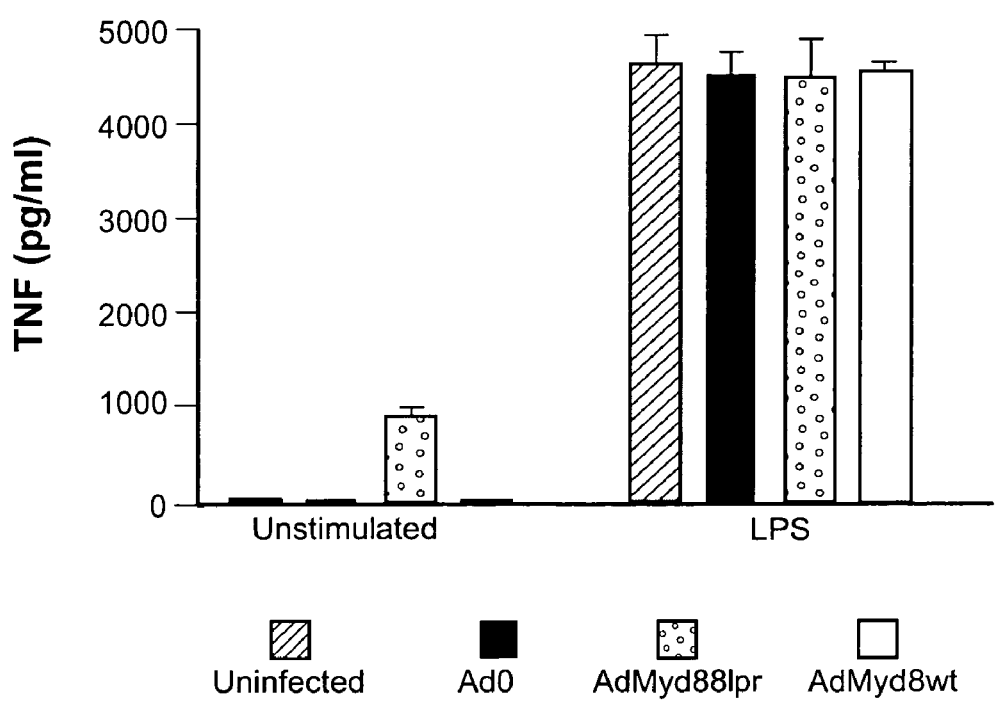

FIG. 13: Expression of dominant negative (inhibitor) but not wild-type MyD88 induces TNFα production on its own and does not inhibit LPS-induced TNFα production in dendritic cells Immature DC were generated from peripheral blood monocytes after 5 days of culture with 50 ng/ml GM-CSF and 10 ng/ml IL-4. Then, they were left uninfected, or infected in serum-free medium with with a control adenovirus encoding β-gal (Adβ-gal), an adenovirus encoding dominant-negative MyD88 (Adlpr) and an adenovirus encoding wild-type MyD88 (AdMyD88wt). Adtoll has beenshown to be nonfunctional and should be ignored. A multiplicity of infection of 100 was used. After 24 h, cells were stimulated with 100 ng/ml LPS. Surprisingly, expression of dominant negative MyD88 could induce dendritic cell TNFα production on its own, in the absence of additional stimulation. Moreover, it could not inhibit LPS-induced TNFα production, a finding that is in constrast with everything previously found.

Figure 14:
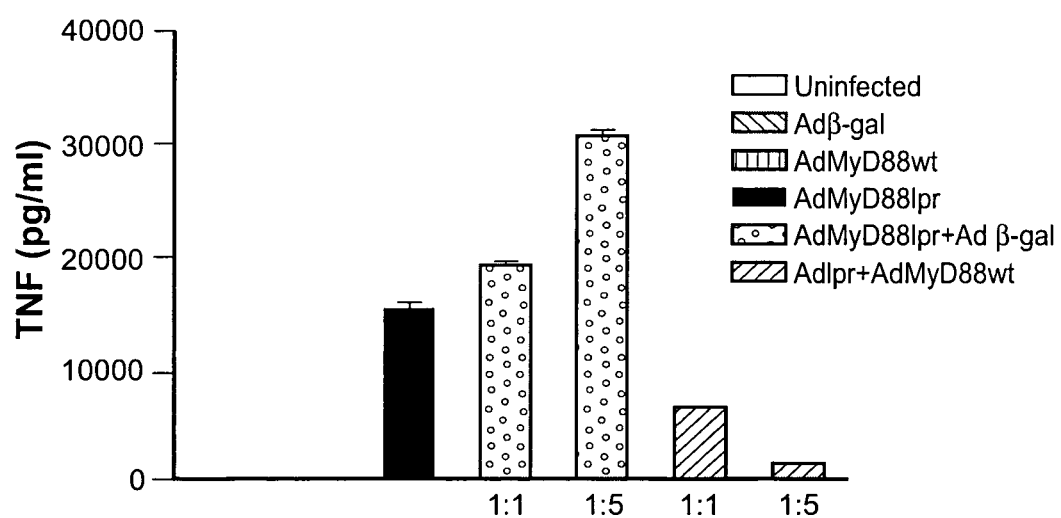

FIG. 14: Expression of wild-type MyD88 abrogates the MyD88-lpr(dominant-negative)-induced TNFα production in dendritic cells Immature DC were generated from peripheral blood monocytes after 5 days of culture with 50 ng/ml GM-CSF and 10 ng/ml IL-4. Then, they were left uninfected, or infected in serum-free medium with a control adenovirus encoding β-gal (Adβ-gal), an adenovirus encoding wild-type MyD88 (AdMyD88wt) and an adenovirus encoding dominant-negative MyD88 (Adlpr). In some cases, double infection by Adlpr and Adβ-gal or AdMyD88wt at ratios 1:1 and 1:5 was used. A multiplicity of infection of 100 was used for single infections. After 24 h, cells were stimulated with 100 ng/ml LPS. Surprisingly, expression of dominant negative MyD88 could induce dendritic cell TNFα production on its own, in the absence of additional stimulation. Moreover, it could not inhibit LPS-induced TNFα production, a finding that is in contrast with everything previously found.

Figure 15:
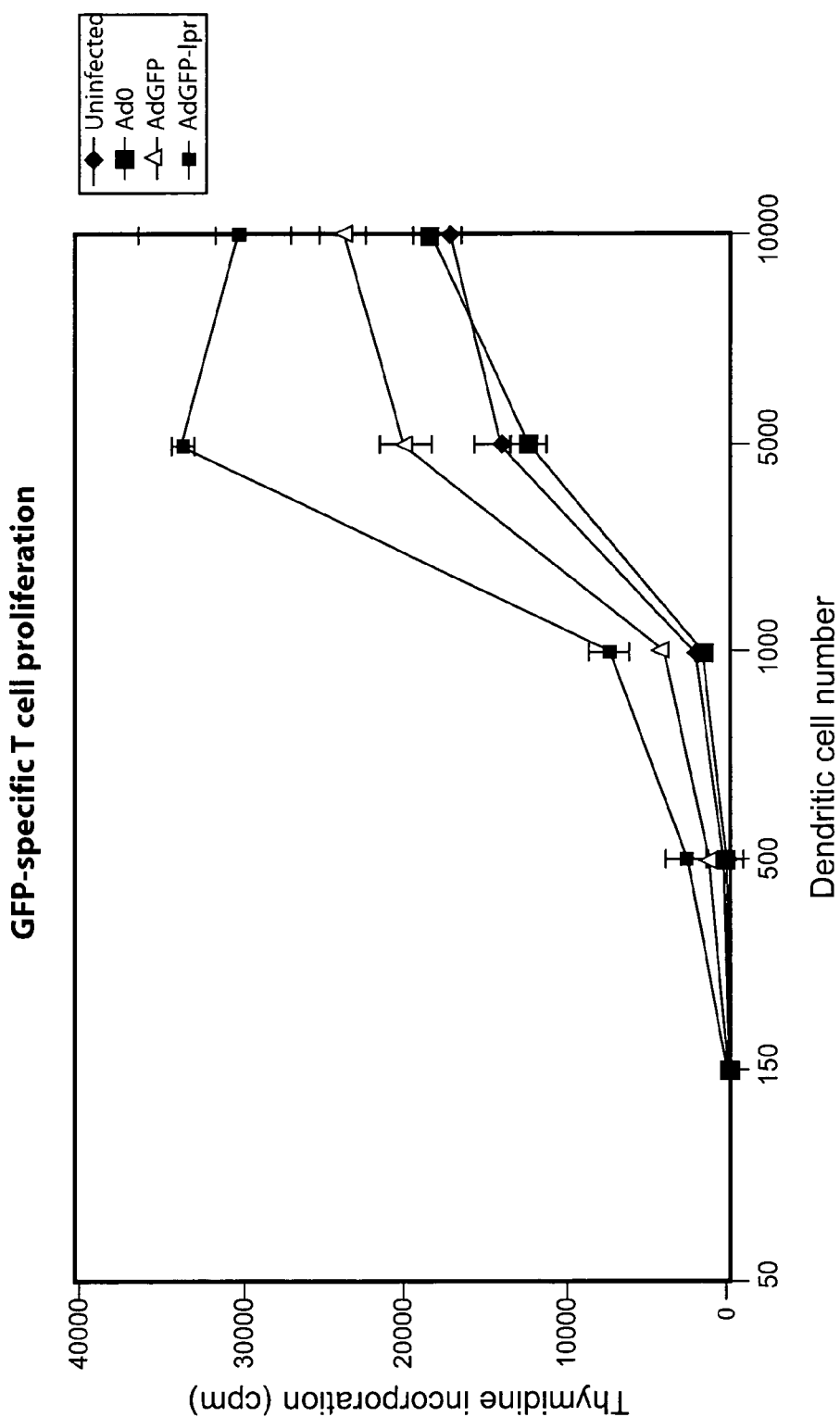

FIG. 15: Expression of dominant-negative MyD88 in dendritic cells enhances antigen-specific T cell proliferation Immature DC were generated from peripheral blood monocytes after 5 days of culture with 50 ng/ml GM-CSF and 10 ng/ml IL-4. Then, they were left uninfected, or infected in serum-free medium with a control adenovirus without insert (Ad0), an adenovirus encoding green fluorescent protein as a prototype antigen (AdGFP), and an adenovirus encoding GFP linked together with the dominant negative MyD88 (AdGFP-lpr). After 48 h, graded doses of dendritic cells were cultured with $2 \times 10^4$ antigen-specific T cells and proliferation was measured at day 3. Delivery of the antigen GFP to dendritic cells induced antigen-specific T cell proliferation that was enhanced by expression of dominant negative MyD88. This is in agreement with our unexpected result that inhibition of MyD88 activity in dendritic cells, but not human skin fibroblasts or HUVEC, induces dendritic cell activation.

Figure 16:
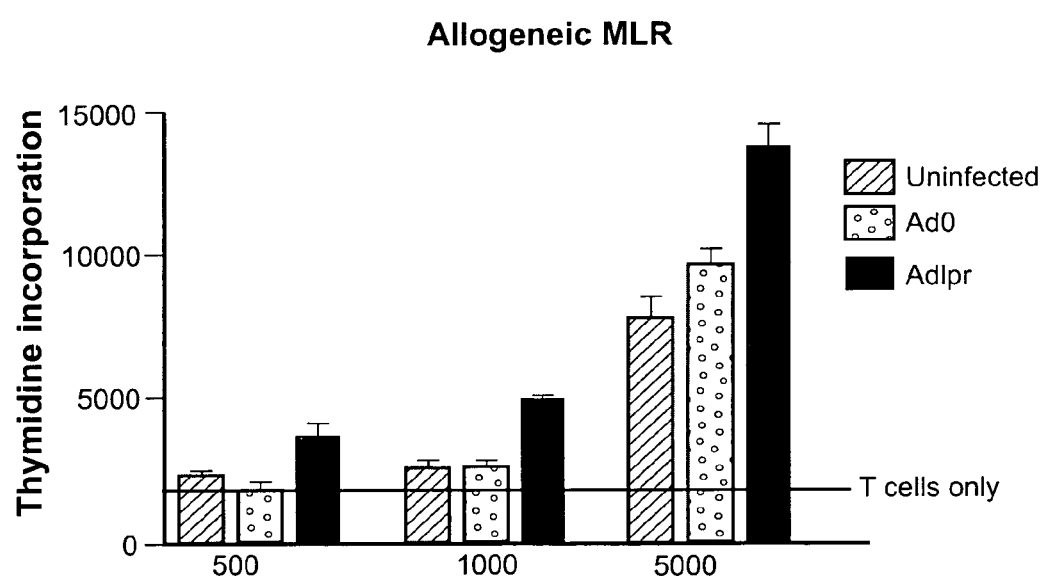

FIG. 16: Expression of dominant-negative MyD88 in dendritic cells enhances the allogeneic mixed lymphocyte reaction (MLR)

Immature DC were generated from peripheral blood monocytes after 5 days of culture with 50 ng/ml GM-CSF and 10 ng/ml IL-4. Then, they were left uninfected, or infected in serum-free medium with a control adenovirus without insert (Ad0), and an adenovirus encoding the dominant negative form of MyD88 (Adlpr). After 48 h, graded doses of dendritic cells were cultured with $1 \times 10^5$ allogeneic T cells and proliferation was measured at day 6. Expression of dominant negative MyD88 enhances the allogeneic T cell proliferation, a finding that is indicative of increased DC antigen presentation.

Figure 17A:
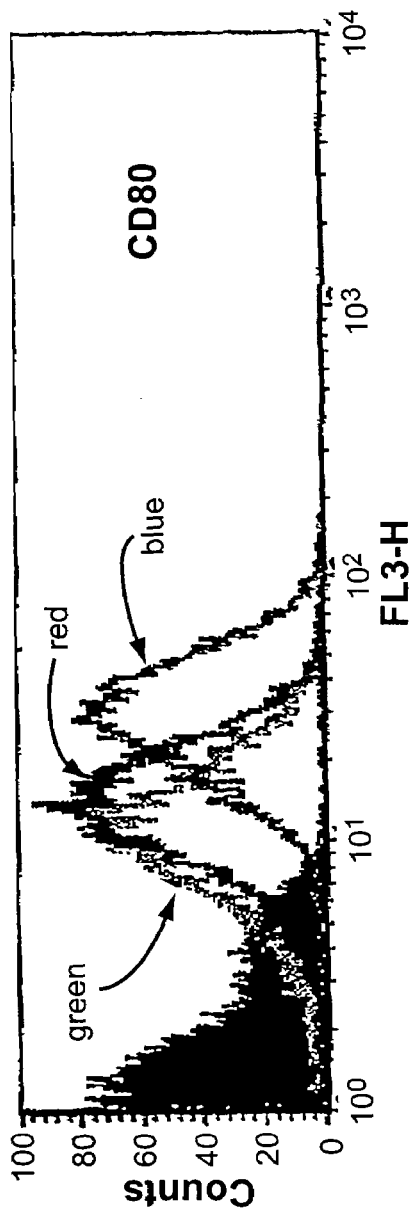
Figure 17B:
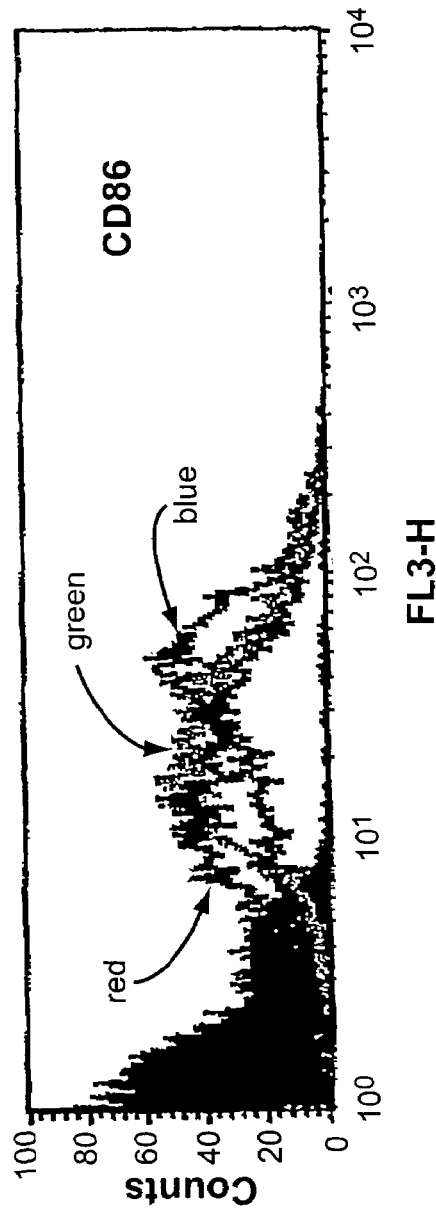

FIG. 17: Expression of dominant-negative MyD88 in dendritic cells enhances the expression of costimulatory molecules (CD80, CD86)

Immature DC were generated from peripheral blood monocytes after 5 days of culture with 50 ng/ml GM-CSF and 10 ng/ml IL-4. Then, they were left uninfected, or infected in serum-free medium with a control adenovirus encoding GFP, and with an adenovirus encoding dominant negative MyD88 (Adlpr). After 48 h, dendritic cells were collected and stained for CD80 (FIG. 17A) and CD86 (FIG. 17B), two very important costimulatory molecules required for efficient antigen-presenting function. Expression of the dominant negative form of MyD88 enhanced CD80 and CD86 cell surface expression, which is indicative of enhanced dendritic cell antigen-presenting function.

Figure 18:
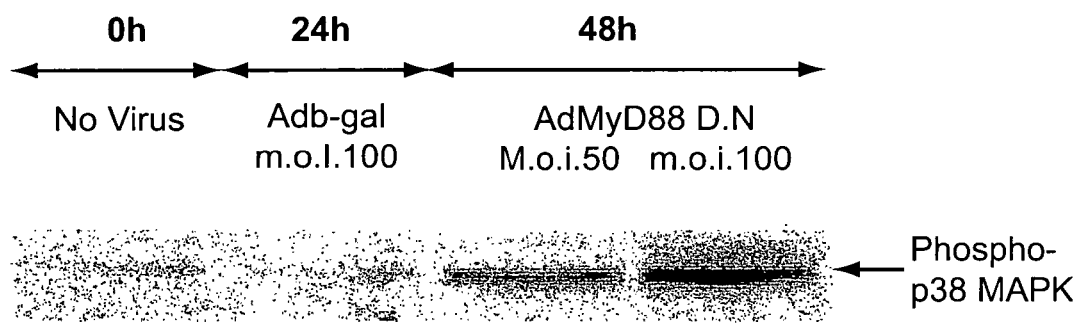

FIG. 18: Expression of dominant-negative MyD88 in macrophages induces p38 MAPK phosphorylation Human macrophages were differentiated from peripheral blood monocytes by addition of 100 ng/ml M-CSF for 2-3 days in 5% FCS RPMI. Then, they were left uninfected, infected in serum-free medium with a control adenovirus encoding β-gal, or infected with an adenovirus encoding dominant negative MyD88 (Adlpr). An moi of 100 (or 50 in one case) was used as shown. After 6, 24 and 48 h, cells were lysed and extracts assayed for p38 MAPK activity using western blotting and phospho-p38 MAPK-specific antibodies. Unexpectedly, expression of dominant-negative MyD88 induces p38 MAPK activity in human macrophages.

FIG. 19: Expression of dominant-negative MyD88 in macrophages induces IRAK phosphorylation Human macrophages (FIG. 19A) were differentiated from peripheral blood monocytes by addition of 100 ng/ml M-CSF for 2-3 days in 5% FCS RPMI. Hela cells (FIG. 19B) cultured in 5% FCS DMEM were also used. Both cell types were left uninfected, infected in serum-free medium with a control adenovirus encoding β-gal, an adenovirus encoding wild-type MyD88 or an adenovirus encoding dominant negative MyD88 (Adlpr). An moi of 100 was used. After 5 mm or 12 h, cells were lysed and extracts assayed for IRAK and phospho-IRAK using western blotting. In Hela cells, expression of dominant negative MyD88 (MyD88-lpr) was found to inhibit IL-1-induced activation of IRAK. Unexpectedly, however, expression of dominant-negative MyD88 induces IRAK activity in human macrophages that is not increased by the addition of LPS. This finding suggests that MyD88 activity is also required for an inhibitory signal in macrophages (but not Hela cells) that inhibits IRAK phosphorylation, and its blockade results in the activation of IRAK.

Figure 20:
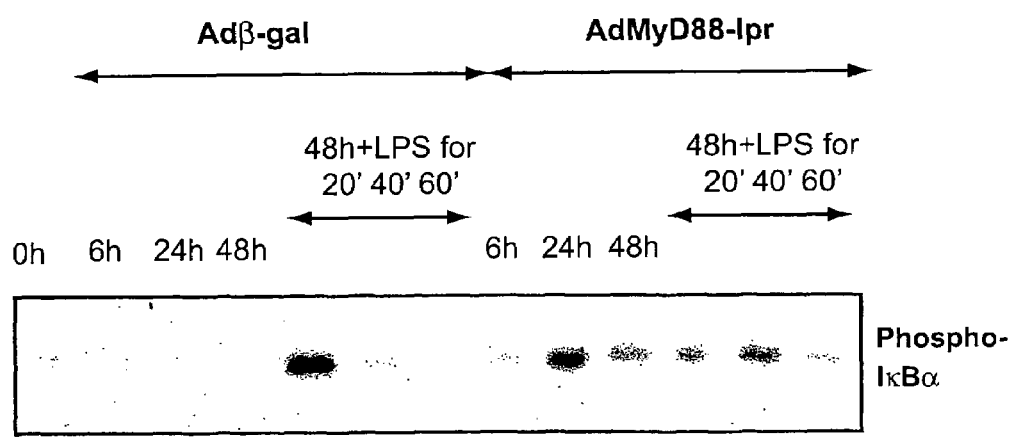

FIG. 20: Expression of dominant-negative MyD88 in macrophagaes induces IκBα phosphorylation Human macrophages were differentiated from peripheral blood monocytes by addition of 100 ng/ml M-CSF for 2-3 days in 5% FCS RPMI. Cells infected in serum-free medium with a control adenovirus encoding β-gal or an adenovirus encoding dominant negative MyD88 (Adlpr). An moi of 100 was used. After 24 h, cells were lysed and extracts assayed for phospho-IκBα using western blotting. Unexpectedly, expression of dominant-negative MyD88 induces IκBα phosphorylation in human macrophages.

FIG. 21: Expression of dominant-negative but not wild-type MyD88 in macrophages induces TNFα, IL-6 and IL-8 production in the absence of any stimulus.

Human macrophages were differentiated from peripheral blood monocytes by addition of 100 ng/ml M-CSF for 2-3 days in 5% FCS RPMI. Then, they were left uninfected, infected in serum-free medium with a control adenovirus encoding β-gal, infected with an adenovirus encoding wild-type MyD88 or infected with an adenovirus encoding dominant negative MyD88 (Adlpr). An moi of 100 was used. FIG. 21A: After 48 h, supernatants were collected and assayed for TNFα, IL-6 and IL-8 cytokine production in the absence of any further stimulation. Cytokine production could be detected in cells expressing dominant negative MyD88 but not cells expressing wild-type MyD88 or control cells. This suggested that blocking MyD88 activity in macrophages, as in dendritic cells but not HSF or HUVEC, results in the activation of cells and the release of inflammatory cytokines. FIG. 21B: At 0 h, 4 h, 24 h and 48 h of expression, supurnatants were collected and assayed by ELISA for TNF, IL-6 and IL-8. Only the results from cells overexpressing dominant negative MyD88 (MyD88-lpr) are shown as control cells or cells expressing wild-type MyD88 had background levels of cytokine production.

EXAMPLE 1

Toll-like Receptor Signalling in Human Cells

Materials and Methods

1. Reagents

Human recombinant GM-CSF and TNFα were kind gifts of Dr Glenn Larsen (GI) and Dr D Tracey (BASF), respectively. Human recombinant IL-4 was purchased from R&D Systems (Minneapolis, USA) and IL-1 was a gift from Hoffman La Roche. LPS was obtained from Sigma Chemical Co. (St Louis, USA).

2. Preparation of Peripheral Blood Mononuclear Cells

Peripheral blood mononuclear cells (PBMC) were obtained by density centrifugation of leukopheresis residues from healthy volunteers (North London Blood Transfusion Service, Colindale, UK). Heparinised residues were diluted 2× with HBSS and 25 ml were carefully layered over equal volumes of Ficoll-Hypaque lymphoprep (Nycomed, Oslo, Norway) in 50 ml sterile tubes prior to centrifugation for 30 minutes at 2000 rpm at room temperature. After centrifugation, the interface layer was collected and washed twice with HBSS (centrifuged for 10 minutes at 2000 rpm). PBMC were then collected and resuspended in 30 ml of RPMI containing 5% FCS.

3. Isolation of Peripheral Blood T Cells and Monocytes

Peripheral blood T cells and monocytes were obtained from PBMC after cell cell separation in a Beckman JE6 elutriator. Elutriation was performed in RPMI containing 1% FCS (elutriation medium). Lymphocyte and monocyte purity was assessed by flow cytometry using fluorochrome-conjugated anti-human monoclonal antibodies against CD45, CD3, CD14 and CD19 (Becton Dickinson, Oxford, UK). T lymphocyte fractions typically contained ~80% CD3-expressing cells, ~6% CD19-expressing cells and <1% CD14-expressing cells. Monocyte fractions routinely consisted of >85% CD14-expressing cells, <0.5% CD19 cells and <3% of CD3-expressing cells.

4. Differentiation of Monocytes with M-CSF for Adenoviral Infection

To optimize adenoviral infection, freshly elutriated monocytes were cultured at 1×10$^6$ cells/mil in 10 cm petri dishes (Falcon, UK) with 100 ng/ml of M-CSF (Genetics Institute, Boston, USA). After 2-3 days they were washed with PBS to remove non-adherent cells and the remaining adherent monocytes were incubated with 10 ml of cell dissociation solution (Sigma, UK) for 1 h at 37° C. The cell suspension was washed twice in RPMI containing 5% FCS and cell viability (90%) was assessed by trypan blue exclusion. Cells at this stage were 99% CD14 positive by FACS staining and were cultured at 1>10$^6$/ml, in 24-well or 48-well flat-bottomed tissue culture plates (Falcon, UK) for further experiments.

5. Differentiation of Monocytes to Dendritic Cells

Freshly elutriated monocytes were cultured at 1×10$^6$ cells/ml in 10 cm petri dishes (Falcon, UK) in 5% FCS RPMI supplemented with 50 ng/ml GM-CSF and 10 ng/ml IL-4 for 5-6 days. At day 3, cytokines were replenished. This method presents several advantages as compared to differentiation of dendritic cells directly from blood or bone marrow precursors. Besides being easy and giving high numbers of cells, it generates a homogenous population of cells with a stable "immature DC" phenotype. This phenotype can be pushed to maturation by addition of TNFα (10 ng/ml), LPS (100 ng/ml) or monocyte-conditioned medium (50% v/v) for a further 2-3 days to the DC.

6. 57A and Untransfected HELA, HUVEC and HSF

57A HELA cells were a generous gift of R. Hay (University of St Andrews, UK) and were maintained in 5% FCS 1% penicillin/streptomycin DMEM. Human umbilical vein endothelial cells (HUVEC) were isolated as previously described (Jaffe E A et al. (1973). *J Clin Invest* 52: 2745-8) and maintained in RPMI, in the presence of 10% FCS, 10% NCS, 1% penicillin/streptomycin, 15 µg/ml endothelial growth supplement (Sigma, Poole, UK) and 50 IU/ml heparin. Primary human skin fibroblasts (HSF) were obtained from circumcision speciments cultured in 5% FCS 1% penicillin/streptomycin DMEM in T-75 tissue culture flasks.

8. Adenoviral Vectors and Their Propagation

Recombinant, replication-deficient adenoviral vectors encoding *E. coli* β-galactosidase (Adβ-gal) or having no insert (Ad0) were provided by Drs A. Byrnes and M. Wood (Oxford University, UK). The GFP-expressing adenovirus (AdGFP) was generated by double recombination of AdTrack with AdEasy-1 adenoviral plasmid provided by Prof B. Vogelstein (The Howard Huges Medical Institute, Baltimore, USA). AdMyD88wt and AdMyD88lpr were generated from plasmids provided by Dr Xu (University of Texas, Southwestern) and Dr K. Burns (Lausanne, Switzerland). In particular, pAdTrackCMV was used for AdMEKK-1 wt, whereas for AdMyD88wt and AdMyD88lpr, a pAdTrack.CMV vector derivative, termed AdTrack.CMVKS17, was used. pAdTrack.CMVKS17 was constructed by removing the EcoRI site of AdTrack.CMV as well as its multiple cloning site (MCS), and by inserting the larger multiple cloning site of the vector pBCSK(+) (Stratagene). Recombinant viruses were generated in BJ5183 bacterial cells transformed by the heat-shock method with 1 µg of linearised pAdTrack.CMV-MEKK1 wt, AdTrack.CMVKS17-MyD88wt or AdTrack.CMVKS17-My88lpr constructs and 100 ng of replication-deficient adenoviral vector pAdEasy-1. Positive recombinant clones were selected through their resistance to kanamycin. Following selection, DNA extracted was used for virus propagation in the 293 human embryonic kidney cells. Viruses were purified by ultracentrifugation through two caesium chloride gradients, as described in He et al.(He T. C. et al. (1998). *Science* 281: 1509-12). Titres of viral stocks were determined by plaque assay, in HEK 293 cells, after exposure for 1 hour in serum free DMEM medium (Gibco BRL) and subsequently overlayed with an (1.5%) agarose/(2×DMEM with 4% FCS) mixture (v/v 1:1) and incubated for 10-14 days. (He T. C. et al. (1998). *Science* 281: 1509-12).

9. Adenoviral Infection of Cells

M-CSF-differentiated macrophages and immature or mature dendritic cells were collected, counted and replated. Then, they were infected in serum-free RPMI with replication-deficient adenoviruses expressing the gene of interest. A multiplicity of infection of 50-100 for macrophages and immature DC, and 150-300, for mature DC, was used. After 2 h, the virus was removed and cells were cultured in complete medium for an additional 1-2 days to allow expression of the protein of interest. Then, they were used in further experiments.

Similarly, 57A HELA, HUVEC and HSF were infected in serum-free medium for 2 h. A multiplicity of infection of 40-100 was used. Then, the virus was removed, complete medium added backed and cells were further cultured for another 1-2 days.

10. Establishment of Antigen-Specific T Cell Lines

Green fluorescent protein was purchased from Clontech. To establish antigen-specific polyclonal T cell lines, $1 \times 10^6$ PBMC/ml were cultured with 1 µg/ml green fluorescent protein (antigen) for 7 days and then with IL-2 at 20 ng/ml for another 10-14 days. Every 4 days IL-2 was replenished. This resulted in the expansion of antigen-specific T cells and cell death of most other cell populations present in PBMC. After 17-21 days of culture, a restimulation step was included by culturing the T cells with autologous irradiated PBMC at a 1:1 ratio and fresh antigen in the absence of IL-2. After 4 days IL-2 was added for another 10-14 days. This restimulation cycle was repeated at least 4 times before use of antigen-specific T cells in further experiments.

11. Proliferation Assays of Antigen-Specific T Cells

To assess the specificity of antigen-specific T cell lines, $1 \times 10^5$ of antigen-specific T cells were cultured with $1 \times 10^5$ autologous irradiated PBMC and various concentrations of antigen in 96-well flat-bottomed microtiter plates. After 3 days, cells were pulsed with [$^3$H]Thymidine overnight and harvested the following day.

To measure dendritic cell-induced antigen-specific T cell proliferation, $1 \times 10^5$ antigen-specific T cells were cultured with graded doses of irradiated or mitomycin-treated dendritic cells that were unplulsed, pulsed with antigen, uninfected or adenovirus-infected. [$^3$H]-Thymidine incorporation was measured after 2 days. All antigen-specific proliferation assays were done in triplicates.

12. Mixed Lymphocyte Reaction (MLR)

To assay the immunostimulatory capacity of non-irradiated or irradiated (3000 rad from a $^{137}$Cs source) DC, uninfected and adenovirus-infected, DC were cultured in graded doses with $1 \times 10^5$ of allogeneic elutriated T cells in quadruplicate in a 96-well flat-bottom microtiter plate (Falcon). Proliferation was measured on day 5 by thymidine incorporation after a 16 h pulse with [$^3$H] thymidine (0.5 µCi/well; Amersham Life Science, UK).

13. Cytokine Analysis

Cells were infected with adenoviral vectors for 2 h and, then, cultured for a further 2 days to allow overexpression of the relevant protein to occur. 24 h after stimulation of the cells, culture supernatants were collected and kept frozen. Cytokine levels in cell culture supernatants were measured by standard 2 or 3 layer sandwich ELISA techniques using specific monoclonal and polyclonal antibodies for TNFα, IL-4, IL-6, IL-8, IL-12 and IFNγ. Antibody pairs and standards for these assays have been purchased from Pharmingen, with the exception of IL-12 reagents that were gifted from the Genetics Institute (Boston, USA).

14. Immunofluorescence Staining and Flow Cytometry

For FACS staining, cells were first harvested. For adherent cells where surface receptors need to be intact, a warm 2% EDTA in PBS solution was used for 20 min at 37° C. After cells were in solution, they were washed once and then resuspended in ice-cold FACS washing buffer. All subsequent incubations were performed at 4° C. For each analysis, $5 \times 10^5$ cells were incubated with the relevant antigen-specific antibody or isotype control for 30 min and then washed twice with FACS washing buffer. Cells were then examined by flow cytometry. Cells were ready for analysis on a FACScan flow cytometer (Becton and Dickinson) by using the CellQuest (Becton Dickinson). Directly conjugated monoclonal antibodies to HLA-DR, HLA-A,B,C, CD80, CD86, CD3, CD14 and CD25 were purchased by Pharmingen, San Diego, USA).

15. Preparation of Cytosolic Protein Extracts

Cytosolic extracts were prepared to investigate biochemical events involved in signal transduction by western blotting. Adherent cells were scraped from the tissue culture plate/flask into fresh PBS and harvested by centrifugation (13000 g for 10 seconds at 4° C.). Non-adherent cells were similarly pelleted by centifugation and washed once with fresh PBS. After discarding the supernatants, an appropriate quantity of ice-cold hypotonic lysis buffer (Whiteside S. T. et al (1992). *Nucleic Acids Res* 20: 1531-8) was added, depending on the number of cells to be lysed (50-100 µl per $1 \times 10^6$ cells). After incubation on ice for 10 minutes, lysates were centrifuged (13000 g, 5 minutes, 4° C.) in order to remove nuclei and cell debris. The cleared lysates were then removed to fresh tubes, frozen and stored at −20° C. for subsequent estimation of protein concentration and use in western blotting.

16. Preparation of Nuclear Protein Extracts

Nuclear protein extracts were prepared to study the NF-κB activation and translocation from the cytosol to the nucleus and its DNA-binding ability. After lysis of cells in hypotonic lysis buffer (see section ), nuclei were pelleted by centrifugation (13000 g for 5 minutes at 4° C.), washed once in hypotonic lysis buffer to remove contaminating cytosolic proteins, and then resuspended in hypertonic extraction buffer for 1-2 hours at 4° C. under agitation. Hypotonic lysis buffer prevents leaching of proteins out of the nucleus during lysis, whereas hypertonic extraction buffer makes the nuclear membrane porous allowing nuclear proteins to escape into solution. After centrifugation (13000 g for 10 minutes at 4° C.) supernatants containing the nuclear protein were removed to fresh tubes and stored at −70° C. This method of nuclear extracts preparation is based on that of Whiteside S. T. et al (1992). *Nucleic Acids Res* 20: 1531-8.

17. Immunoprecipitation

To immunoprecipitate IRAK, cytosolic extracts were incubated with 3 µg of anti-IRAK antibody for 1 h at 4° C. under gentle shaking. Then, 50 µl of 50% slurry protein G sepharose (Amersham) were added and left for another 2 h shaking. Subsequently, IRAK bound to protein G sepharose was collected, washed four times, resuspended in Western Blot loading buffer, boiled for 5 min and then immediately used for Western blotting.

18. Protein Concentration Assay

Before using cytosolic or nuclear extracts in any further experimental procedure (e.g. western blotting, electrophoretic mobility shift assays), it was necessary to determine their protein concentration in order to ensure that equivalent amounts of protein were present in each sample. Protein concentrations were assessed by the Bradford assay. Briefly, 20 µl of appropriately diluted extracts were added in triplicates in a 96-well tissue culture plate along with 20 µl of a series of BSA concentrations (Sigma, UK) ranging from 10-1000 µg/ml to be used as a standard. 200 µl of Bradford reagent were then added to each well, and absorbance was measured at 595 nm in a spectrophotometer (Multiscan Bichromatic, Labsystems). From the linear standard curve formed by the range of BSA concentrations, protein amounts in the cytosolic and nuclear extracts were determined.

19. Western Blotting and Electrophoretic Mobility Shift Assay

Cytosolic proteins were separated by SDS-PAGE on a 10% (w/v) polyacrylamide gel, followed by electrotransfer onto nitrocellulose membranes. IκBα and IRAK were detected by using antibodies purchased from Santa Cruz Biotechnology (Santa Cruz, USA) and Upstate Biotechnology (USA), respectively, whereas the phosphorylated forms of IκBα, p38 and p42/44 MAPK were detected by antibodies from New England Biolabs.

20. Luciferase Assay

After LPS stimulation, cells were washed once in PBS and lysed with 100 µl of CAT lysis buffer (0.65% (v/v) NP40, 10 mM Tris-HCL pH 8, 0.1 mM EDTA pH8, 150 mM NaCl). Cell lysate (50 µl) was transferred into the well of a luminometer cuvette strip and Luciferase Assay Buffer (220 µl) added. Luciferase activity was measured with a Labsystem Luminometer by dispensing 30 µl luciferin (1.5 mM, Sigma, Poole, UK) per assay point. Cell lysates were assayed for protein concentration by Bradford assay and the measured luciferase activity was adjusted accordingly.

Results

Myd88 is a cytosolic protein containing toll and death domains (FIG. 1) that has been implicated in the signal transduction mechanisms of TRR members TLR (FIG. 2) and IL-1 receptors. A mutein of Myd88. Myd88lpr (FIG. 1), that contains a 53 amino acid deletion at the N-terminus and Phe56Asn mutation, can act as an inhibitor of IL-1, but not TNF activation of NF-κB (FIGS. 3 and 4) and MAPK activation (FIG. 4) in Hela cells (FIG. 3) and human skin fibroblasts (FIG. 4). In agreement with this result, IL-1 induced production of IL-6 in human skin fibroblasts was also inhibited when Myd88lpr was expressed in these cells (FIG. 5). In contrast Myd88 alone induced IL-6 production without any required for IL-1 activation (FIGS. 5 and 6). In contrast, Myd88lpr had no effect on TNF induced IL-6 production in HSF (FIG. 6). This would be expected as Myd88 is not implicated in TNF signalling. Myd88lpr was also capable of inhibiting IL-1 (FIG. 7), but not TNF-induced IL-8 (FIG. 8) production when expressed in human skin fibroblasts. The inhibiting effect of Myd88lpr was not confined to human skin fibroblasts, as studies in HUVECs transfected with AdMyd88lpr showed that IL-1 and LPS-induced NF-κB activation and p42/44 MAPK activation (FIG. 9) as well as IL-6 and IL-8 production (FIGS. 10 and 11) were also inhibited. In contrast to these results, we were surprised to observe that, when expressed in immature DC, Myd88lpr activated NF-κB (FIG. 12) without any requirement for additional stimulus. Moreover, expression of Myd88lpr was capable of inducing TNF production by immature DC (FIG. 13) whereas, unlike HSF, Myd88 had no effect (FIG. 13). The activating effect in DC of Myd88lpr was antagonised by Myd88, suggesting that there was competition by the two species for the same signalling pathway (FIG. 14). The activating effect of Myd88lpr translated to enhanced antigen presenting function of DC as shown by studies using GFP antigen specific T cells (FIG. 15) or in an allogenic MLR (FIG. 16). The antigen presenting function of DC is associated with the uprecaulation of the expression of costimulatory molecules on the suface of DC, such as CD80 and CD86. In agreement with its stimulating effect, Myd88lpr was found to enhance the expression of CD80 and CD86 when expressed in immature DC (FIG. 17). The activating effect of Myd88lpr was not confined to NT-κB, as expression of Myd88lpr in another potential APC, MCSF-human macrophages caused the activation of p38 MAPK (FIG. 18) and IRAK (FIG. 19). In contrast, but in agreement with the previous studies in Hela cell shown in FIG. 3, Myd88lpr inhibited IL-1-induced IRAK phosphorylation (FIG. 19). As for DC, Myd88lpr also induced IκBα phosphorylation in human MCSF macrophages (FIG. 20) as well as inducing or enhancing the production of TNF, IL-6 and IL-8 by human macrophages (FIG. 21).

Discussion

Toll related receptors include toll like receptors (TLR) that are trans-membrane receptor proteins with an extracellular protein containing leucine-rich repeats that may recognise LPS-LBP-CD14 complex and a cytoplasmic domain (toll domain) that is also found in the intracellular portion of the IL-1R and related molecules (Gay N J and Keth F H, Rock F et al 1997). TRR commonly utilise signalling components, such as Myd88, IRAK and TRAF6. In particular, Myd88 like the TRR, also contains a toll domain, which, via homotypic interaction, associates with the toll domain of the receptors. Myd88 also has a death domain by which it associates with IRAK and thus links the TRR with intracellular signalling pathways. It has been previously shown that expression of a dominant negative Myd88 inhibited IL-1 and LPS signalling in 293 cells (Mujio et al 1998) and both cytokine release and MAPK/NF-κB activation were inhibited. Similar results were obtained in human dermal micro-vessel endothelial cells and in the promonocytic cell line, THP-1 (Zhang FX et al 1999) where the transient overexpression of dominant negative Myd88 blocked IL-1 and LPS-induced NF-κB activation.

Myd88 knock-out mice are unable to induce LPS-dependent TNFα production (Kawai et al 1999). However, although IL-1 and IL-18 induced MAPK and NF-κB activation are knocked out, LPS-induced activation of these pathways in murine Myd88$^{-/-}$ macrophages appears normal, apart from being a bit delayed.

We have examined the role of TRRs in human primary cells by using an efficient adenoviral gene transfer technique to over-express wild type (Myd88wt) or a Myd88 mutein, Myd88lpr (FIG. 1). As expected from previous studies by Burns et al (1998), Myd88lpr was able to block IL-1 signalling in HSF, HUVECs and Hela cells. In addition Myd88lpr blocked LPS signalling in HUVECs. The inhibiting effect of Myd88lpr included both the activation of signalling molecules, such as NF-κB and MAPK, as well as cytokine production. As expected, TNF signalling pathways were unaffected. Moreover, in HSF, Myd88wt was able to induce cytokine production without any additional stimulus. Unexpectedly, however, we found that the introduction of Myd88lpr into immature DC and MCSF macrophages, resulted in the activation of NF-κB, MAPK and cytokine production. Moreover, in DC, the expression of the costimulatory molecules CD80 and CD86 centrally involved in the antigen presenting function of these APC was upregulated by Myd88 lpr. As a result of these effects, the antigen presenting function of DC was greatly enhanced by the expression of Myd88lpr.

The data would imply that, in DC and macrophages the inhibition of TRR signalling can result in the activation of the cell. This would suggest that there may be TRR whose role is to inhibit APC, particularly DC function. This suggestion is in-part supported by the observation that the stimulating effect of Myd88lpr is inhibited by simultaneous expression of Myd88wt. Moreover, unlike in Hela cells, where Myd88lpr inhibits IRAK activation, in macrophages, Myd88lpr induces the activation of this kinase.

Besides adding a new layer of complexity to our understanding of TRR signalling and what roles these receptors may have regulating cell function, these data have uncovered a novel pathway involved in controlling antigen presentation activity. This pathway could be harnessed for the therapeutic modulation of the immune system, both for the prevention and treatment of autoimmune disease and allergy, and also in circumstances where one wishes to stimulate the immune system, such as in vaccination. The discovery of these pathways may have a profound impact on vaccine design and on immuno-modulation approaches in general.

Numbered References

1. Rock et al (1998) *PNAS* 95, 588-593
2. O'Neill & Dinarello (2000) *Immunol Today* 21, 206-209
3. Poltorak et al (1998) *Science* 282, 2085-2088
4. Underhill et al (1999) *Nature* 401, 811-815
5. Burns et al (1998) *J Biol Chem* 273, 12203-12209
6. Kawai et al (1999) *Immunity* 11, 115-122
7. Takeuchi et al (2000) *Int Immunol* 163, 978-984
8. Du et al (2000) *Eur Cytokine Netw* 11, 362-371

EXAMPLE 2

Dendritic Cell Culture

Exemplary Dendritic Cell Culture from Normal Volunteers $CD14^+$ peripheral blood monocytes are adhered to tissue culture flasks and cultured in the presence of 1% AB serum, GM-CSF (400 ng/ml) and IL-4 (400 IU/ml) for 7 days. This yields cells with the morphology of DC and a mean of 49% with the $CD1a^+$ marker which is indicative of the immature form of the DC capable of taking up and presenting antigen. These cells are then matured to $CD83^+$ cells by the addition of TNF$\alpha$ (15 ng/ml), which enables the DC to present antigen to cytotoxic T-cells. 7% of the cells become $CD83^+$ within 1 day, but 3 days at least are required for maximum effect. It is possible that monocyte conditioned medium could replace the 1% AB serum but this is probably not desirable.

Exemplary Dendritic Cell Culture from Patients with Cancer

DC are generated from 6 patients with relapsed metastatic disease, both prior to and following salvage chemotherapy (a total of 12 samples of peripheral blood, each of 50 mls).

Clinical Study

Patients donate a single unit of autologous blood according to standard protocol. Patients are evaluated prior to donation by a blood transfusion physician. Autologous donations are screened in the same way as allogeneic donations for routine virus markers (HIV, HBV, HCV and syphilis) and patients give consent to this after appropriate counselling if they wish to participate. This precaution protects clinical and laboratory staff from potential infection and the routine blood supply from the possibility of cross-contamination. The blood is taken into a routine quad-pack. This allows automated separation of red cells, buffy coat and plasma. The buffy coats yields approximately $670 \times 10^6$ mononuclear leukocytes which give approximately $47 \times 10^6$ DC using current techniques. A dosage range of $8-128 \times 10^6$ DC per patient is used. Peripheral blood monocytes are divided into 2 aliquots and pulsed with a TRR signalling inhibitor (for example MyD88lpr, optionally with a promoter of cell uptake) and antigenic peptide, or tumour cell extract between days 1 and 10. Alternatively, peripheral blood monocytes are is exposed to a DNA vaccine construct, for example an adenovirus construct, encoding a TRR signalling inhibitor, (for example MyD88lpr) and encoding an antigenic peptide, and cultured for 10 days possibly with multiple exposures to the vaccine. Serum-free culture conditions or autologous plasma is used in preference to allogeneic AB serum. Cultured DCs are pooled, washed and resuspended in 100 mls saline prior to infusion over 1 hour. The autologous red cell concentrate is not returned to the patient other than for a standard clinical indication. The ex vivo DC culture procedures are carried out following good manufacturing practices.

Patients who donated the initial blood samples will, by this time, have received salvage chemotherapy and may or may not be in clinical remission. Further patients with relapsed metastatic disease receive treatment prior to receiving chemotherapy. There are two treatment regimes:

(1) metastatic relapse, standard therapy followed by adoptive immunotherapy;
(2) metastatic relapse, adoptive immunotherapy followed by standard therapy.

Product infusion is carried out under the direct supervision of an experienced physician on a ward on day bed unit where resuscitation and supportive care facilities are available if required.

The invention claimed is:

1. A method of enhancing presentation of an antigen by a mature or immature dendritic cell, comprising supplying ex vivo to said cell an inhibitor of Toll-related receptor (TRR) signaling which comprises a functional Toll domain and does not comprise a functional death domain, wherein the inhibitor is a dominant negative mutant of MyD88; thereby enhancing antigen presentation.

2. The method of claim 1 wherein the inhibitor of TRR signaling modulates binding of an intracellular molecule to a TRR.

3. The method of claim 1 wherein the inhibitor of TRR signaling modulates binding of MyD88 to a TRR.

4. The method of claim 1 wherein the inhibitor of TRR signaling modulates binding of MyD88 to a polypeptide comprising a death domain (DD).

5. The method of claim 1 wherein the dominant negative mutant is MyD88lpr.

6. The method of claim 1 wherein the dominant negative mutant is expressed in the cell.

7. The method of claim 6 wherein the cell is administered a polynucleotide capable of expressing the dominant negative mutant in the cell.

8. The method of claim 7 wherein the polynucleotide is administered in an adenovirus vector.

9. The method of claim 1 further comprising supplying to said cell said antigen to be presented or a nucleic acid capable of expressing said antigen in the cell.

10. The method of claim 9 wherein both the inhibitor and the antigen are supplied to the cell by expression in the cell.

11. The method of claim 10 wherein the inhibitor and the antigen are provided in a single recombinant polynucleotide molecule.

12. A method of enhancing presentation of an antigen by a mature or immature dendritic cell, comprising supplying ex vivo to said cell an inhibitor of Toll-related receptor (TRR) signaling which comprises a functional Toll domain, does not comprise a functional death domain, and is capable of inhibiting binding of MyD88 to a TRR, wherein the inhibitor is a dominant negative mutant of MyD88; thereby enhancing antigen presentation.

13. A method of enhancing presentation of an antigen by a mature or immature dendritic cell, comprising supplying ex vivo to said cell a dominant negative mutant of MyD88 comprising a functional Toll domain and not a functional death domain, thereby enhancing antigen presentation.

14. A method of enhancing presentation of an antigen by a mature or immature dendritic cell, comprising:
    (a) supplying ex vivo to said cell a dominant negative mutant of MyD88 and
    (b) supplying ex vivo to said cell said antigen to be presented or a nucleic acid capable of expressing said antigen in the cell;
thereby enhancing antigen presentation.

15. A method of enhancing presentation of an antigen by a mature or immature dendritic cell, comprising:
    (a) supplying ex vivo to said cell MyD88lpr and
    (b) supplying ex vivo to said cell said antigen to be presented or a nucleic acid capable of expressing said antigen in the cell;
thereby enhancing antigen presentation.

16. A method of enhancing presentation of an antigen by a mature or immature dendritic cell, comprising:
    (a) supplying ex vivo to said cell a dominant negative MyD88 and
    (b) supplying ex vivo to said cell said antigen to be presented or a nucleic acid capable of expressing said antigen in the cell;
thereby enhancing antigen presentation.

17. The method of claim 14, wherein the dominant negative mutant is expressed in the cell.

18. The method of claim 17, wherein the cell is administered a polynucleotide capable of expressing the dominant negative mutant in the cell.

19. The method of claim 18, wherein the polynucleotide is administered in an adenovirus vector.

20. The method of claim 14, wherein both the inhibitor and the antigen are supplied to the cell by expression in the cell.

21. The method of claim 20, wherein the inhibitor and the antigen are provided in a single recombinant polynucleotide molecule.

* * * * *